United States Patent
He et al.

(10) Patent No.: US 11,447,470 B2
(45) Date of Patent: Sep. 20, 2022

(54) PYRIMIDINONE-CONTAINING COMPOUND, PREPARATION METHOD THEREOF, PHARMACEUTICAL COMPOSITION AND APPLICATION THEREOF

(71) Applicants: YUNNAN UNIVERSITY, Kunming (CN); KUNMING INSTITUTE OF ZOOLOGY, CHINESE ACADEMY OF SCIENCES, Kunming (CN)

(72) Inventors: Yanping He, Kunming (CN); Hongbin Zhang, Kunming (CN); Yongtang Zheng, Kunming (CN); Yumeng Wu, Kunming (CN); Chengrun Tang, Kunming (CN); Ruomei Rui, Kunming (CN); Liumeng Yang, Kunming (CN); Jiangyuan Wang, Kunming (CN)

(73) Assignees: Yunnan University, Kunming (CN); Kunming Institute of Zoology, Chinese Academy of Sciences, Kunming (CN)

( * ) Notice: Subject to any disclaimer, the term of this patent is extended or adjusted under 35 U.S.C. 154(b) by 10 days.

(21) Appl. No.: 16/977,775

(22) PCT Filed: Mar. 4, 2019

(86) PCT No.: PCT/CN2019/076841
§ 371 (c)(1),
(2) Date: Sep. 2, 2020

(87) PCT Pub. No.: WO2019/170050
PCT Pub. Date: Sep. 12, 2019

(65) Prior Publication Data
US 2020/0399248 A1    Dec. 24, 2020

(30) Foreign Application Priority Data
Mar. 6, 2018    (CN) .......................... 201810183285.5

(51) Int. Cl.
C07D 403/12 (2006.01)
C07D 403/14 (2006.01)
C07D 405/14 (2006.01)
A61P 31/18 (2006.01)

(52) U.S. Cl.
CPC ............. C07D 403/12 (2013.01); A61P 31/18 (2018.01); C07D 403/14 (2013.01); C07D 405/14 (2013.01)

(58) Field of Classification Search
CPC .................................................. C07D 403/10
See application file for complete search history.

(56) References Cited

FOREIGN PATENT DOCUMENTS

| CN | 110483487 A | 11/2019 |
| GN | 101066957 A | 11/2007 |
| GN | 103130787 A | 6/2013 |
| WO | 2007043094 A2 | 4/2007 |

OTHER PUBLICATIONS

Banker et al. "Modern Pharmaceutics", 3rd Ed. p. 596 (1996).*
"Burger's Medicinal Chemistry", edited by Manfred E.Wolf, 5th Ed. Part 1, pp. 975-977 (1995).*
Bauer, Journal of Validation Technology, p. 15-23 (2008).*
Fang, et al., Synthesis and Biological Evaluation of a Series of 2-((1-substituted-1H-1,2,3-triazol-4-yl)methylthio)-6-(naphthalen-1-ylmethyl)pyrimidin-4-(3H)-one as Potential HIV-1 Inhibitors, Chem. Biol. Drug Des., vol. 86, No. 4, pp. 614-618 (2015) (Year: 2015).*
International Search Report issued in International Patent Application No. PCT/CN2019/076841, dated Jun. 10, 2019.
Written Opinion of the International Searching Authority issued in International Patent Application No. PCT/CN2019/076841, dated Jun. 10, 2019.
Zengjun Fang et al., "Synthesis and Biological Evaluation of a Series of 2-((1-substituted-1 H-1, 2, 3-triazol-4-yl) methylthio)-6-(naphthalen-1-ylmethyl)pyrimidin-4(3H)-one As Potential HIV-1 Inhibitors," Chem Biol Drug Des, Dec. 31, 2015 (Dec. 31, 2015), pp. 614-618, and compounds in Scheme 1, vol. 86, No. (4).
Hanmant M. Kasralikar et al., "Design and Synthesis of Novel 1,2,3-triazolyl-pyrimidinone Hybrids as Potential Anti-HIV-1 NNRT Inhibitors", Journal of Heterocyclic Chemistry, Feb. 5, 2018 (Feb. 5, 2018), pp. 321-829, and compounds in Table 1, vol. 55, No. (4).
Yan-Ping He et al., "Synthesis and biological evaluation of novel dihydro-aryl/alkylsulfanyl-cyclohexylmethyl-oxopyrimidines (S-DACOs) as high active anti-HIV agents," Bioorg. & Med. Chem., Jan. 2011, pp. 694-697, vol. 21, third paragraph on p. 695.
Maxim B. Nawrozkij et al. "5-Alkyl-6-benzyl-2-(2-oxo-2-phenylethylsulfanyl)pyrimidin-4(3H)-ones, a series of anti-HIV-1 agents of the dihydro-alkoxy-benzyl-oxopyrimidine family with peculiar structure-activity relationship profile," J. Med. Chem., Aug. 2008, pp. 4641-4652, vol. 51.

(Continued)

Primary Examiner — Erich A Leeser
(74) Attorney, Agent, or Firm — Pilloff Passino & Cosenza LLP; Sean A. Passino; Rachel K. Pilloff

(57) ABSTRACT

Disclosed is a pyrimidinone-containing compound represented by formula I, a preparation method thereof, a pharmaceutical composition, and an application thereof. The pyrimidinone-containing compound of the present disclosure can be used as HIV-1 inhibitor and can be also used in the treatment of human immunodeficiency virus infection.

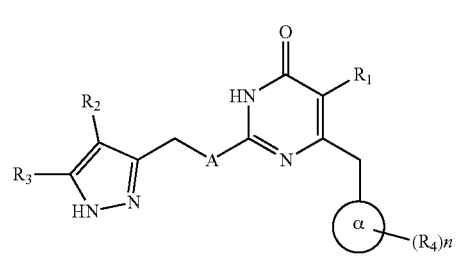

20 Claims, No Drawings

(56) References Cited

OTHER PUBLICATIONS

Stephen M. Berge et al. "Pharmaceutical Salts", Journal of Pharmaceutical Science, Jan. 1977, pp. 1-19, vol. 66, No. 1.
Remington: The Science and Practice of Pharmacy, 21st Ed., Lippincott, Williams & Wilkins (2005).
Hubert Maehr, "A Proposed New Convention for Graphic Presentation of Molecular Geometry and Topography," J. Chem. Ed. Feb. 1985, pp. 114-120, vol. 62.
Chinese Office Action issued in Chinese Patent Application No. 2018101832855, dated Dec. 16, 2021.
Marco Radi et al., "Synthesis, Biological Activity, and ADME Properties of Novels-DABOs/N-DABOs as HIV Reverse Transcriptase Inhibitors," ChemMedChem, May 2012, pp. 883-896, Issue 7.

\* cited by examiner

PYRIMIDINONE-CONTAINING COMPOUND, PREPARATION METHOD THEREOF, PHARMACEUTICAL COMPOSITION AND APPLICATION THEREOF

This application claims the benefit of Chinese Patent Application No. CN201810183285.5 filed on Mar. 6, 2018, the contents of which are incorporated herein by reference in their entireties.

TECHNICAL FIELD

The present disclosure pertains to the field of chemical synthesis and pharmaceutical technology, specifically relates to a pyrimidinone-containing compound, and a preparation method, pharmaceutical composition and use thereof.

BACKGROUND ART

Acquired immunodeficiency syndrome (i.e., AIDS) is a disease caused by infection of human immunodeficiency virus (HIV) in the body. Reverse transcriptase (RT) is the key enzyme that catalyzes the conversion of viral RNA to DNA, and it is also a key target for the design of anti-AIDS drugs.

Non-nucleoside reverse transcriptase inhibitors (NNRTIs) have many advantages such as high efficiency, low toxicity, and good selectivity and are important components of current effective antiretroviral therapy (cART) for AIDS. Although the emergence of cART has greatly reduced the mortality rate of AIDS patients and improved the quality of life, the existing drugs cannot eliminate the virus, need to be taken for life and are accompanied by drug resistance and serious toxic side effects such as dyslipidemia, insulin resistance, lipodystrophy, heart disease and other related diseases, which are the major reasons for the failure of cART. At present, more than 60 types of NNRTIs have been reported, all of which bind to a binding pocket (NNBP) about 0X away from the RT catalytic center despite the divergence of their structures. This binding pocket is highly flexible and makes the design of structurally diverse NNRTIs possible.

Currently, there are five HIV reverse transcriptase inhibitors approved by the FDA of U.S.A, namely: nevirapine, delavirdine, efavirenz, etravirine and rilpivirine. Because of the high variability of HIV-1 virus, drug-resistant mutations such as L100A, H103N, Y181C and Y181C+K103N have been produced after the first-generation NNRTIs (nevirapine, delavirdine) are widely used in clinic. The second-generation NNRTIs (etravirine (ETV) and ripaverine (RPV)) have high inhibitory activity against a variety of drug-resistant strains, but their generally poor water solubility and membrane permeability lead to low bioavailability and increased oral dose, thereby causing toxic and side effects and cross-resistance. For example, etravirine has severe skin allergic reactions, and ripaverine has toxic and side effects such as depression, insomnia, acute respiratory distress syndrome, rash, and headache.

Therefore, the research of novel NNRTIs having high efficacy, low toxicity, broad-spectrum anti-drug resistance and good pharmacokinetic properties is still a hot field in the research and development of anti-HIV drugs.

CONTENT OF THE DISCLOSURE

The technical problem to be solved by the present disclosure is to overcome the deficiencies of existing non-nucleoside HIV-1 reverse transcriptase inhibitors (NNRTIs) that generally have poor water solubility and membrane permeability, resulting in low bioavailability and increased oral dose and further causing toxic and side effects and cross-resistance, thus providing a pyrimidinone-containing compound different from the prior art, and a preparation method, pharmaceutical composition and use thereof. The compound of the present disclosure can be used as a HIV-1 inhibitor and can be used in the manufacture of a medicament for treating and/or preventing immunodeficiency virus (HIV).

The present disclosure solves the above technical problems through the following technical solutions.

The present disclosure provides a compound represented by formula I, or a N-oxide, tautomer, optical isomer, hydrate, solvate, polymorph, pharmaceutically acceptable salt thereof or a prodrug thereof:

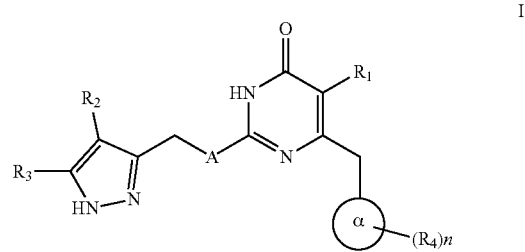

wherein:

A is S, O, NH or NCH$_3$;

R$_1$ is H, C$_1$-C$_6$ branched or straight chain alkyl, or C$_3$-C$_6$ cycloalkyl;

R$_2$ is H or halogen;

R$_3$ is H, C$_1$-C$_{12}$ branched or straight chain alkyl, C$_3$-C$_6$ cycloalkyl, C$_6$-C$_{20}$ aryl, C$_2$-C$_{10}$ heteroaryl, C$_6$-C$_{20}$ aryl substituted by one or more (e.g., 1-6, preferably 1-3 or 1-2) R$_{3a}$, or C$_2$-C$_{10}$ heteroaryl substituted by one or more (e.g., 1-6, preferably 1-3 or 1-2) R$_{3b}$; wherein each of R$_{3a}$ and R$_{3b}$ is independently selected from hydroxyl, nitro, halogen, amino, cyano, HOS(=O)$_2$—, CH$_3$S(=O)$_2$—, C$_1$-C$_6$ branched or straight chain alkyl-S(=O)$_2$NH—, C$_1$-C$_6$ branched or straight chain alkyl, C$_1$-C$_6$ branched or straight chain alkoxy, C$_1$-C$_6$ branched or straight chain alkylthio, C$_1$-C$_6$ branched or straight chain haloalkyl, when the number of R$_{3a}$ or R$_{3b}$ is more, then each R$_{3a}$ or each R$_{3b}$ is the same or different.

α ring is cyclohexyl or phenyl, wherein the phenyl is substituted by n R$_4$ where each R$_4$ is the same or different, n is 0, 1, 2, 3 or 4; R$_4$ is halogen, hydroxyl, cyano, nitro, amino, C$_1$-C$_6$ branched or straight chain alkyl, or C$_1$-C$_6$ branched or straight chain alkoxy.

In the present disclosure, when R$_1$ is C$_1$-C$_6$ branched or straight chain alkyl, then the C$_1$-C$_6$ branched or straight chain alkyl is preferably C$_1$-C$_3$ branched or straight chain alkyl, further preferably isopropyl, n-propyl, ethyl or methyl;

when R$_1$ is C$_3$-C$_6$ cycloalkyl, then the C$_3$-C$_6$ cycloalkyl is preferably cyclopropyl, cyclobutyl, cyclopentyl or cyclohexyl.

In the present disclosure, when R$_2$ is halogen, then the halogen is preferably fluorine, chlorine, bromine or iodine, further preferably chlorine;

In the present disclosure, when R$_3$ is C$_1$-C$_{12}$ branched or straight chain alkyl, then the C$_1$-C$_{12}$ branched or straight chain alkyl is preferably $C_1$-$C_6$ branched or straight chain alkyl, further preferably $C_1$-$C_4$ branched or straight chain alkyl, more further preferably methyl, ethyl, propyl, isopropyl, n-butyl, isobutyl, sec-butyl or tert-butyl;

when $R_3$ is $C_3$-$C_6$ cycloalkyl, then the $C_3$-$C_6$ cycloalkyl is preferably cyclopropyl, cyclobutyl, cyclopentyl or cyclohexyl;

when $R_3$ is $C_6$-$C_{20}$ aryl substituted by one or more $R_{3a}$, then the $C_6$-$C_{20}$ aryl is preferably $C_6$-$C_{10}$ aryl, further preferably phenyl; the $C_6$-$C_{20}$ aryl substituted by one or more $R_{3a}$ is preferably

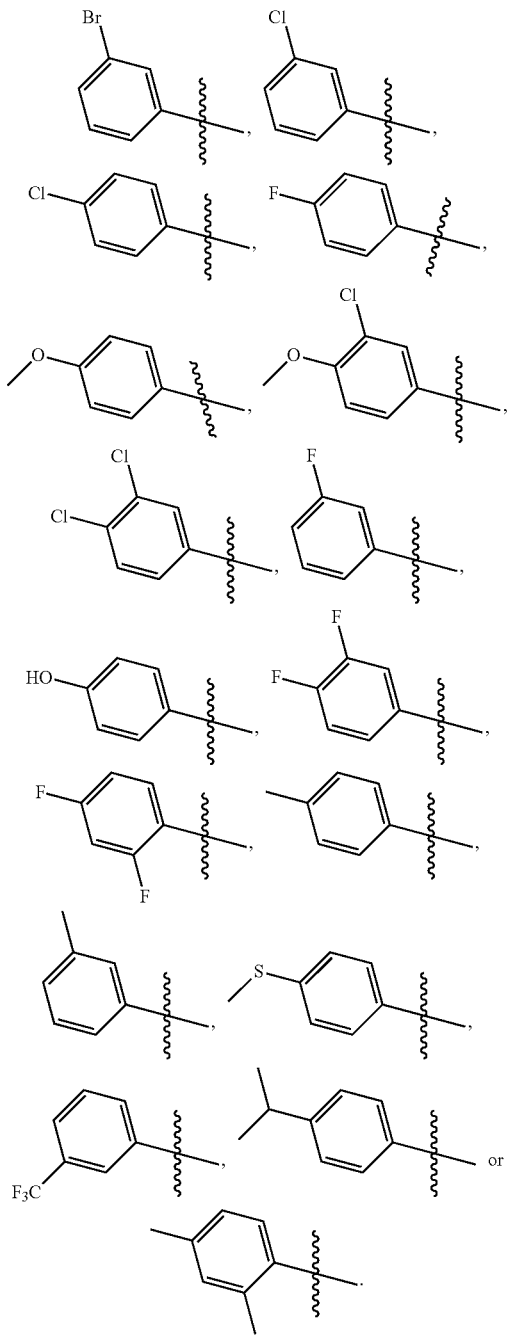

When $R_3$ is $C_2$-$C_{10}$ heteroaryl substituted by one or more $R_{3b}$, then the $C_2$-$C_{10}$ heteroaryl is preferably $C_2$-$C_6$ heteroaryl, further preferably pyridyl, pyridazinyl, pyrimidinyl, pyrazinyl, furanyl, thienyl, pyrrolyl, pyrazolyl, imidazolyl, oxazolyl, isoxazolyl, thiazolyl, pyrimidinonyl, oxadiazolyl, pyridonyl or triazolyl.

In the present disclosure, when $R_{3a}$ or $R_{3b}$ is halogen, then the halogen is preferably fluorine, chlorine, bromine or iodine;

when $R_{3a}$ or $R_{3b}$ is $C_1$-$C_6$ branched or straight chain alkyl-S($=$O)$_2$NH—, then the $C_1$-$C_6$ branched or straight chain alkyl is preferably $C_1$-$C_3$ branched or straight chain alkyl, further preferably methyl, ethyl, n-propyl or isopropyl;

when $R_{3a}$ or $R_{3b}$ is $C_1$-$C_6$ branched or straight chain alkyl, then the $C_1$-$C_6$ branched or straight chain alkyl is preferably $C_1$-$C_3$ branched or straight chain alkyl, further preferably methyl, ethyl, n-propyl or isopropyl;

when $R_{3a}$ or $R_{3b}$ is $C_1$-$C_6$ branched or straight chain alkoxy, then the $C_1$-$C_6$ branched or straight chain alkoxy is preferably $C_1$-$C_3$ branched or straight chain alkoxy, further preferably methoxy, ethoxy, propoxy or isopropoxy;

when $R_{3a}$ or $R_{3b}$ is $C_1$-$C_6$ branched or straight chain alkylthio, then the $C_1$-$C_6$ branched or straight chain alkylthio is preferably $C_1$-$C_3$ branched or straight chain alkylthio, further preferably methylthio, ethylthio, propylthio or isopropylthio;

when $R_{3a}$ or $R_{3b}$ is $C_1$-$C_6$ branched or straight chain haloalkyl, then the $C_1$-$C_6$ straight or branched chain haloalkyl is $C_1$-$C_6$ straight or branched chain alkyl substituted by one or more halogen atoms, where each halogen atom is the same or different and can be on the same or different carbon atoms; the $C_1$-$C_6$ straight or branched chain haloalkyl is preferably $C_1$-$C_3$ straight or branched chain haloalkyl, further preferably trifluoromethyl, difluoromethyl, or 1,2-difluoroethyl.

In the present disclosure, when $R_3$ is phenyl substituted by one or more $R_{3a}$, then the substituted is preferably mono-substituted or di-substituted, the mono-substituted is preferably 3-substituted or 4-substituted; the di-substituted is preferably 2,4-di-substituted or 3,4-di-substituted.

In the present disclosure, when $R_4$ is halogen, then the halogen is preferably fluorine, chlorine, bromine or iodine;

when $R_4$ is $C_1$-$C_6$ branched or straight chain alkyl, then the $C_1$-$C_6$ branched or straight chain alkyl is preferably $C_1$-$C_3$ branched or straight chain alkyl, further preferably methyl, ethyl, n-propyl or isopropyl;

when $R_4$ is $C_1$-$C_6$ branched or straight chain alkoxy, then the $C_1$-$C_6$ branched or straight chain alkoxy is preferably $C_1$-$C_3$ branched or straight chain alkoxy, further preferably methoxy, ethoxy, propoxy or isopropoxy.

In the present disclosure, when α ring is phenyl substituted by n $R_4$ where each $R_4$ is the same or different, then n is preferably 2, preferably all $R_4$ are halogen or all $R_4$ are $C_1$-$C_6$ branched or straight chain alkyl; further preferably all $R_4$ are fluorine, or all $R_4$ are chlorine, or all $R_4$ are methyl; $R_4$ is preferably located in the 2-position and 6-position of the phenly, or 3-position and 5-position of the phenyl.

In the present disclosure, when α ring is phenyl substituted by n $R_4$ where each $R_4$ is the same or different, then n is preferably 2, preferably the two $R_4$ are $C_1$-$C_6$ branched or straight chain alkoxy, further preferably, the two $R_4$ can be linked together to form a ring, i.e., form an oxygen-containing heterocycle fused to the phenyl. When the two $R_4$ form an oxygen-containing heterocycle fused to the phenyl, then the two $R_4$ preferably form an oxygen-containing 5-7 membered heterocycle fused to the phenyl, e.g.,

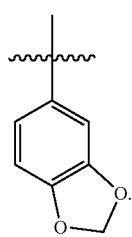 [SMILES: *c1ccc2c(c1)OCO2]

In a preferred embodiment of the present disclosure, A is S.

In a preferred embodiment of the present disclosure, α ring is

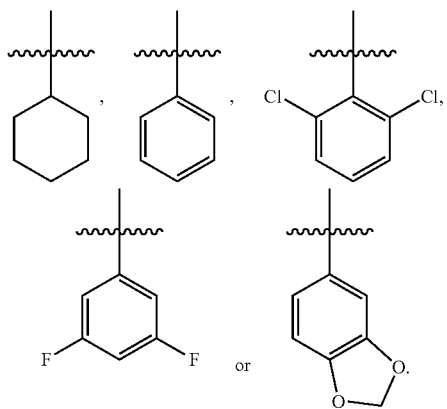

In a preferred embodiment of the present disclosure, $R_1$ is H, methyl, ethyl or isopropyl.

In a preferred embodiment of the present disclosure, $R_2$ is H or Cl.

In a preferred embodiment of the present disclosure, $R_3$ is $C_6$-$C_2$ aryl, $C_2$-$C_{10}$ heteroaryl, $C_6$-$C_{20}$ aryl substituted by one or more (e.g., 1-6, preferably 1-3 or 1-2) $R_{3a}$, or $C_2$-$C_{10}$ heteroaryl substituted by one or more (e.g., 1-6, preferably 1-3 or 1-2) $R_{3b}$.

In a preferred embodiment of the present disclosure, A is S, α ring is

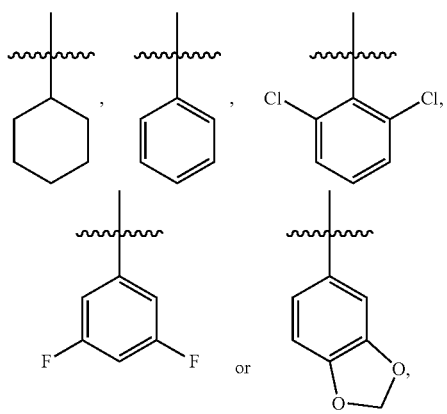

$R_1$ is ethyl or isopropyl; $R_2$ is H or Cl; $R_3$ is $C_6$-$C_{20}$ aryl, $C_2$-$C_{10}$ heteroaryl, $C_6$-$C_{20}$ aryl substituted by one or more (e.g., 1-6, preferably 1-3 or 1-2) $R_{3a}$, or $C_2$-$C_{10}$ heteroaryl substituted by one or more (e.g., 1-6, preferably 1-3 or 1-2) $R_{3b}$.

In a preferred embodiment of the present disclosure, A is S, α ring is cyclohexyl, $R_1$ is ethyl or isopropyl; $R_2$ is H or Cl; $R_3$ is $C_6$-$C_2$ aryl, $C_2$-$C_{10}$ heteroaryl, $C_6$-$C_2$ aryl substituted by one or more (e.g., 1-6, preferably 1-3 or 1-2) $R_{3a}$, or $C_2$-$C_{10}$ heteroaryl substituted by one or more (e.g., 1-6, preferably 1-3 or 1-2) $R_{3b}$.

In a preferred embodiment of the present disclosure, $R_3$ is $C_6$-$C_{20}$ aryl substituted by one or more (e.g., 1-6, preferably 1-3 or 1-2) $R_{3a}$, wherein the $C_6$-$C_{20}$ aryl is phenyl; $R_{3a}$ is hydroxyl, halogen, $C_1$-$C_6$ branched or straight chain alkyl, $C_1$-$C_6$ branched or straight chain alkoxy, $C_1$-$C_6$ branched or straight chain alkylthio, or $C_1$-$C_6$ branched or straight chain haloalkyl.

In a preferred embodiment of the present disclosure, A is S, α ring is

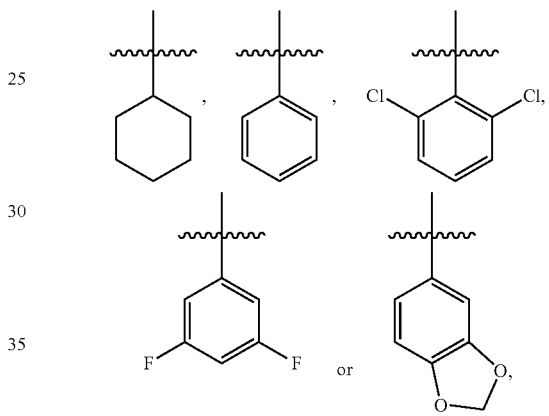

$R_1$ is ethyl or isopropyl; $R_2$ is H or Cl; $R_3$ is phenyl or phenyl substituted by one $R_{3a}$, wherein $R_{3a}$ is hydroxyl, halogen, $C_1$-$C_6$ branched or straight chain alkoxy or $C_1$-$C_6$ branched or straight chain alkylthio; the substituted is 4-substituted.

In a preferred embodiment of the present disclosure, A is S, α ring is cyclohexyl, $R_1$ is ethyl or isopropyl; $R_2$ is H or Cl; $R_3$ is phenyl or phenyl substituted by one $R_{3a}$, wherein $R_{3a}$ is hydroxyl, halogen, $C_1$-$C_6$ branched or straight chain alkoxy or $C_1$-$C_6$ branched or straight chain alkylthio; the substituted is 4-substituted.

In a preferred embodiment of the present disclosure, A is S, α ring is cyclohexyl, $R_1$ is ethyl or isopropyl; $R_2$ is H or Cl; $R_3$ is phenyl or phenyl substituted by one $R_{3a}$, wherein $R_{3a}$ is hydroxyl, F, Cl, methoxy or methylthio; the substituted is 4-substituted.

In a preferred embodiment of the present disclosure, the moiety

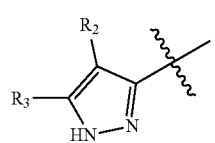

contained in the compound represented by formula I is
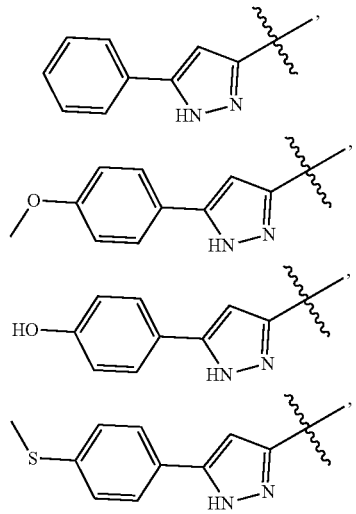
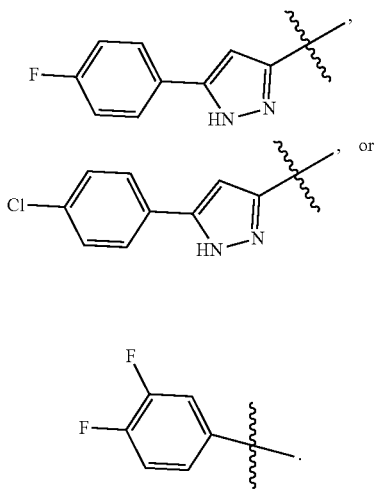
In the present disclosure, the compound represented by formula I is preferably any one of the following compounds:
| Compound | Structure |
|---|---|
| I-1 | 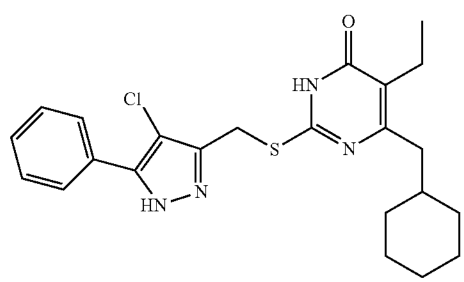 [SMILES: CCc1c(CC2CCCCC2)nc(SCc2n[nH]c(-c3ccccc3)c2Cl)[nH]c1=O] |
| I-2 | 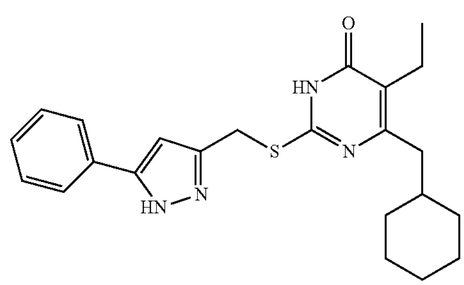 [SMILES: CCc1c(CC2CCCCC2)nc(SCc2cc(-c3ccccc3)[nH]n2)[nH]c1=O] |
| I-3 | 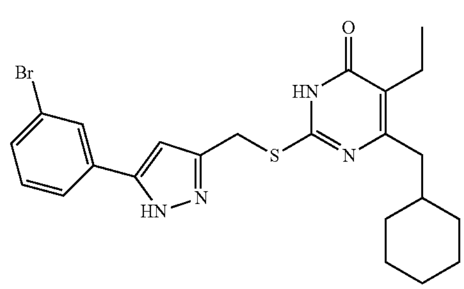 [SMILES: CCc1c(CC2CCCCC2)nc(SCc2cc(-c3cccc(Br)c3)[nH]n2)[nH]c1=O] |

-continued

| Compound | Structure |
|---|---|
| I-4 | 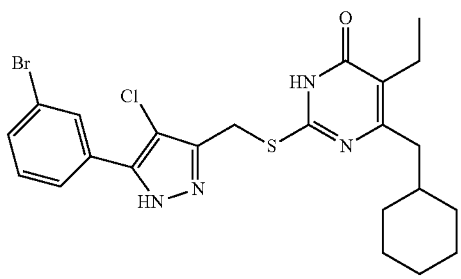 [SMILES: CCc1c(CC2CCCCC2)nc(SCc2n[nH]c(-c3cccc(Br)c3)c2Cl)[nH]c1=O] |
| I-5 | 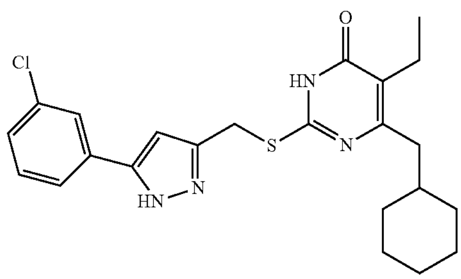 |
| I-6 | 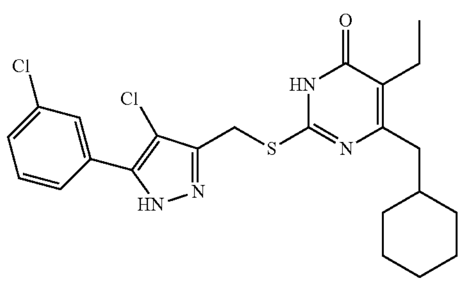 [SMILES: CCc1c(CC2CCCCC2)nc(SCc2n[nH]c(-c3cccc(Cl)c3)c2Cl)[nH]c1=O] |
| I-7 | 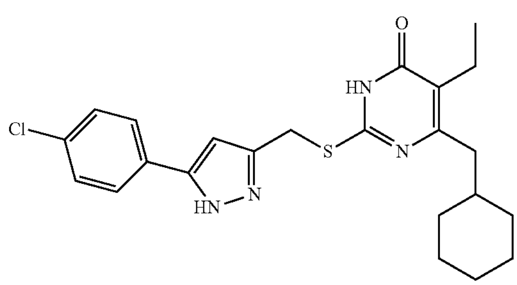 [SMILES: CCc1c(CC2CCCCC2)nc(SCc2cc(-c3ccc(Cl)cc3)[nH]n2)[nH]c1=O] |
| I-8 | 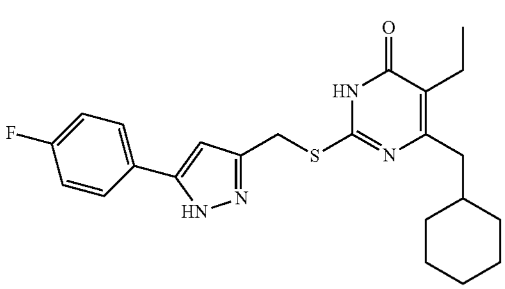 [SMILES: CCc1c(CC2CCCCC2)nc(SCc2cc(-c3ccc(F)cc3)[nH]n2)[nH]c1=O] |

| Compound | Structure |
|---|---|
| I-9 | 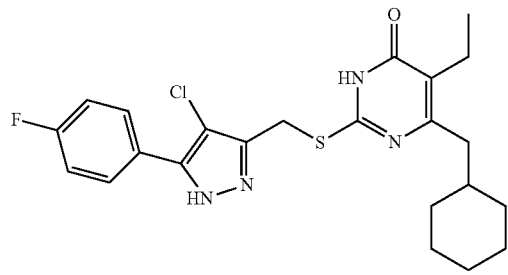 [SMILES: CCc1c(CC2CCCCC2)nc(SCc2n[nH]c(-c3ccc(F)cc3)c2Cl)[nH]c1=O] |
| I-10 | 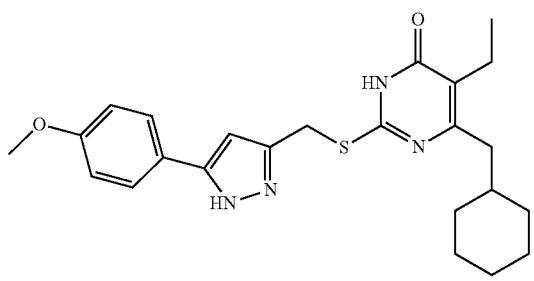 |
| I-11 | 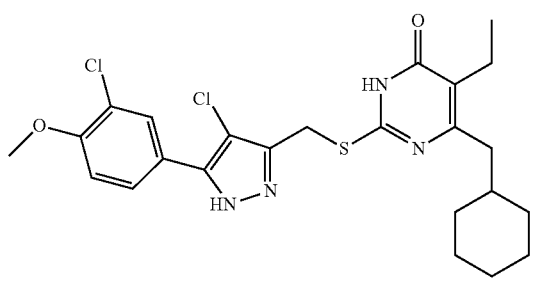 [SMILES: CCc1c(CC2CCCCC2)nc(SCc2n[nH]c(-c3ccc(OC)c(Cl)c3)c2Cl)[nH]c1=O] |
| I-12 | 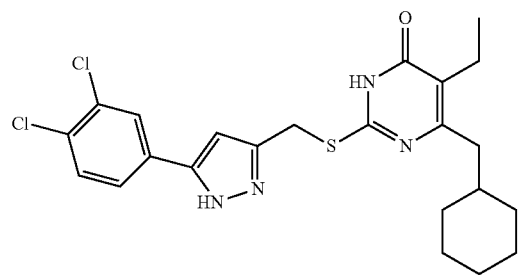 [SMILES: CCc1c(CC2CCCCC2)nc(SCc2cc(-c3ccc(Cl)c(Cl)c3)[nH]n2)[nH]c1=O] |
| I-13 | 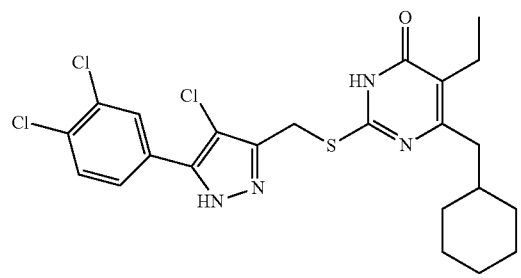 [SMILES: CCc1c(CC2CCCCC2)nc(SCc2n[nH]c(-c3ccc(Cl)c(Cl)c3)c2Cl)[nH]c1=O] |

-continued
| Compound | Structure |
|---|---|
| I-14 | 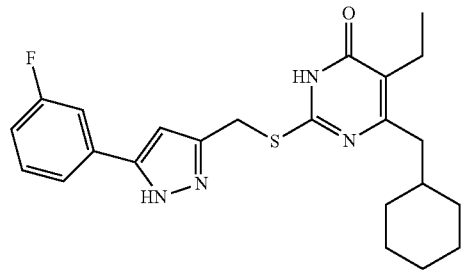 [SMILES: CCc1c(CC2CCCCC2)nc(SCc2cc(-c3cccc(F)c3)[nH]n2)[nH]c1=O] |
| I-15 | 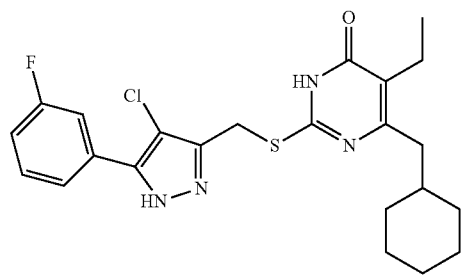 [SMILES: CCc1c(CC2CCCCC2)nc(SCc2n[nH]c(-c3cccc(F)c3)c2Cl)[nH]c1=O] |
| I-16 | 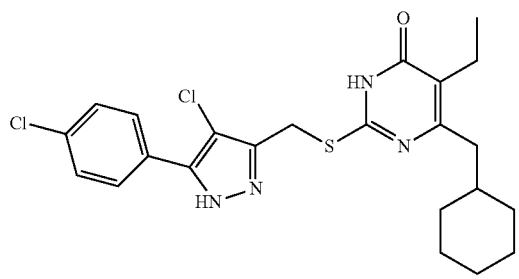 [SMILES: CCc1c(CC2CCCCC2)nc(SCc2n[nH]c(-c3ccc(Cl)cc3)c2Cl)[nH]c1=O] |
| I-17 | 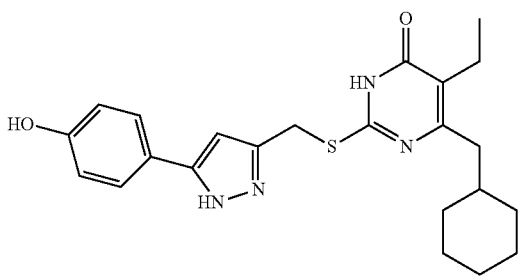 [SMILES: CCc1c(CC2CCCCC2)nc(SCc2cc(-c3ccc(O)cc3)[nH]n2)[nH]c1=O] |
| I-18 | 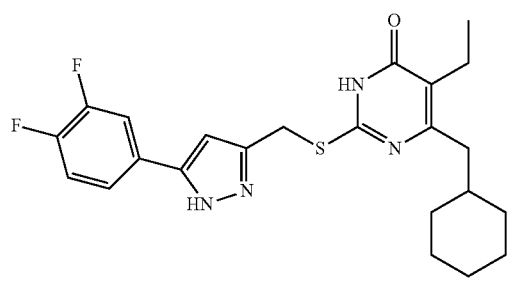 [SMILES: CCc1c(CC2CCCCC2)nc(SCc2cc(-c3ccc(F)c(F)c3)[nH]n2)[nH]c1=O] |

-continued
| Compound | Structure |
|---|---|
| I-19 | 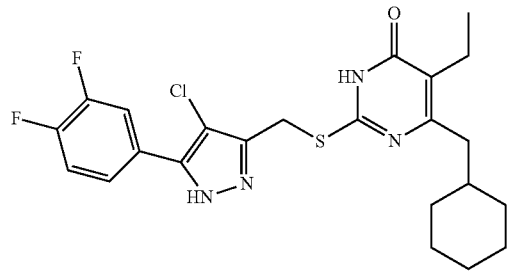 [SMILES: CCc1c(CC2CCCCC2)nc(SCc2n[nH]c(-c3ccc(F)c(F)c3)c2Cl)[nH]c1=O] |
| I-20 | 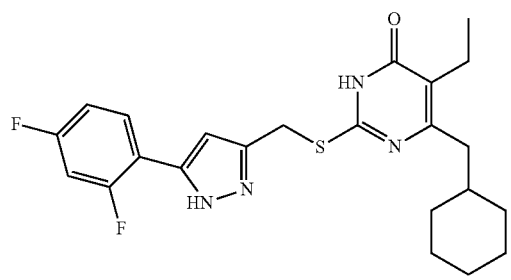 [SMILES: CCc1c(CC2CCCCC2)nc(SCc2cc(-c3ccc(F)cc3F)[nH]n2)[nH]c1=O] |
| I-21 | 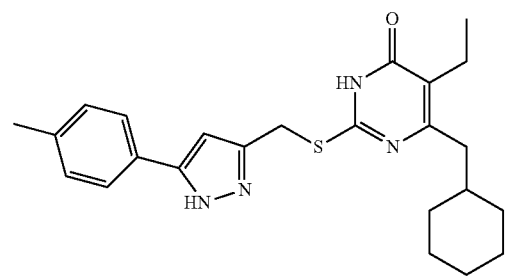 [SMILES: CCc1c(CC2CCCCC2)nc(SCc2cc(-c3ccc(C)cc3)[nH]n2)[nH]c1=O] |
| I-22 | 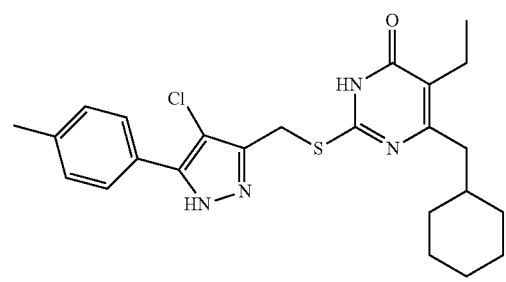 [SMILES: CCc1c(CC2CCCCC2)nc(SCc2n[nH]c(-c3ccc(C)cc3)c2Cl)[nH]c1=O] |
| I-23 | 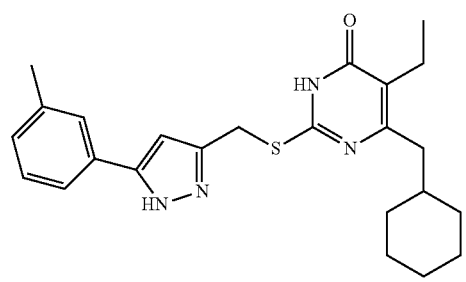 [SMILES: CCc1c(CC2CCCCC2)nc(SCc2cc(-c3cccc(C)c3)[nH]n2)[nH]c1=O] |

-continued

| Compound | Structure |
|---|---|
| I-24 | 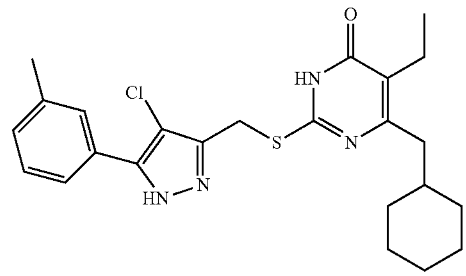 |
| I-25 | 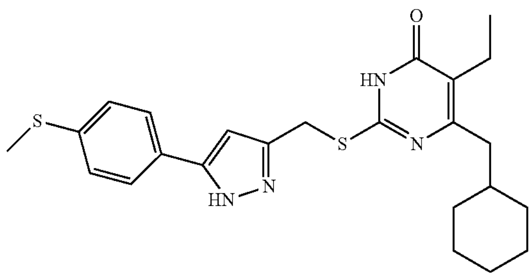 [SMILES: CCc1c(CC2CCCCC2)nc(SCc2cc(-c3ccc(SC)cc3)[nH]n2)[nH]c1=O] |
| I-26 | 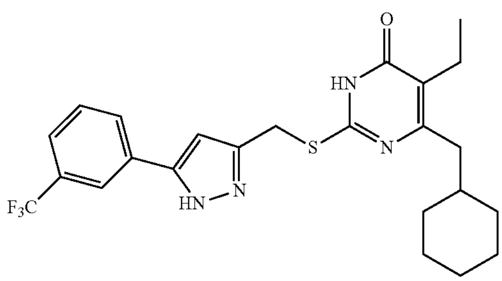 [SMILES: CCc1c(CC2CCCCC2)nc(SCc2cc(-c3cccc(C(F)(F)F)c3)[nH]n2)[nH]c1=O] |
| I-27 | 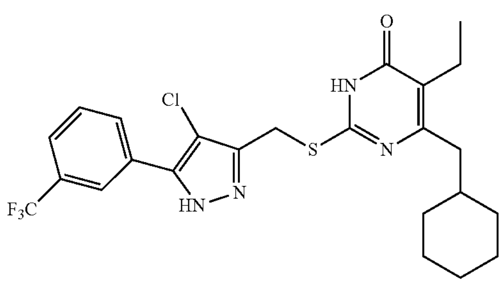 [SMILES: CCc1c(CC2CCCCC2)nc(SCc2n[nH]c(-c3cccc(C(F)(F)F)c3)c2Cl)[nH]c1=O] |
| I-28 | 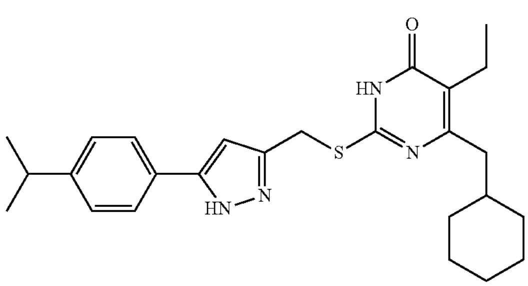 [SMILES: CCc1c(CC2CCCCC2)nc(SCc2cc(-c3ccc(C(C)C)cc3)[nH]n2)[nH]c1=O] |

-continued

| Compound | Structure |
|---|---|
| I-29 | 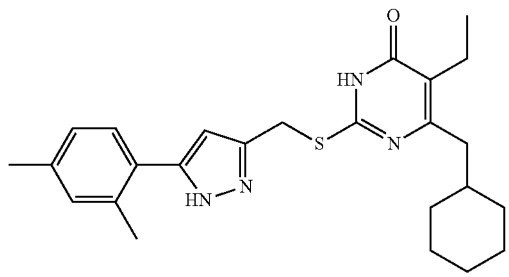 [SMILES: CCc1c(CC2CCCCC2)nc(SCc2cc(-c3ccc(C)cc3C)[nH]n2)[nH]c1=O] |
| I-30 | 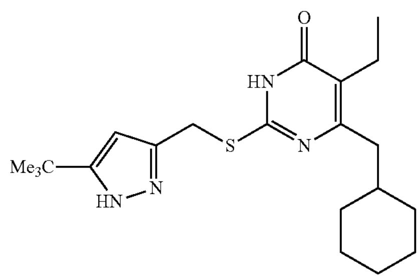 |
| I-31 | 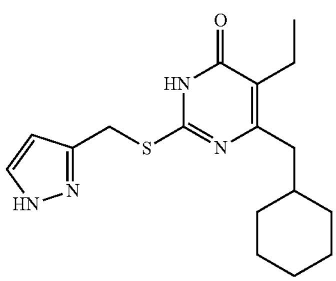 [SMILES: CCc1c(CC2CCCCC2)nc(SCc2cc[nH]n2)[nH]c1=O] |
| I-32 | 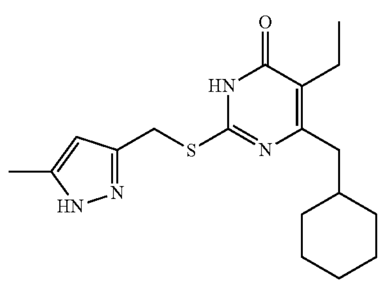 [SMILES: CCc1c(CC2CCCCC2)nc(SCc2cc(C)[nH]n2)[nH]c1=O] |
| I-33 | 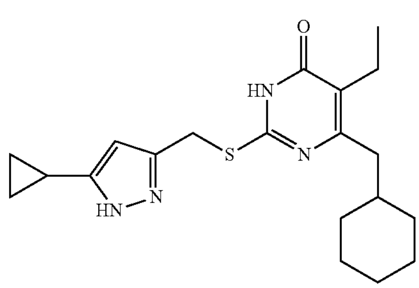 [SMILES: CCc1c(CC2CCCCC2)nc(SCc2cc(C3CC3)[nH]n2)[nH]c1=O] |

-continued
| Compound | Structure |
|---|---|
| I-34 | 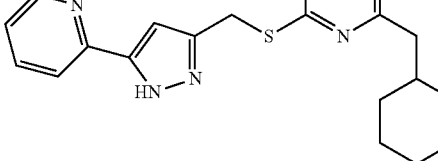 |
| I-35 | 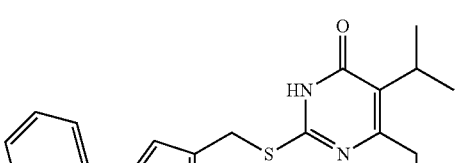 |
| I-36 | 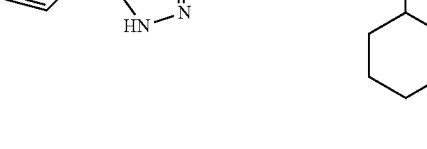 |
| I-37 | 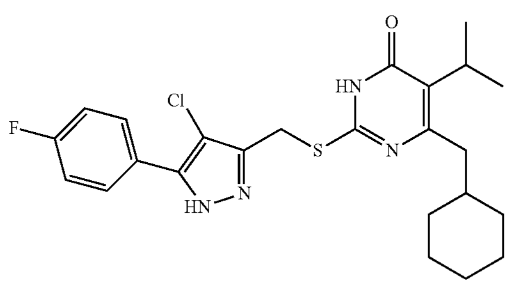 [SMILES: CC(C)c1c(CC2CCCCC2)nc(SCc2n[nH]c(-c3ccc(F)cc3)c2Cl)[nH]c1=O] |
| I-38 | 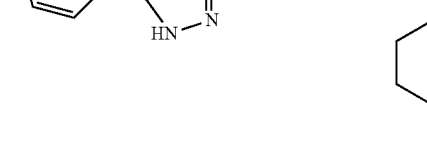 |

-continued

| Compound | Structure |
|---|---|
| I-39 | 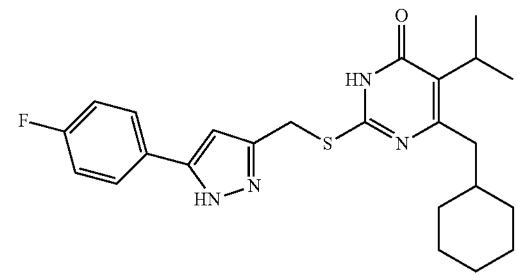 [SMILES: CC(C)c1c(CC2CCCCC2)nc(SCc2cc(-c3ccc(F)cc3)[nH]n2)[nH]c1=O] |
| I-40 | 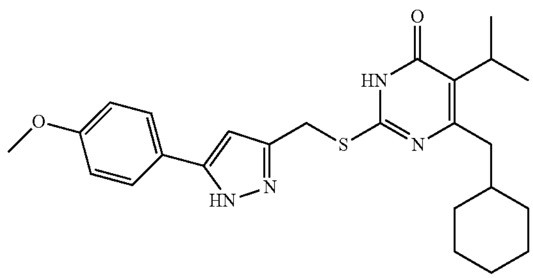 [SMILES: COc1ccc(-c2cc(CSc3nc(CC4CCCCC4)c(C(C)C)c(=O)[nH]3)n[nH]2)cc1] |
| I-41 | 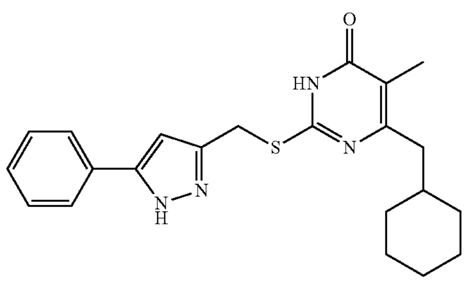 [SMILES: Cc1c(CC2CCCCC2)nc(SCc2cc(-c3ccccc3)[nH]n2)[nH]c1=O] |
| I-42 | 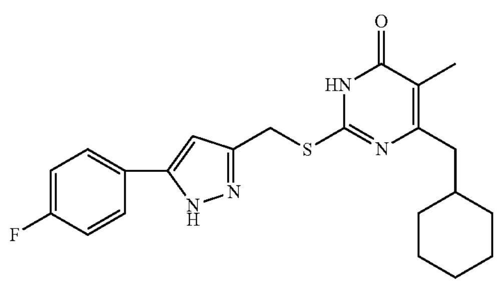 [SMILES: Cc1c(CC2CCCCC2)nc(SCc2cc(-c3ccc(F)cc3)[nH]n2)[nH]c1=O] |
| I-43 | 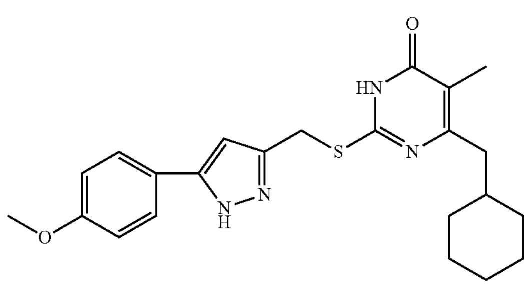 [SMILES: COc1ccc(-c2cc(CSc3nc(CC4CCCCC4)c(C)c(=O)[nH]3)n[nH]2)cc1] |

-continued
| Compound | Structure |
|---|---|
| I-44 | 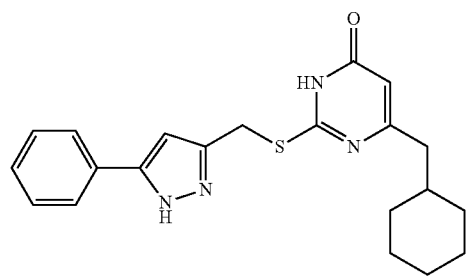 |
| I-45 | 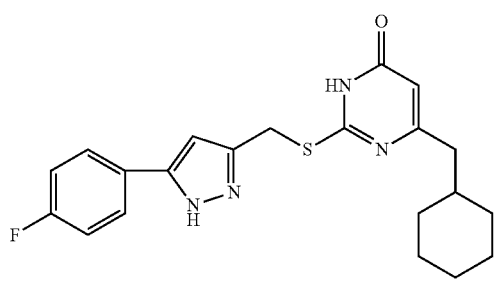 [SMILES: O=c1cc(CC2CCCCC2)nc(SCc2cc(-c3ccc(F)cc3)[nH]n2)[nH]1] |
| I-46 | 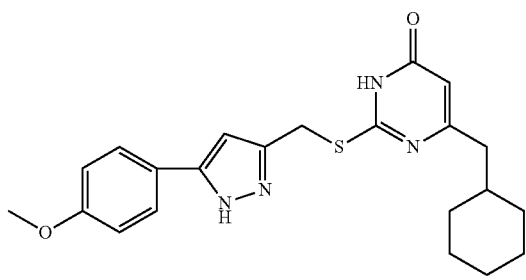 [SMILES: COc1ccc(-c2cc(CSc3nc(CC4CCCCC4)cc(=O)[nH]3)n[nH]2)cc1] |
| I-47 | 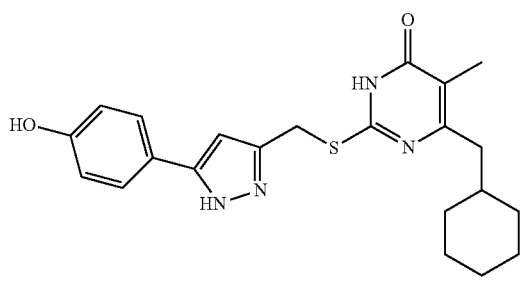 [SMILES: Cc1c(CC2CCCCC2)nc(SCc2cc(-c3ccc(O)cc3)[nH]n2)[nH]c1=O] |
| I-48 | 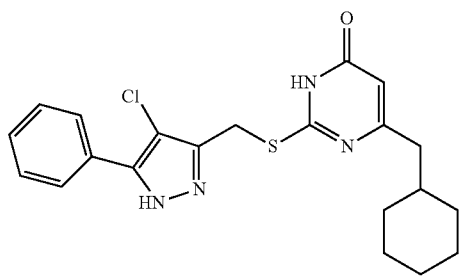 [SMILES: O=c1cc(CC2CCCCC2)nc(SCc2n[nH]c(-c3ccccc3)c2Cl)[nH]1] |

| Compound | Structure |
|---|---|
| I-49 | 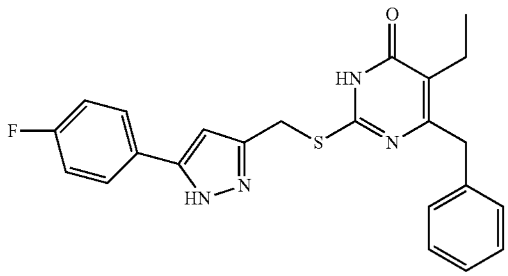 [SMILES: CCc1c(Cc2ccccc2)nc(SCc2cc(-c3ccc(F)cc3)[nH]n2)[nH]c1=O] |
| I-50 | 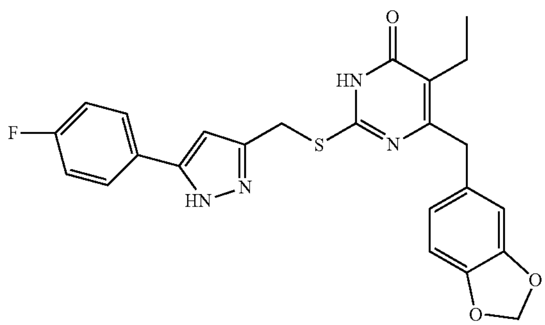 [SMILES: CCc1c(Cc2ccc3c(c2)OCO3)nc(SCc2cc(-c3ccc(F)cc3)[nH]n2)[nH]c1=O] |
| I-51 | 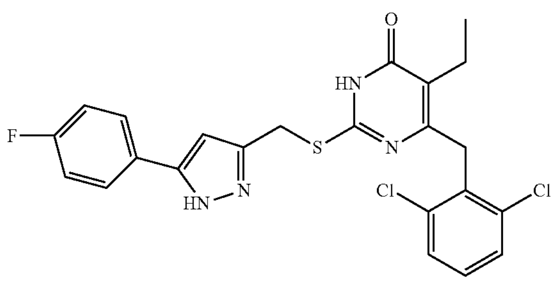 [SMILES: CCc1c(Cc2c(Cl)cccc2Cl)nc(SCc2cc(-c3ccc(F)cc3)[nH]n2)[nH]c1=O] |
| I-52 | 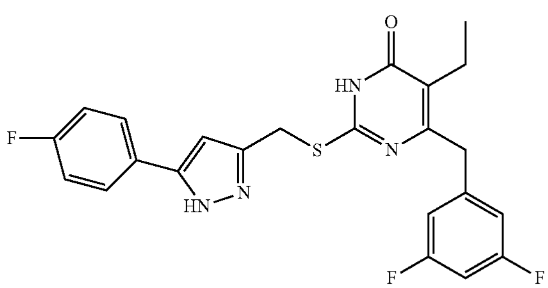 [SMILES: CCc1c(Cc2cc(F)cc(F)c2)nc(SCc2cc(-c3ccc(F)cc3)[nH]n2)[nH]c1=O] |
| I-53 | 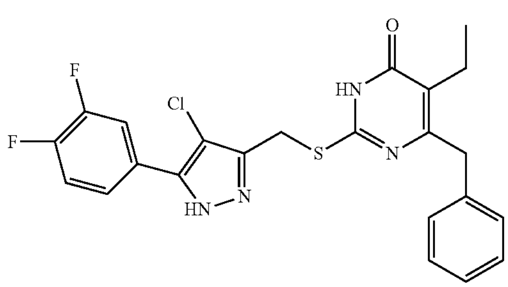 [SMILES: CCc1c(Cc2ccccc2)nc(SCc2n[nH]c(-c3ccc(F)c(F)c3)c2Cl)[nH]c1=O] |

-continued

| Compound | Structure |
|---|---|
| I-54 | 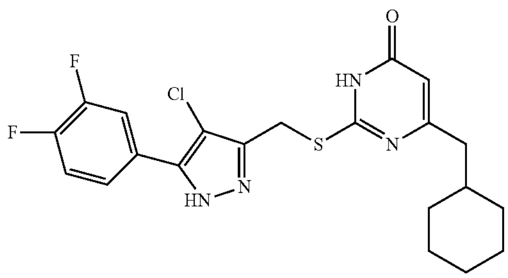 [SMILES: O=c1cc(CC2CCCCC2)nc(SCc2n[nH]c(-c3ccc(F)c(F)c3)c2Cl)[nH]1] |
| I-55 | 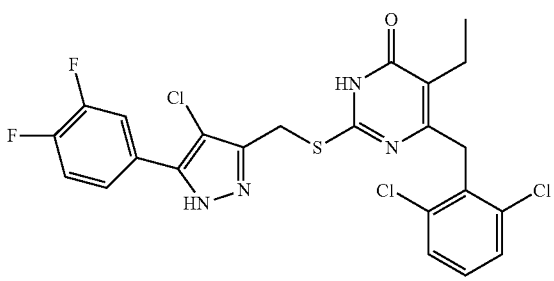 [SMILES: CCc1c(Cc2c(Cl)cccc2Cl)nc(SCc2n[nH]c(-c3ccc(F)c(F)c3)c2Cl)[nH]c1=O] |
| I-56 | 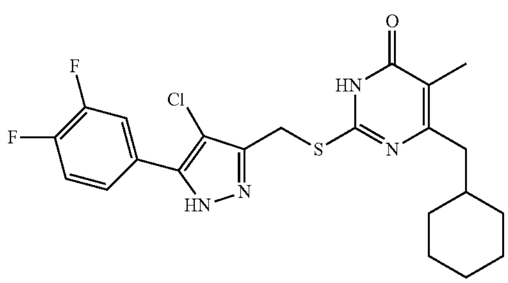 [SMILES: Cc1c(CC2CCCCC2)nc(SCc2n[nH]c(-c3ccc(F)c(F)c3)c2Cl)[nH]c1=O] |
| I-57 | 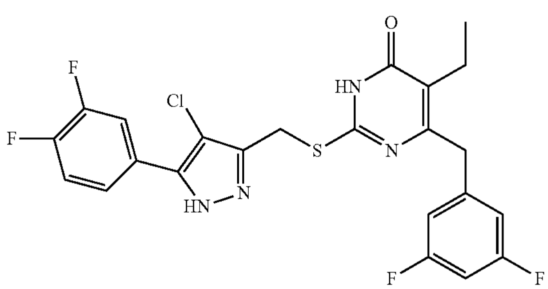 [SMILES: CCc1c(Cc2cc(F)cc(F)c2)nc(SCc2n[nH]c(-c3ccc(F)c(F)c3)c2Cl)[nH]c1=O] |
| I-58 | 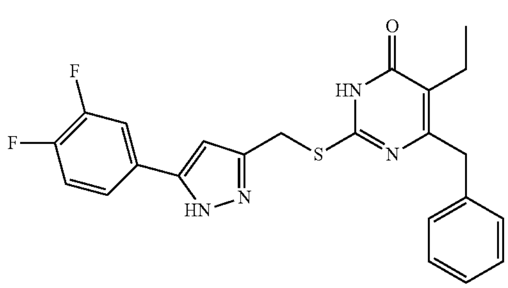 [SMILES: CCc1c(Cc2ccccc2)nc(SCc2cc(-c3ccc(F)c(F)c3)[nH]n2)[nH]c1=O] |

-continued
| Compound | Structure |
|---|---|
| I-59 | 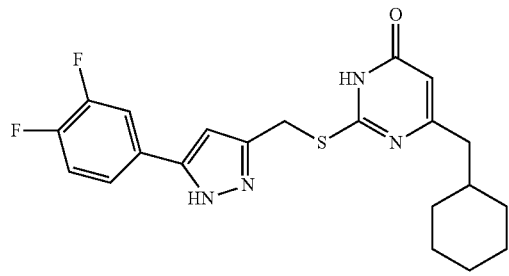 [SMILES: O=c1cc(CC2CCCCC2)nc(SCc2cc(-c3ccc(F)c(F)c3)[nH]n2)[nH]1] |
| I-60 | 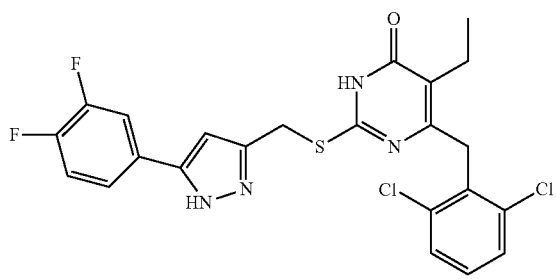 [SMILES: CCc1c(Cc2c(Cl)cccc2Cl)nc(SCc2cc(-c3ccc(F)c(F)c3)[nH]n2)[nH]c1=O] |
| I-61 | 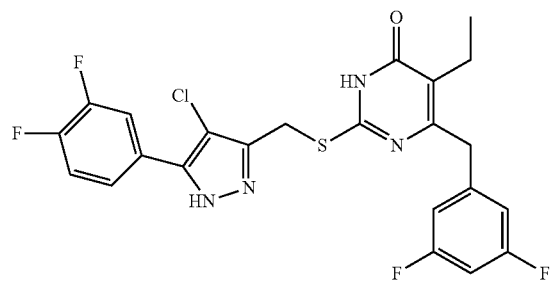 [SMILES: CCc1c(Cc2cc(F)cc(F)c2)nc(SCc2n[nH]c(-c3ccc(F)c(F)c3)c2Cl)[nH]c1=O] |
| I-62 | 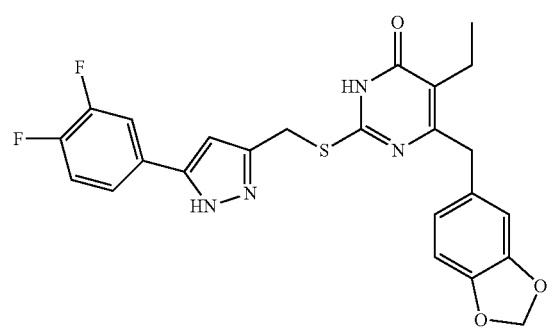 [SMILES: CCc1c(Cc2ccc3c(c2)OCO3)nc(SCc2cc(-c3ccc(F)c(F)c3)[nH]n2)[nH]c1=O] |
| I-63 | 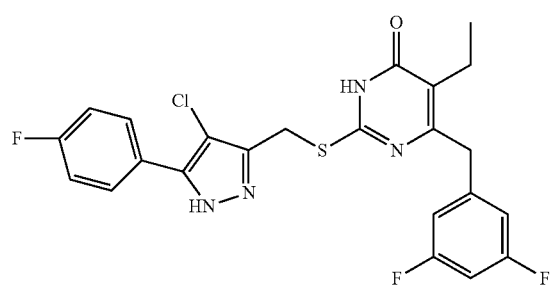 |

-continued
| Compound | Structure |
|---|---|
| I-64 | 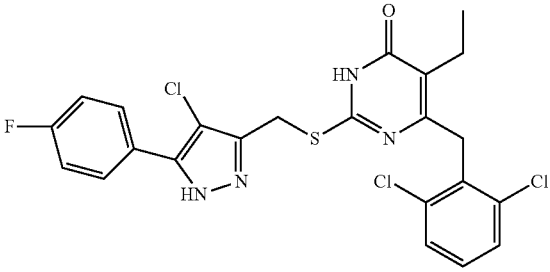 [SMILES: CCc1c(Cc2c(Cl)cccc2Cl)nc(SCc2n[nH]c(-c3ccc(F)cc3)c2Cl)[nH]c1=O] |
| I-65 | 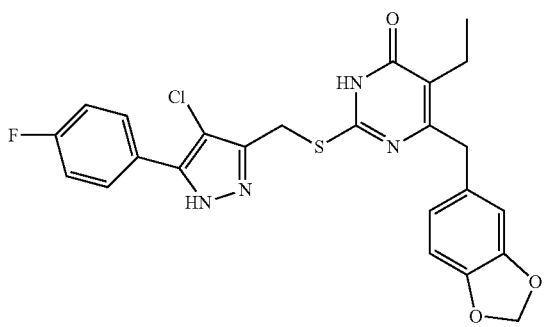 [SMILES: CCc1c(Cc2ccc3c(c2)OCO3)nc(SCc2n[nH]c(-c3ccc(F)cc3)c2Cl)[nH]c1=O] |
| I-66 | 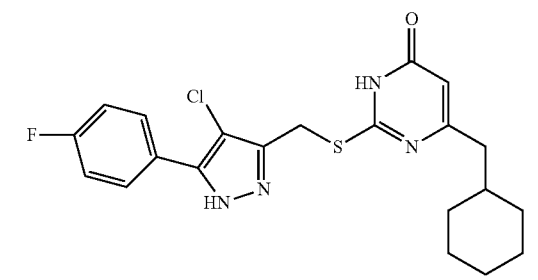 [SMILES: O=c1cc(CC2CCCCC2)nc(SCc2n[nH]c(-c3ccc(F)cc3)c2Cl)[nH]1] |
| I-67 | 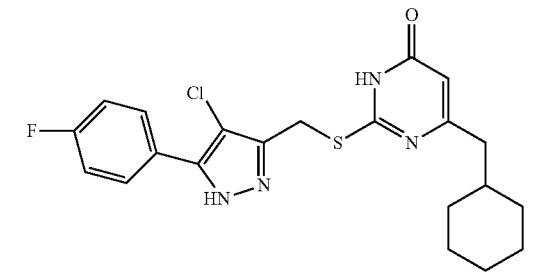 [SMILES: O=c1cc(CC2CCCCC2)nc(SCc2n[nH]c(-c3ccc(F)cc3)c2Cl)[nH]1] |
| I-68 | 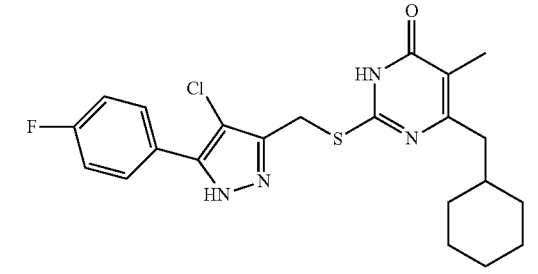 [SMILES: Cc1c(CC2CCCCC2)nc(SCc2n[nH]c(-c3ccc(F)cc3)c2Cl)[nH]c1=O] |

-continued
| Compound | Structure |
|---|---|
| I-69 | 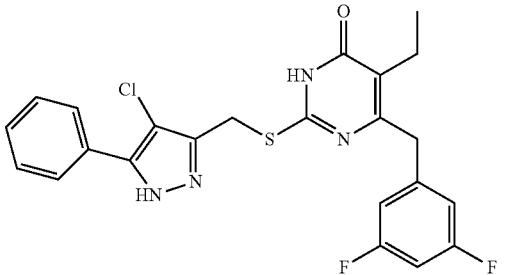 [SMILES: CCc1c(Cc2cc(F)cc(F)c2)nc(SCc2n[nH]c(-c3ccccc3)c2Cl)[nH]c1=O] |
| I-70 | 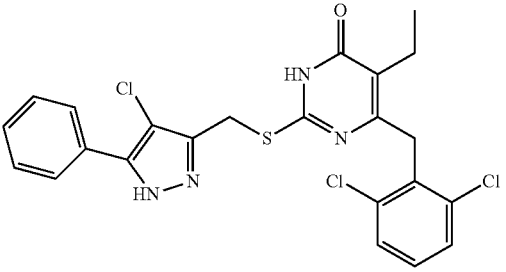 [SMILES: CCc1c(Cc2c(Cl)cccc2Cl)nc(SCc2n[nH]c(-c3ccccc3)c2Cl)[nH]c1=O] |
| I-71 | 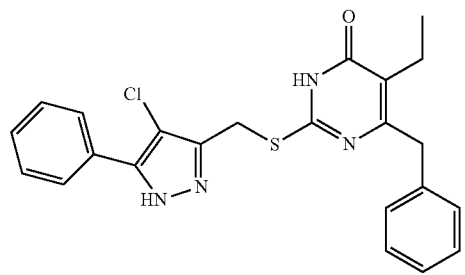 [SMILES: CCc1c(Cc2ccccc2)nc(SCc2n[nH]c(-c3ccccc3)c2Cl)[nH]c1=O] |
| I-72 | 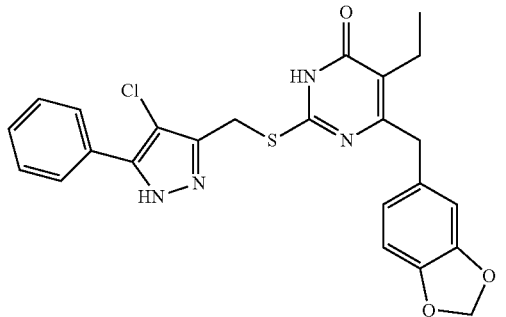 [SMILES: CCc1c(Cc2ccc3c(c2)OCO3)nc(SCc2n[nH]c(-c3ccccc3)c2Cl)[nH]c1=O] |
In the present disclosure, the compound represented by formula I is preferably any one of the following compounds:
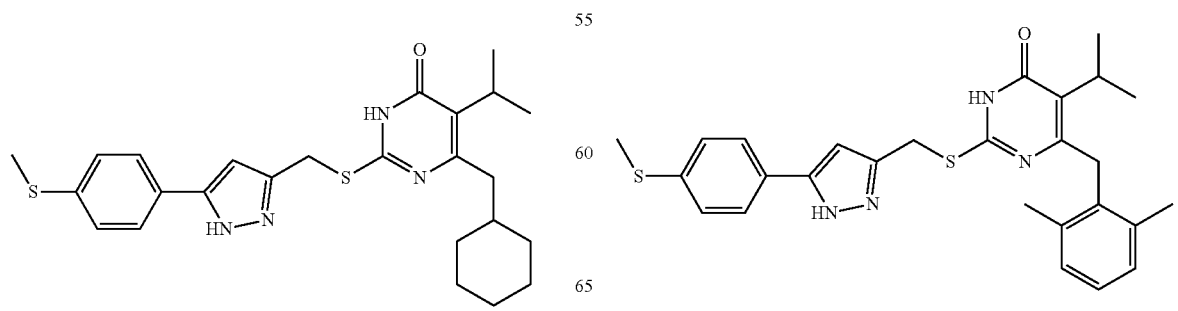
-continued

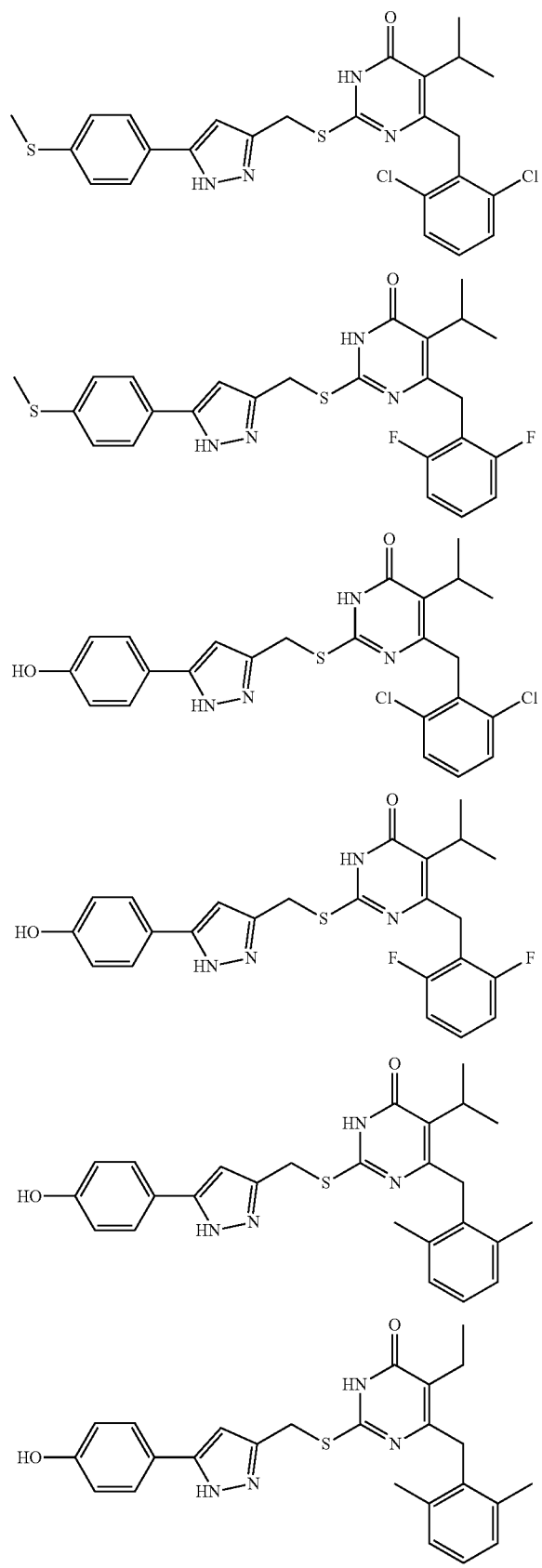

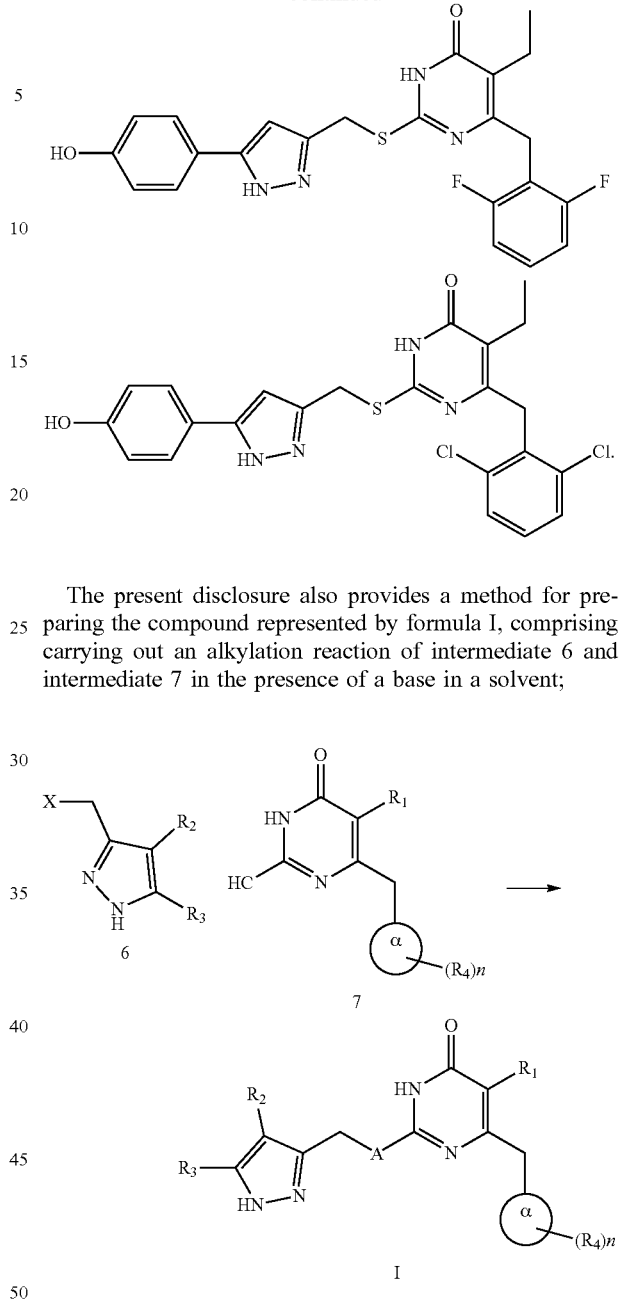

The present disclosure also provides a method for preparing the compound represented by formula I, comprising carrying out an alkylation reaction of intermediate 6 and intermediate 7 in the presence of a base in a solvent;

wherein the definitions of A, n, $R_1$, $R_2$, $R_3$, $R_4$ and α ring are as defined above, X is halogen.

In the present disclosure, the alkylation reaction occurs in accordance with the mechanism of this type of alkylation reaction in the art, and conventional conditions and parameters for this type of alkylation reaction in the art can be employed.

In the present disclosure, X is preferably fluorine, chlorine, bromine or iodine, further preferably chlorine.

In the present disclosure, the solvent can be a conventional solvent for this type of reaction in the art, which does not participate in or interfere with the reaction, and the solvent is preferably one or more selected from DMF, THF, $CH_3CN$, dioxane and pyridine, more preferably DMF.

In the present disclosure, the amount of the solvent can be a conventional amount for this type of reaction in the art, which is sufficient for completely dissolving the reactants and ensuring the smooth progress of the reaction.

In the present disclosure, the base can be a conventional base for this type of reaction in the art, which is preferably one or more selected from DMAP, $Cs_2CO_3$, $K_2CO_3$, $Na_2CO_3$, NaH and $Et_3N$, further preferably $K_2CO_3$.

In the present disclosure, the amount of the base can be a conventional amount for this type of reaction in the art, and the molar ratio of the intermediate 6 to the base is preferably 1:1 to 1:2, e.g., 3:4.

In the present disclosure, the molar ratio of the intermediate 6 to the intermediate 7 can be a conventional ratio for this type of reaction in the art, which is preferably 1:1 to 1:1.2.

In the present disclosure, the reaction temperature of the alkylation reaction can be a conventional temperature for this type of reaction in the art, which is preferably controlled between 20 and 80° C., e.g., room temperature (20 to 25° C.).

In the present disclosure, the progress of the alkylation reaction can be monitored by conventional detection methods in the art (e.g., TLC, HPLC or NMR), and the point where a raw material disappears or does not proceed to react is generally seen as completion of the reaction. The duration of the alkylation reaction is preferably 3 to 24 hours, more preferably 8 to 12 hours.

In the present disclosure, the method for preparing the compound represented by formula I preferably comprises dissolving the intermediate 7 in part of the solvent, adding the base, then adding a solution of the intermediate 6 in the remaining part of the solvent after stirring, and reacting under continuous stirring.

In the present disclosure, after the completion of the alkylation reaction, the method for preparing the compound represented by formula I preferably comprises a post-treatment step comprising pouring the reaction solution into ice water, during which a white solid precipitates out; obtaining a crude product by filtering or extracting with ethyl acetate; purifying the crude product by column chromatography or recrystallization to obtain a pure product of the target compound. Wherein, the developing solvent for the column chromatography is preferably a mixed solvent of ethyl acetate and petroleum ether, e.g., ethyl acetate/petroleum ether=1:4 (v/v).

In the present disclosure, when α ring is cyclohexyl, then the intermediate 7 can be prepared by a method well known to those skilled in the organic chemistry field, Yan-Ping He, Jin Long, et al., *Bioorg. & Med. Chem.* 2011, 21, 694-697, third paragraph on page 695 can be referred to for details (the contents of this reference are incorporated herein by reference), specific synthetic routes are shown below:

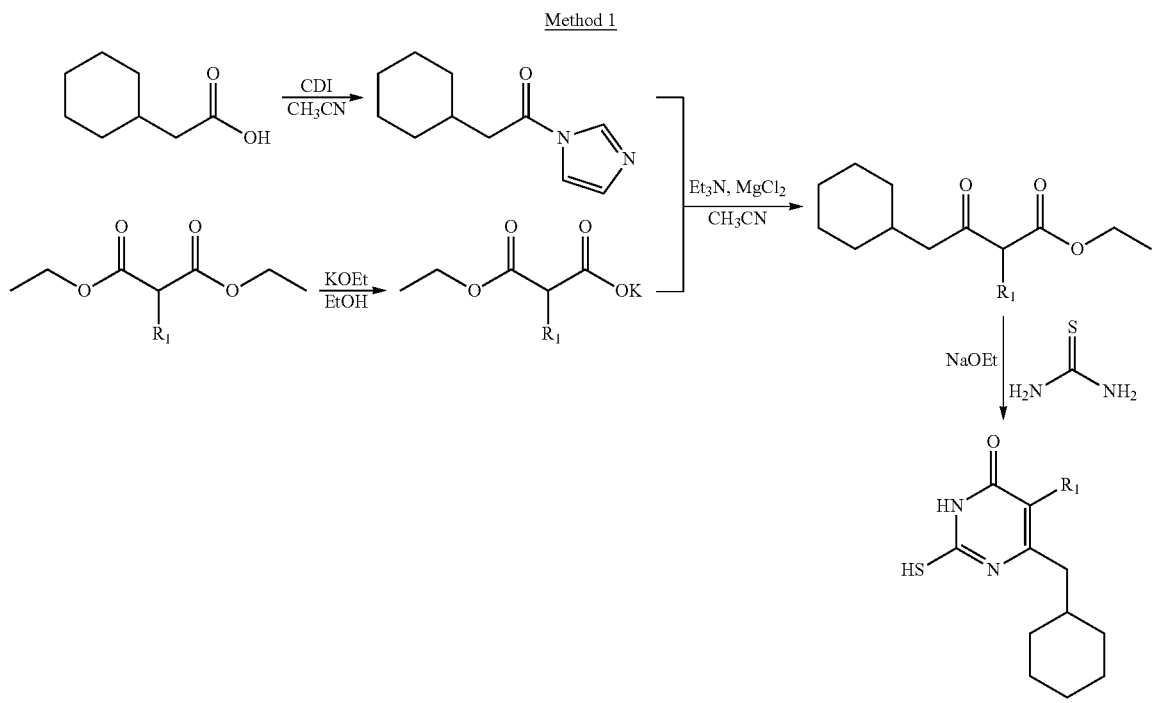

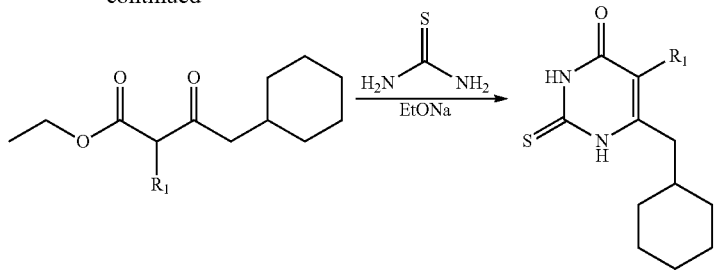

wherein the definition of $R_1$ is as defined above.

In the present disclosure, when α ring is phenyl substituted by n $R_4$ where each $R_4$ is the same or different, then the intermediate 7 can be prepared by a method well known to those skilled in the organic chemistry field, Maxim B. Nawrozkij, Dante Rotili, et al. *J. Med. Chem.* 2008, 51, 4641-4652 can be referred to for details (the contents of this reference are incorporated herein by reference), specific synthetic routes are shown below:

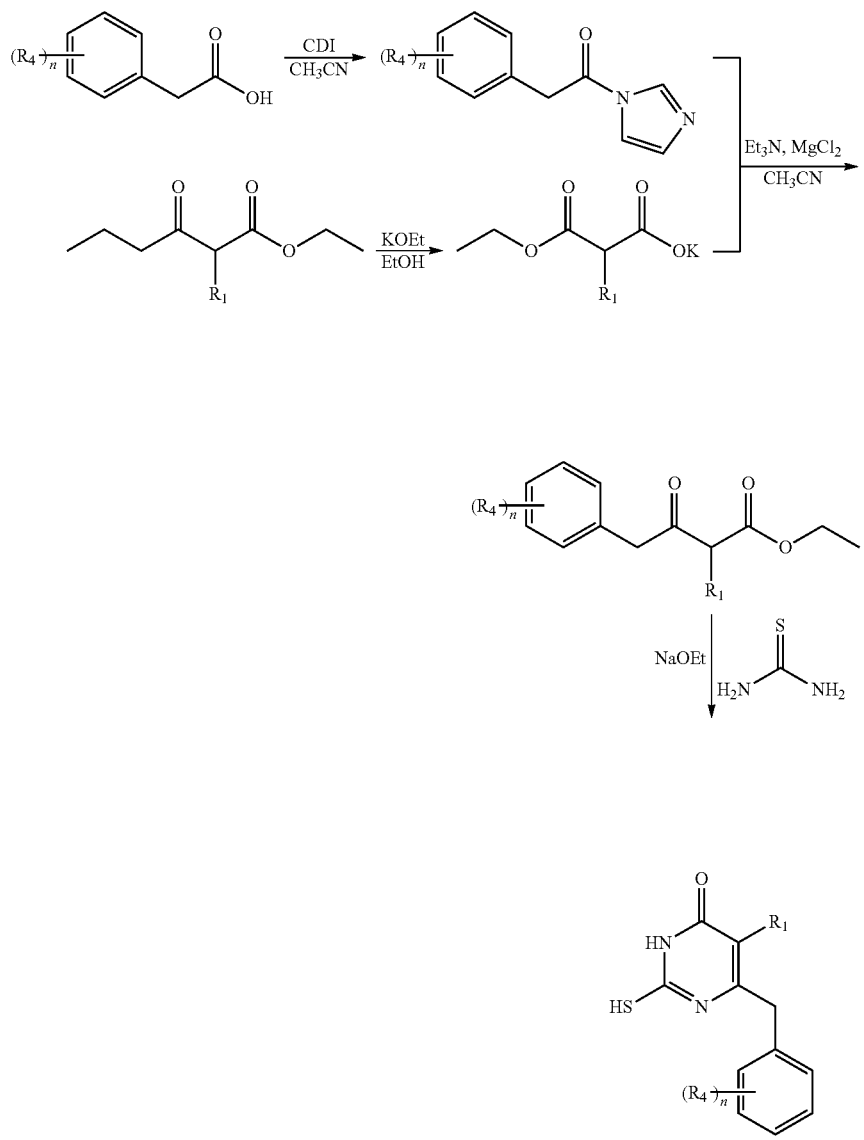

wherein the definitions of $R_1$, $R_4$ and n are as defined above.

In the present disclosure, the compound represented by formula I preferably further comprises carrying out a halogenation reaction of intermediate 5 with a halogenating agent in a solvent to obtain the intermediate 6;

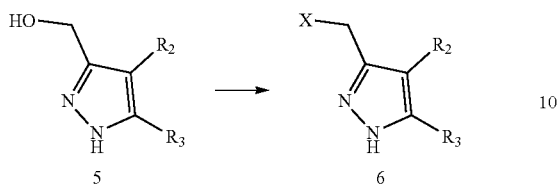

wherein the definitions of $R_2$ and $R_3$ are as defined above, X is halogen.

In the present disclosure, the halogenation reaction occurs in accordance with the mechanism of this type of halogenation reaction in the art, and conventional conditions and parameters for this type of halogenation reaction in the art can be employed.

In the present disclosure, X is preferably fluorine, chlorine, bromine or iodine, further preferably chlorine.

In the present disclosure, the solvent can be a conventional solvent for this type of reaction in the art, which does not participate in or interfere with the reaction, and the solvent is preferably one or more selected from THF, $CH_3CN$, dioxane and pyridine, further preferably $CH_3CN$.

In the present disclosure, the amount of the solvent can be a conventional amount for this type of reaction in the art, which is sufficient for completely dissolving the reactants and ensuring the smooth progress of the reaction.

In the present disclosure, the halogenating agent can be a conventional halogenating agent for this type of reaction in the art, which is preferably one or more selected from $Br_2$, $PBr_3$, $CBr_4$, NBS, NCS, $POCl_3$ and $I_2$, further preferably $PBr_3$.

In the present disclosure, the amount of the halogenating agent can be a conventional amount for this type of reaction in the art, and the molar ratio of the intermediate 5 to the halogenating agent is preferably 1:1 to 1:2, e.g., 1:1.2.

In the present disclosure, the reaction temperature of the halogenation reaction can be a conventional temperature for this type of reaction in the art, which is preferably controlled between 0 and 85° C., e.g., 70 to 85° C.

In the present disclosure, the progress of the halogenation reaction can be monitored by conventional detection methods in the art (e.g., TLC, HPLC or NMR), and the point where a raw material disappears or does not proceed to react is generally seen as completion of the reaction. The duration of the halogenation reaction is preferably 8 to 24 hours, more preferably 0.5 to 3 hours.

In the present disclosure, the method for preparing the compound represented by formula I preferably comprises dissolving the intermediate 5 in the solvent, adding the halogenating agent dropwise under an ice bath; proceeding with the halogenation reaction under stirring after completion of the dropwise addition.

In the present disclosure, after completion of the halogenation reaction, the method for preparing the compound represented by formula I preferably comprises a post-treatment step comprising pouring the reaction solution into ice water, removing the solvent under reduced pressure, adjusting the pH to weakly alkaline with saturated $NaHCO_3$, filtering by suction, extracting the filtrate with ethyl acetate, combining the organic phases, washing the combined organic phase with saturated brine and drying over anhydrous sodium sulfate, concentrating under reduced pressure and recrystallizing to obtain the intermediate 6. Wherein, the recrystallizing is preferably performed with ethyl acetate/petroleum ether (1:3, v/v).

In the present disclosure, the compound represented by formula I preferably further comprises carrying out a reduction reaction of intermediate 4 in the presence of a reducing agent in a solvent to obtain the intermediate 5;

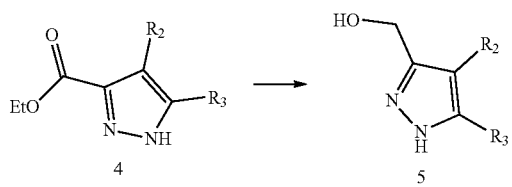

wherein the definitions of $R_2$ and $R_3$ are as defined above.

In the present disclosure, the reduction reaction occurs in accordance with the mechanism of this type of reduction reaction in the art, and conventional conditions and parameters for this type of reduction reaction in the art can be employed.

In the present disclosure, the reduction reaction is preferably carried out under the protection of an inert gas such as nitrogen.

In the present disclosure, the solvent can be a conventional solvent for this type of reaction in the art, which does not participate in or interfere with the reaction, and the solvent is preferably one or more selected from $CH_3CN$, THF, DMF, DMSO and dioxane, more preferably the solvent is subjected to water removal treatment before use.

In the present disclosure, the amount of the solvent can be a conventional amount for this type of reaction in the art, which is sufficient for completely dissolving the reactants and ensuring the smooth progress of the reaction.

In the present disclosure, the reducing agent can be a conventional reducing agent for this type of reaction in the art, which is preferably one or more selected from $NaBH_4$, $LiAlH_4$ and $KBH_4$, further preferably $LiAlH_4$.

In the present disclosure, the amount of the reducing agent can be a conventional amount for this type of reaction in the art, and the molar ratio of the intermediate 4 to the reducing agent is preferably 1:1 to 1:2, e.g., 1:1.5.

In the present disclosure, the reaction temperature of the reduction reaction can be a conventional temperature for this type of reaction in the art, which is preferably controlled between 0 and 45° C., further preferably room temperature.

In the present disclosure, the progress of the reduction reaction can be monitored by conventional detection methods in the art (e.g., TLC, HPLC or NMR), and the point where a raw material disappears or does not proceed to react is generally seen as completion of the reaction. The duration of the reduction reaction is preferably 2 to 12 hours.

In the present disclosure, the method for preparing the compound represented by formula I preferably comprises adding the reducing agent in batches into a mixture of the intermediate 4 and the solvent under an ice bath and nitrogen protection, proceeding with the reduction reaction under stirring after the addition.

In the present disclosure, after completion of the reduction reaction, the method for preparing the compound represented by formula I preferably comprises a post-treatment step comprising adding saturated aqueous ammonium chloride solution dropwise to the reaction solution under an ice bath to quench the reaction, filtering, extracting the filtrate with ethyl acetate, combining the organic phases, washing the combined organic phase with saturated brine, drying over anhydrous sodium sulfate, concentrating under reduced pressure and recrystallizing to obtain the intermediate 5. Wherein, the recrystallizing is preferably performed with ethyl acetate/petroleum ether (1:3, v/v).

In the present disclosure, the compound represented by formula I preferably further comprises carrying out a halogenation reaction of intermediate 3 with a halogenating agent in a solvent to obtain the intermediate 4;

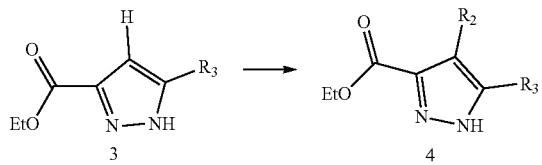

wherein the definitions of $R_2$ and $R_3$ are as defined above.

In the present disclosure, the halogenation reaction occurs in accordance with the mechanism of this type of halogenation reaction in the art, and conventional conditions and parameters for this type of halogenation reaction in the art can be employed.

In the present disclosure, the solvent can be a conventional solvent for this type of reaction in the art, which does not participate in or interfere with the reaction, and the solvent is preferably one or more selected from $CH_3CN$, THF, DMF and dioxane.

In the present disclosure, the amount of the solvent can be a conventional amount for this type of reaction in the art, which is sufficient for completely dissolving the reactants and ensuring the smooth progress of the reaction.

In the present disclosure, the halogenating agent can be a conventional halogenating agent for this type of reaction in the art, which is preferably one or more selected from NBS, NCS and NIS.

In the present disclosure, the amount of the halogenating agent can be a conventional amount for this type of reaction in the art, and the molar ratio of the intermediate 3 to the halogenating agent is preferably 1:1 to 1:6, e.g., 1:1.2.

In the present disclosure, the reaction temperature of the halogenation reaction can be a conventional temperature for this type of reaction in the art, which is preferably controlled between 40 and 80° C., e.g., 60° C.

In the present disclosure, the progress of the halogenation reaction can be monitored by conventional detection methods in the art (e.g., TLC, HPLC or NMR), and the point where a raw material disappears or does not proceed to react is generally seen as completion of the reaction. The duration of the halogenation reaction is preferably 8 to 24 hours, more preferably 10 to 15 hours.

In the present disclosure, the method for preparing the compound represented by formula I preferably comprises dissolving the intermediate 3 in the solvent, adding the halogenating agent at room temperature, proceeding with the halogenation reaction under stirring after completion of the dropwise addition.

In the present disclosure, after completion of the halogenation reaction, the method for preparing the compound represented by formula I preferably comprises a post-treatment step comprising removing the solvent under reduced pressure, extracting with ethyl acetate, combining the organic phases, washing the organic phases with saturated brine and drying over anhydrous sodium sulfate, concentrating under reduced pressure, and purifying the crude product by column chromatography to obtain the intermediate 4. The eluent for the column chromatography is preferably ethyl acetate/petroleum ether (1:4, v/v).

In the present disclosure, the compound represented by formula I preferably further comprises carrying out a condensation reaction of intermediate 2 with hydrazine hydrate in a solvent to obtain the intermediate 3;

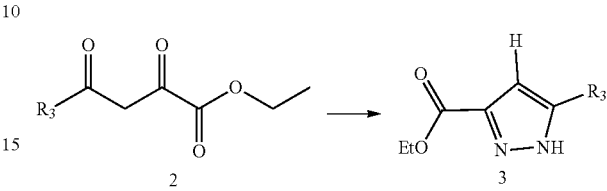

wherein the definition of $R_3$ is as defined above.

In the present disclosure, the condensation reaction occurs in accordance with the mechanism of this type of condensation reaction in the art, and conventional conditions and parameters for this type of condensation reaction in the art can be employed.

In the present disclosure, the solvent can be a conventional solvent for this type of reaction in the art, which does not participate in or interfere with the reaction, and the solvent is preferably one or more selected from MeOH, EtOH, THF, dioxane, $CH_3CN$ and $H_2O$, further preferably EtOH.

In the present disclosure, the amount of the solvent can be a conventional amount for this type of reaction in the art, which is sufficient for completely dissolving the reactants and ensuring the smooth progress of the reaction.

In the present disclosure, the amount of the hydrazine hydrate can be a conventional amount for this type of reaction in the art, and the molar ratio of the intermediate 2 to the hydrazine hydrate is preferably 1:1 to 1:2.

In the present disclosure, the reaction temperature of the condensation reaction can be a conventional temperature for this type of reaction in the art, which is preferably controlled between 30 and 85° C.

In the present disclosure, the progress of the condensation reaction can be monitored by conventional detection methods in the art (e.g., TLC, HPLC or NMR), and the point where a raw material disappears or does not proceed to react is generally seen as completion of the reaction. The duration of the condensation reaction is preferably 3 to 24 hours.

In the present disclosure, the method for preparing the compound represented by formula I preferably comprises adding the hydrazine hydrate dropwise into a mixture of the intermediate 2 and the solvent at room temperature, proceeding with the condensation reaction under stirring and refluxing after the completion of the dropwise addition.

In the present disclosure, after completion of the condensation reaction, the method for preparing the compound represented by formula I preferably comprises a post-treatment step comprising cooling the reaction solution to room temperature, removing the solvent, extracting with water and ethyl acetate, combining the organic phases, washing the combined organic phase with saturated brine and drying over anhydrous sodium sulfate, concentrating and recrystallizing to obtain the intermediate 3. Wherein, the recrystallizing is preferably performed with ethyl acetate/petroleum ether (1:5, v/v).

In the present disclosure, the compound represented by formula I preferably further comprises carrying out a nucleophilic substitution reaction of intermediate 1 with diethyl oxalate in the presence of a base in a solvent to obtain the intermediate 2;

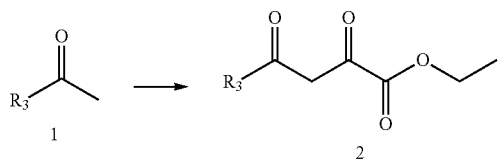

wherein the definition of R₃ is as defined above.

In the present disclosure, the nucleophilic substitution reaction occurs in accordance with the mechanism of this type of nucleophilic substitution reaction in the art, and conventional conditions and parameters for this type of nucleophilic substitution reaction in the art can be employed.

In the present disclosure, the solvent can be a conventional solvent for this type of reaction in the art, which does not participate in or interfere with the reaction, and the solvent is preferably one or more selected from MeOH, EtOH, THF, CH₃CN, dioxane and toluene, further preferably EtOH.

In the present disclosure, the amount of the solvent can be a conventional amount for this type of reaction in the art, which is sufficient for completely dissolving the reactants and ensuring the smooth progress of the reaction.

In the present disclosure, the base can be a conventional base for this type of reaction in the art, which is preferably one or more selected from DMAP, Cs₂CO₃, K₂CO₃, C₂H₅ONa, CH₃ONa, Na₂CO₃, NaHCO₃ and Et₃N, further preferably C₂HONa.

In the present disclosure, when the base is C₂HONa, the C₂H₅ONa can be produced in situ using sodium metal and ethanol.

In the present disclosure, the amount of the base can be a conventional amount for this type of reaction in the art, and the molar ratio of the intermediate 1 to the base is preferably 1:1 to 1:2.

In the present disclosure, the amount of the diethyl oxalate can be a conventional amount for this type of reaction in the art, and the molar ratio of the intermediate 1 to the diethyl oxalate is preferably 1:1 to 1:2.

In the present disclosure, the reaction temperature of the nucleophilic substitution reaction can be a conventional temperature for this type of reaction in the art, which is preferably controlled between 20 and 80° C., e.g., room temperature.

In the present disclosure, the progress of the nucleophilic substitution reaction can be monitored by conventional detection methods in the art (e.g., TLC, HPLC or NMR), and the point where a raw material disappears or does not proceed to react is generally seen as completion of the reaction. The duration of the nucleophilic substitution reaction is preferably 3 to 24 hours, e.g., 8 hours.

In the present disclosure, the method for preparing the compound represented by formula I preferably comprises adding the diethyl oxalate to a mixture of the intermediate 1, the base and the solvent, and reacting at room temperature.

In the present disclosure, after completion of the nucleophilic substitution reaction, the method for preparing the compound represented by formula I preferably comprises a post-treatment step comprising adjusting the pH of the reaction solution to 8 by addition of dilute hydrochloric acid, evaporating the solvent, extracting with water and ethyl acetate, combining the organic phases, washing the combined organic phase with saturated brine, drying over anhydrous sodium sulfate, filtering and concentrating.

In the present disclosure, the method for preparing the compound represented by formula I preferably employs the following synthetic route:

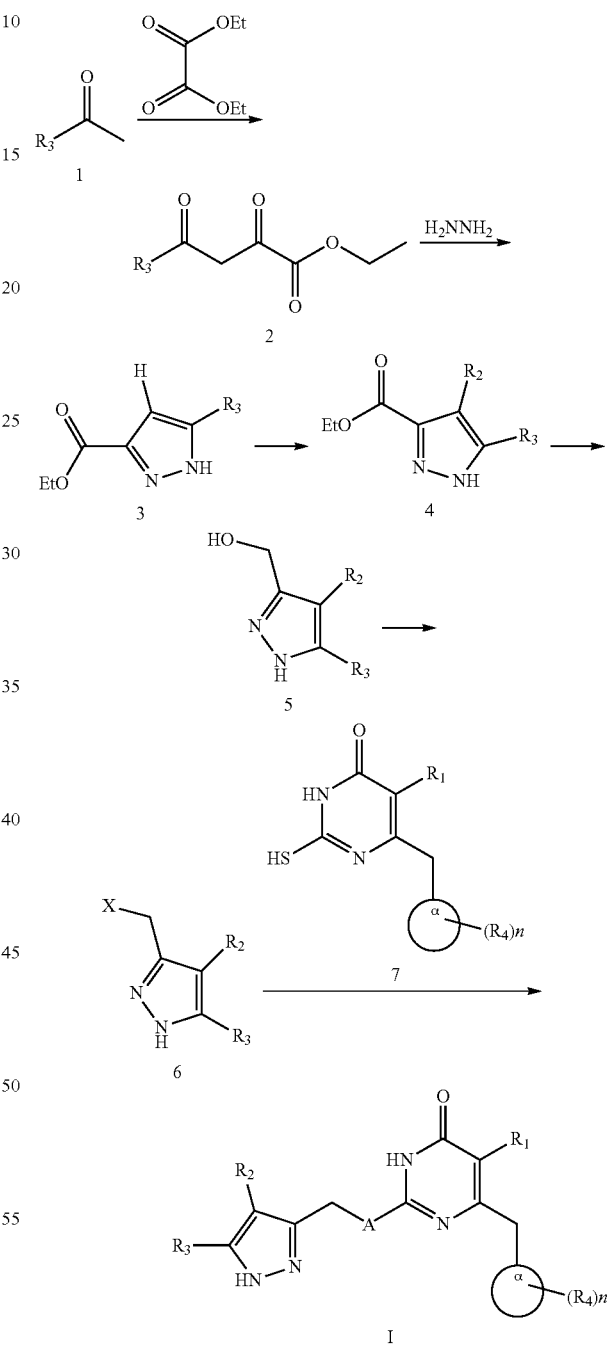

wherein the definitions of n, R₁, R₂, R₃, R₄, α ring and X are as defined above, the specific reaction conditions and parameters for each reaction of each step are as described above.

According to the preparation method described above, those skilled in the art can employ the same principle and method to prepare each specific compound involved in the compound represented by formula I of the present disclosure.

The present disclosure also provides a use of the compound represented by formula I, or the N-oxide, tautomer, optical isomer, hydrate, solvate, polymorph, pharmaceutically acceptable salt thereof or the prodrug thereof as a non-nucleoside HIV-1 inhibitor, and the non-nucleoside HIV-1 inhibitor is preferably a non-nucleoside HIV-1$_{IIIB}$ inhibitor.

The present disclosure also provides a use of the compound represented by formula I, or the N-oxide, tautomer, optical isomer, hydrate, solvate, polymorph, pharmaceutically acceptable salt thereof or the prodrug thereof in the manufacture of an anti-HIV-1 medicament.

The present disclosure also provides a use of the compound represented by formula I, or the N-oxide, tautomer, optical isomer, hydrate, solvate, polymorph, pharmaceutically acceptable salt thereof or the prodrug thereof in the manufacture of a medicament for treating and/or preventing human immunodeficiency virus (HIV) infection.

The present disclosure also provides a pharmaceutical composition comprising a therapeutically effective amount of the compound represented by formula I, or the N-oxide, tautomer, optical isomer, hydrate, solvate, polymorph, pharmaceutically acceptable salt thereof or the prodrug thereof, and at least one pharmaceutical excipient. The mass percentage of the compound represented by formula I, or the N-oxide, tautomer, optical isomer, hydrate, solvate, polymorph, pharmaceutically acceptable salt thereof or the prodrug thereof in the pharmaceutical composition is 0.1% to 99.9%, and the mass percentage refers to the mass of the compound represented by formula I, or the N-oxide, tautomer, optical isomer, hydrate, solvate, polymorph, pharmaceutically acceptable salt thereof or the prodrug thereof in the total mass of pharmaceutical composition. The sum of the mass fractions of the compound represented by formula I, or the N-oxide, tautomer, optical isomer, hydrate, solvate, polymorph, pharmaceutically acceptable salt thereof or the prodrug thereof and the pharmaceutical excipient is 100%. The selection of the pharmaceutical excipient varies with the route of administration and the characteristics of the action, and is generally a filler, a diluent, a binder, a wetting agent, a disintegrant, a lubricant, an emulsifier or a suspending agent.

The present disclosure also provides a method for treating human immunodeficiency virus (HIV) infection disease, wherein the method comprises administering a therapeutically effective amount of the compound represented by formula I, or the N-oxide, tautomer, optical isomer, hydrate, solvate, polymorph, pharmaceutically acceptable salt thereof or the prodrug thereof to a subject in need thereof.

Unless otherwise specified, the following terms employed in the description and the claims of the present disclosure have the following meanings.

The term "pharmaceutically acceptable salt" refers to a salt of the compound of the present disclosure which is prepared by reacting the compound of the present disclosure having a specific substituent with a relatively non-toxic acid or base. When the compound of the present disclosure contains a relatively acidic functional group, a base addition salt can be obtained by contacting the neutral form of the compound with a sufficient amount of a base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by contacting the neutral form of the compound with a sufficient amount of an acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, etc.; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzene sulfonic acid, p-toluenesulfonic acid, citric acid, tartaric acid, and methanesulfonic acid, etc.; and an salt of amino acid (e.g., arginine), and a salt of an organic acid such as glucuronic acid (referring to Berge et al., "Pharmaceutical Salts", *Journal of Pharmaceutical Science* 66: 1-19 (1977), the content of which is incorporated herein by reference in its entirety). Certain specific compounds of the present disclosure which contain both basic and acidic functional groups can be converted to any base or acid addition salt.

Preferably, through contacting a salt with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present disclosure, wherein the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present disclosure can be prepared from the parent compound which contains an acidic or basic moiety by conventional chemical methods. Generally, such salt can be prepared by reacting the free acid or base form of the compound with a stoichiometric amount of an appropriate base or acid in water or an organic solvent or a mixture thereof. Generally, anon-aqueous medium, e.g., an ether, ethyl acetate, ethanol, isopropanol or acetonitrile, is preferred.

In addition to the salt form, the compound provided by the present disclosure also exists in the prodrug form. The prodrug of the compound described herein is a compound that readily undergoes chemical change under physiological condition to be converted into the compound of the present disclosure. Additionally, the prodrug can be converted to the compound of the present disclosure by a chemical or biochemical method in vivo environment.

Some compounds of the present disclosure can exist in unsolvated or solvated form, including hydrated form. Generally speaking, the solvated form is equivalent to the unsolvated form, and both are included within the scope of the present disclosure. Some compounds of the present disclosure can exist in the polymorphous form or amorphous form.

The term "pharmaceutically acceptable carrier" refers to a carrier for any preparation or carrier medium which can deliver an effective amount of the active substances of the present disclosure, does not interfere with the biological activity of the active substances and has no toxic side effects on hosts or patients, representative carries includes water, oil, vegetable and mineral, paste, lotion matrix, ointment matrix, etc. These matrices include suspensions, tackifiers, penetration enhancers, etc. Their preparations are well known to those skilled in the art of cosmetics or topical pharmaceuticals. For other information about carriers, *Remington: The Science and Practice of Pharmacy*, 21st Ed., Lippincott, Williams & Wilkins (2005), which is incorporated herein by reference, can be referred to.

The term "excipient" usually refers to a carrier, a diluent and/or a medium required for the preparation of an effective pharmaceutical composition.

For pharmaceuticals or pharmacological active agents, the term "effective amount" or "therapeutic effective amount" refers to an amount of a drug or medicament that is non-toxic but is sufficient to achieve the desired effect. For the oral dosage form in the present disclosure, the "effective amount" of an active substance in the composition refers to an amount required to achieve the desired effect when combined with another active substance in the composition. The determination of the effective amount varies from person to person, depending on age and general condition of a receptor, and also on a specific active substance. The appropriate effective amount in a case can be determined by those skilled in the art according to routine experiments.

Some compounds of the present disclosure can contain asymmetric carbon atoms (optical center) or double bonds. Racemic isomers, diastereomers, geometric isomers and single isomers are all encompassed within the scope of the present disclosure.

The compound of the present disclosure can have a specific geometric or stereoisomeric form. The present disclosure contemplates all of such compounds, including cis and trans isomers, (−)- and (+)-enantiomers, (R)- and (S)-enantiomers, diastereoisomers, (D)-isomers, (L)-isomers, and racemic mixtures and other mixtures, for example, enantiomer or diastereoisomer enriched mixtures, are encompassed within the scope of the present disclosure. Substituents such as alkyl can have an additional asymmetric carbon atom. All these isomers and mixtures thereof are encompassed within the scope of the present disclosure.

The diagrammatic representation of racemic isomer, ambiscalemic and scalemic or enantiopure compound of the present disclosure is from Maehr, *J. Chem. Ed.* 1985, 62: 114-120, which is incorporated herein by reference. Unless otherwise indicated, the absolute configuration of a stereocenter is represented by wedged and dashed lines. When the compound of the present disclosure contains a vinyl double bond or other geometric asymmetric center, unless otherwise specified, E, Z geometric isomers are included. Similarly, all tautomeric forms are encompassed within the scope of the present disclosure.

The chemical general formula involved in the present disclosure can exhibit tautomerism, structural isomerism and stereoisomerism. The present disclosure includes any tautomeric or structural isomeric or stereoisomeric form and a mixture thereof, and they have the ability to modulate kinase activity which is not limited to any form of the isomer or the mixture thereof.

Optically active (R)- and -isomers, (D)- and (L)-isomers can be prepared by chiral synthesis or chiral reagents or other conventional techniques. If an enantiomer of a compound of the present disclosure is desired, asymmetric synthesis or derivatization action of the chiral auxiliaries can be employed in preparation, in which the resulting diastereomer mixtures are isolated, and the auxiliary groups are cleaved to provide the pure desired enantiomer. Alternatively, when a molecule contains a basic functional group (e.g., amino) or an acidic functional group (e.g., carboxyl), a salt of a diastereomer is formed with an appropriate optical active acid or base, and then the pure enantiomer can be recycled after resolution on the salt of diastereomer by methods well known in the art. In addition, the isolation of an enantiomer and a diastereomer is usually realized by a chromatographic method, the chromatography method employs a chiral stationary phase, optionally in combination with a chemical derivatization method (e.g., an amine generates a carbamate).

One or more atoms constituting the compound of the present disclosure can comprise an unnatural proportion of atomic isotopes. For example, the compound can be labeled by a radioactive isotope, e.g., tritium ($^3$H), iodine-125 ($^{125}$I) or C-14 ($^{14}$C). All of these variations in the isotopic composition of the compound of the present disclosure, whether radioactive or not, are encompassed within the scope of the present disclosure.

Unless otherwise specified, the reagents and raw materials used in the present disclosure are commercially available.

Unless otherwise specified, compounds are named manually or by ChemDraw® software, commercially available compounds use their vendor directory names.

The above-mentioned preferred conditions can be arbitrarily combined to obtain preferred embodiments of the present disclosure in accordance with common knowledge in the art.

The advantageous effect of the present disclosure is that the present disclosure provides a novel pyrimidinone-containing compound, and a preparation method, pharmaceutical composition and use thereof. Tests have proved that the compound of the present disclosure can be used as a HIV-1 inhibitor and has high use value. Specifically, the compound can be used in the manufacture of an anti-AIDS medicament.

DETAILED DESCRIPTION OF THE EMBODIMENT

The following describes the present disclosure in detail with embodiments, but it does not impose any adverse limitation on the present disclosure. The present disclosure has been described in detail herein, and its specific embodiments are also disclosed. It is obvious to those skilled in the art that various changes and improvements can be made to the specific embodiments of the present disclosure without departing from the spirit and scope of the present disclosure.

The experimental methods which are not specified in the following embodiments are selected according to conventional methods and conditions, or according to product specifications. The raw materials can be obtained from commercial sources, or prepared by methods known in the art, or prepared according to the methods described herein.

The structures of the compounds were determined by nuclear magnetic resonance ($^1$H NMR or $^{13}$C NMR) or mass spectrometry (MS), wherein NMR was measured by Bruker AV-300 type nuclear magnetic resonance spectrometer with deuterated dimethyl sulfoxide (DMSO-$D_6$) or deuterated chloroform ($CDCl_3$) as the solvent and TMS as the internal standard.

Preparation Example 1: Preparation of the Target Compound I

The synthetic route of the target compound I-1 is shown below:

run at room temperature for 8 hours. The pH of the reaction mixture was adjusted to 8 by adding 1 mol/L hydrochloric acid, and the ethanol was evaporated, followed by addition of water (10 mL). The mixture was extracted with 20 mL ethyl acetate three times, and the organic phases were combined, washed with saturated brine, dried over anhydrous sodium sulfate and filtered. The filtrate was concentrated to give 9.3 g of intermediate 2-1, which was directly used in the next reaction without purification.

Step (2): Preparation of Ethyl 5-phenyl-1H-pyrazole-3-carboxylate (Intermediate 3-1)

The above obtained intermediate 2-1 (9.3 g, 0.042 mol) was added into a round-bottom flask charged with 50 mL of ethanol, followed by addition of hydrazine hydrate (2.1 g, 0.042 mol) dropwise under stirring at room temperature.

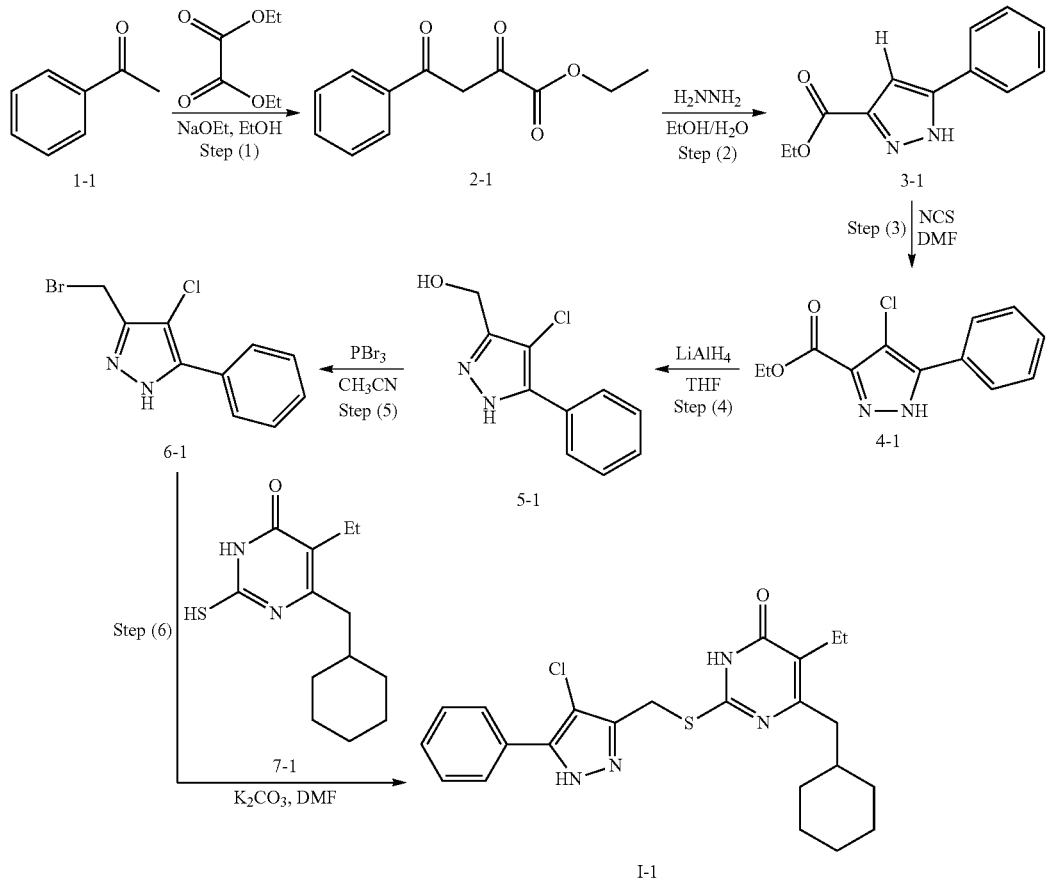

Step (1): Preparation of Ethyl 2,4-dioxo-4-phenylbutyrate (Intermediate 2-1)

40 mL of ethanol was added into a 200 mL round-bottom flask, followed by addition of sodium (2 g, 0.083 mol) in batches under stirring at room temperature. After the above mixture cooled to room temperature, acetophenone (5 g, 0.042 mol) was added, followed by addition of diethyl oxalate (7.4 g, 0.046 mol), and the reaction was allowed to After the completion of the addition, the mixture was refluxed for 3 hours and then cooled to room temperature. The ethanol was evaporated, and 10 mL of water was added. The mixture was extracted with ethyl acetate (3×20 mL), and the organic phases were combined, washed with saturated brine, dried over anhydrous sodium sulfate and concentrated under reduced pressure. The residue was recrystallized with ethyl acetate/petroleum ether (1:5) to give 8.68 g of intermediate 3-1 with a yield of 95.6%.

Step (3): Preparation of Ethyl 4-chloro-5-phenyl-1H-pyrazole-3-carboxylate (Intermediate 4-1)

Intermediate 3-1 (2 g, 9.20 mmol) was added into a 100 mL round bottom flask, followed by addition of 12 mL of a mixed solvent of $CH_3CN$ and DMF ($CH_3CN$:DMF=5:1). NCS was added to the above solution under stirring at room temperature, and the resulting mixture was warmed to 60° C. The reaction was allowed to run at 60° C. for 10 hours until the reaction was complete. The acetonitrile was evaporated under reduced pressure, and the mixture was extracted with ethyl acetate (3×20 mL). The organic phases were combined, washed with saturated brine, and dried over anhydrous sodium sulfate. The solvent was evaporated under reduced pressure to give a crude product of the intermediate 4, which was separated by column chromatography (ethyl acetate:petroleum ether=1:4) to give a pure product of intermediate 4-1 (1.16 g, 50.5%).

Step (4): Preparation of 4-chloro-5-phenyl-1H-pyrazole-3-methanol (Intermediate 5-1)

Intermediate 4-1 (1.16 g, 4.64 mmol) was added into a 100 mL round-bottom flask, followed by addition of 10 mL of anhydrous THF. $LiAlH_4$ (0.277 g, 6.96 mmol) was added in batches to the above solution under an ice bath and the protection of nitrogen atmosphere. The resulting mixture was stirred at room temperature for 2 hours until the reaction was complete. Subsequently, saturated aqueous ammonium chloride solution was added dropwise to the reaction solution under ice bath to quench the reaction. The mixture was filtered by suction, and the filtrate was extracted with ethyl acetate. The organic phases were combined, washed with saturated brine, dried over anhydrous sodium sulfate and concentrated under reduced pressure. The residue was recrystallized with ethyl acetate/petroleum ether (1:3) to give a pure product of intermediate 5-1 (0.768 g, yield 79.6%).

Step (5): Preparation of 3-bromomethyl-4-chloro-5-phenyl-1H-pyrazole (Intermediate 6-1)

The above obtained intermediate 5-1 (0.768 g, 3.69 mmol) was added into a 50 mL round-bottom flask, followed by addition of 15 mL of acetonitrile. $PBr_3$ (1.20 g, 4.43 mmol) was added dropwise to the above solution under an ice bath. After completion of the addition, the reaction solution was warmed to 80° C. and the reaction was allowed to run for 1 hour. After the completion of the reaction, the reaction solution was poured into ice water, and the acetonitrile was evaporated under reduced pressure. The pH was adjusted to weakly alkaline with saturated $NaHCO_3$, and the mixture was filtered by suction. The filtrate was extracted with ethyl acetate, and the organic phases were combined, washed with saturated brine and dried over anhydrous sodium sulfate, and concentrated under reduced pressure. The residue was recrystallized with ethyl acetate/petroleum ether (1:3) to give a pure product of intermediate 6-1 (0.681 g, yield 89.6%).

Step (6): Preparation of the Target Compound I-1

6-(Cyclohexylmethyl)-5-ethyl-2-mercaptopyrimidin-4(3H)-one 7-1 (0.003 mol, 0.728 g) was added into 9 mL of DMF and stirred until dissolved, followed by addition of anhydrous $K_2CO_3$ (0.004 mol, 0.553 g). The resulting mixture was stirred at room temperature for 30 minutes, and then 5 mL of a solution of intermediate 6-1 (0.681 g, 0.003 mol) in DMF was added. The reaction solution was stirred for 3 hours until the reaction was completed, and then poured into 10 mL of ice water, during which a white solid precipitated out. The mixture was filtered or extracted with ethyl acetate to obtain a crude product, which was purified by column chromatography with ethyl acetate/petroleum ether (1:4) as the eluent to give the target product I-1.

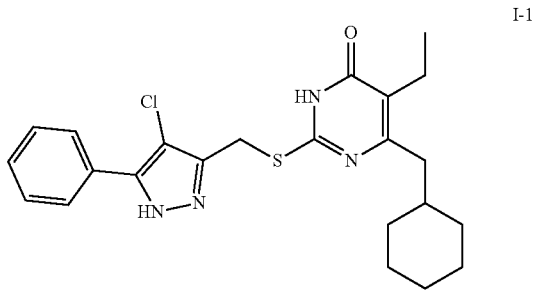 [SMILES: CCc1c(CC2CCCCC2)nc(SCc2n[nH]c(-c3ccccc3)c2Cl)[nH]c1=O]

I-1

The product was obtained as a white crystal with a yield of 86%. $^1$H NMR (DMSO-$d_6$, 300 MHz) δ 0.94-0.97 (t, 3H, J=7.2 Hz, $CH_3$), 0.99 (m, 2H, Cyclohexyl-H), 1.06-1.08 (m, 3H, Cyclohexyl-H), 1.56-1.59 (m, 5H, Cyclohexyl-H), 1.81 (m, 1H, Cyclohexyl-H), 2.32-2.34 (d, 2H, J=6.0 Hz, $CH_2$-Cyclohexyl), 2.36-2.38 (m, 2H, $CH_2CH_3$), 4.44 (s, 2H, $CH_2$—S), 7.40-7.51 (m, 3H, Ph-H), 7.77-7.79 (m, 2H, Ph-H), 10.88 (br, 1H, NH), 13.19 (br, 1H, NH); $^{13}$C NMR (DMSO $d_6$, 75 MHz) δ 13.19, 18.01, 25.00 (2C), 25.73 (2C), 25.87, 32.63, 36.53, 40.76, 105.07, 121.05, 126.42, 126.42, 126.42, 128.67 (3C), 140.28, 141.02, 155.86, 161.05, 162.92.

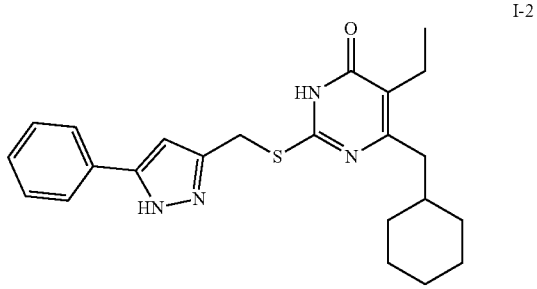 [SMILES: CCc1c(CC2CCCCC2)nc(SCc2cc(-c3ccccc3)[nH]n2)[nH]c1=O]

I-2

Compound I-2 was prepared according to method for preparing the target compound I-1 except that the step (3) was omitted.

The product was obtained as a white solid with a yield of 87%. $^1$H NMR ($CDCl_3$, 300 MHz) δ 0.85-0.88 (t, 3H, J=8.1 Hz, $CH_3$), 0.97-1.00 (m, 2H, Cyclohexyl-H), 1.07-1.12 (m, 3H, Cyclohexyl-H), 1.65-1.69 (m, 5H, Cyclohexyl-H), 1.82 (m, 1H, Cyclohexyl-H), 2.46-2.48 (d, 2H, J=6.9 Hz, $CH_2$—Cyclohexyl), 2.51-2.53 (m, 2H, $CH_2CH_3$), 4.42 (s, 2H, $CH_2$—S), 6.52 (s, 1H, pyrazole), 7.34-7.36 (m, 3H, Ph-H), 7.67-7.69 (m, 2H, Ph-H), 10.24-10.73 (br, 1H, NH), 13.19 (br, 1H, NH); $^{13}$C NMR ($CDCl_3$, 75 MHz) δ 13.37, 18.75, 26.31 (2C), 26.40, 26.90 (2C), 33.36, 37.50, 41.80, 102.28, 122.74, 125.71 (2C), 128.32, 128.86 (2C), 130.56, 146.29, 146.99, 156.37, 163.11, 164.73.

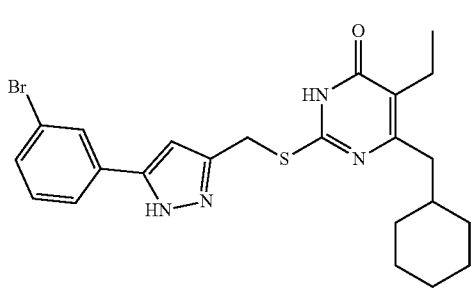

I-3

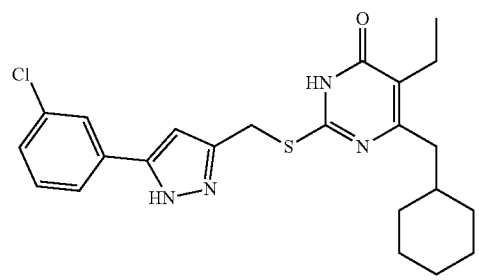

I-5

Compound I-3 was prepared according to method for preparing the target compound I-1 except that 1-(3-bromophenyl)ethanone was used as the raw material 1 in the step (1) and the step (3) was omitted.

The product was obtained as a white crystal with a yield of 74%. $^1$H NMR (CDCl$_3$, 300 MHz) δ 0.89-0.91 (t, 3H, J=6.0 Hz, CH$_3$), 1.04 (m, 2H, Cyclohexyl-H), 1.13 (m, 3H, Cyclohexyl-H), 1.69 (m, 5H, Cyclohexyl-H), 1.84 (m, 1H, Cyclohexyl-H), 2.53 (m, 2H, CH$_2$-Cyclohexyl), 2.53 (m, 2H, CH$_2$), 4.45 (s, 2H, CH$_2$S), 6.53 (s, 1H, pyrazole-H), 7.23-7.25 (m, 1H, Ph-H), 7.41-7.44 (m, 1H, Ph-H), 7.63-7.65 (m, 1H, Ph-H), 7.90 (m, 1H, Ph-H), 12.36 (br, 1H, NH), 13.19 (br, 1H, NH); $^{13}$C NMR (CDCl$_3$, 75 MHz) δ 13.38, 18.75, 26.32 (5C), 33.38, 37.58, 41.90, 102.64, 122.64, 122.92, 124.29, 128.73, 130.29, 131.00, 133.49, 144.90, 147.13, 156.42, 163.40, 164.88.

Compound I-5 was prepared according to method for preparing the target compound I-1 except that 1-(3-chlorophenyl)ethanone was used as the raw material 1 in the step (1) and the step (3) was omitted.

The product was obtained as a white crystal with a yield of 85%. $^1$H NMR (CDCl$_3$, 300 MHz) δ 0.97-1.01 (m, 2H, Cyclohexyl-H), 1.01-1.12 (t, 3H, J=7.2 Hz, CH$_3$), 1.17-1.21 (m, 3H, Cyclohexyl-H), 1.65-1.69 (m, 5H, Cyclohexyl-H), 1.80 (m, 1H, Cyclohexyl-H), 2.47-2.49 (d, 2H, J=6.6 Hz, CH$_2$—Cyclohexyl), 2.51-2.54 (m, 2H, CH$_2$), 4.41 (s, 2H, CH$_2$—S), 6.50 (s, 1H, pyrazole-H), 7.25-7.30 (m, 2H, Ph-H), 7.56 (m, 1H, Ph-H), 7.58-7.70 (m, 1H, Ph-H), 12.56 (br, 1H, NH); $^{13}$C NMR (CDCl$_3$, 75 MHz) δ 13.36, 18.74, 26.13 (5C), 33.37, 37.61, 41.92, 102.60, 122.69, 123.82, 125.86, 128.12, 130.05, 133.19, 134.73, 144.98, 147.21, 156.52, 163.40, 164.88.

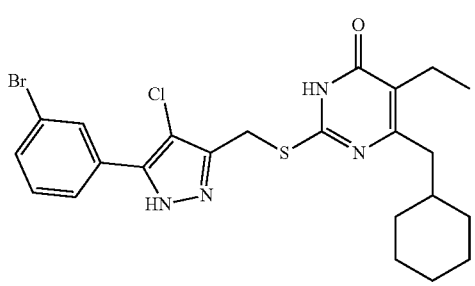

I-4

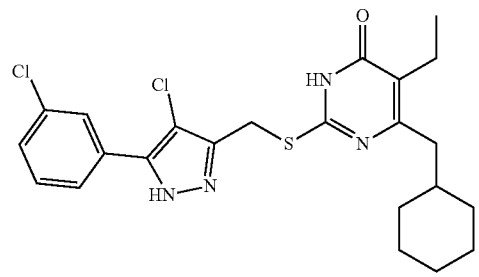

I-6

Compound I-4 was prepared according to method for preparing the target compound I-1 except that 1-(3-bromophenyl)ethanone was used as the raw material 1 in the step (1).

The product was obtained as a white crystal with a yield of 89%. $^1$H NMR (DMSO-d$_6$, 300 MHz) δ 0.93-0.95 (t, 3H, J=7.2 Hz, CH$_3$), 0.98 (m, 2H, Cyclohexyl-H), 1.02-1.04 (m, 3H, Cyclohexyl-H), 1.52-1.55 (m, 5H, Cyclohexyl-H), 1.71 (m, 1H, Cyclohexyl-H), 2.33-2.35 (m, 2H, CH$_2$—Cyclohexyl), 2.33-2.35 (m, 2H, CH$_2$), 4.43 (s, 2H, CH$_2$—S), 7.42-7.45 (m, 1H, Ph-H), 7.55-7.58 (m, 1H, Ph-H), 7.80-7.82 (m, 1H, Ph-H), 7.95 (m, 1H, Ph-H), 13.01 (br, 2H, 2NH); $^{13}$C NMR (DMSO-d$_6$, 75 MHz) δ 13.58, 18.26, 23.13, 25.77 (4C), 32.73, 36.87, 40.65, 104.93, 119.02, 121.85, 125.25, 128.74, 130.77 (2C), 132.99, 140.95, 141.24, 160.40, 161.32, 168.14.

Compound I-6 was prepared according to method for preparing the target compound I-1 except that 1-(3-chlorophenyl)ethanone was used as the raw material 1 in the step (1).

The product was obtained as a white crystal with a yield of 90%. $^1$H NMR (DMSO-d$_6$, 300 MHz) δ 0.88 (m, 2H, Cyclohexyl-H), 0.93-0.98 (t, 3H, J=7.2 Hz, CH$_3$), 1.03-1.05 (m, 3H, Cyclohexyl-H), 1.53-1.56 (m, 5H, Cyclohexyl-H), 1.72 (m, 1H, Cyclohexyl-H), 2.34-2.36 (m, 2H, CH$_2$—Cyclohexyl), 2.34-2.36 (m, 2H, CH$_2$), 4.43 (s, 2H, CH$_2$—S), 7.44-7.53 (m, 2H, Ph-H), 7.76-7.81 (m, 2H, Ph-H), 12.50 (br, 2H, 2NH); $^{13}$CNMR (DMSO-d$_6$, 75 MHz) δ 13.26, 18.05, 23.37, 25.72 (2C), 25.86 (2C), 32.62, 36.62, 40.65, 105.34, 120.48, 124.85, 125.89, 128.02, 130.52, 131.97, 133.39, 140.52, 141.12, 157.09, 161.09, 164.33.

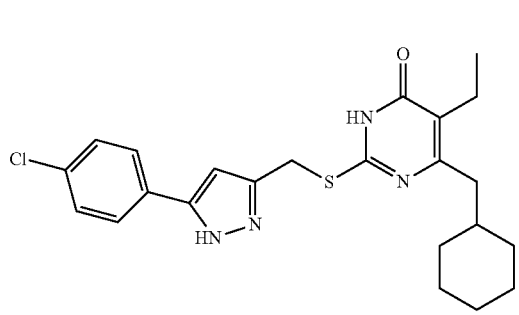

I-7

Compound I-7 was prepared according to method for preparing the target compound I-1 except that 1-(4-chlorophenyl)ethanone was used as the raw material 1 in the step (1) and the step (3) was omitted.

The product was obtained as a white crystal with a yield of 88%. $^1$H NMR (DMSO-$d_6$, 300 MHz) δ 0.97-0.99 (t, 3H, J=7.2 Hz, CH$_3$), 1.09 (m, 2H, Cyclohexyl-H), 1.18 (m, 3H, Cyclohexyl-H), 1.57 (m, 5H, Cyclohexyl-H), 1.75 (m, 1H, Cyclohexyl-H), 2.35-2.39 (m, 2H, CH$_2$—Cyclohexyl), 2.35-2.39 (m, 2H, CH$_2$CH$_3$), 4.39 (s, 2H, CH$_2$—S), 6.58-6.61 (s, 1H, pyrazole-H), 7.28-7.45 (m, 2H, Ph-H), 7.69-7.45 (m, 2H, Ph-H), 12.78 (br, 1H, NH); $^{13}$C NMR (DMSO-$d_6$, 75 MHz) δ 13.21, 18.03, 25.73 (2C), 25.86 (3C), 32.65, 36.58, 40.76, 101.71, 121.98, 124.93, 126.61, 127.66, 128.68, 131.86, 132.08, 145.91, 156.29, 160.85, 163.02.

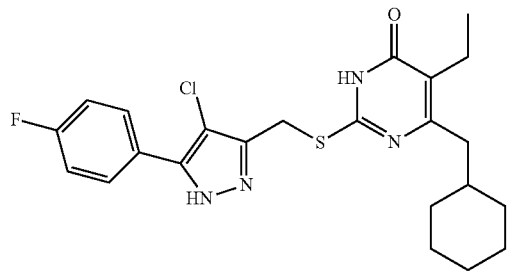

I-9

Compound I-9 was prepared according to method for preparing the target compound I-1 except that 1-(4-fluorophenyl)ethanone was used as the raw material 1 in the step (1).

The product was obtained as a white crystal with a yield of 71%. $^1$H NMR (DMSO-$d_6$, 300 MHz) δ 0.96-0.98 (m, 2H, Cyclohexyl-H), 1.04-1.06 (t, 3H, J=7.8 Hz, CH$_3$), 1.13-1.15 (m, 3H, Cyclohexyl-H), 1.50-1.58 (m, 5H, Cyclohexyl-H), 1.75 (m, 1H, Cyclohexyl-H), 2.35-2.37 (m, 2H, CH$_2$—Cyclohexyl), 2.35-2.37 (m, 2H, CH$_2$), 4.43 (s, 2H, CH$_2$—S), 7.29-7.35 (m, 2H, Ph-H), 7.79-7.84 (m, 2H, Ph-H), 12.96 (br, 2H, 2NH); $^{13}$C NMR (DMSO-$d_6$, 75 MHz) δ 13.17, 17.99, 23.69, 25.72 (2C), 25.86 (2C), 32.61, 36.51, 40.75, 101.97, 115.53, 115.82, 121.11, 128.54, 128.65 (2C), 140.42, 141.63, 155.92, 161.08, 161.96, 162.95.

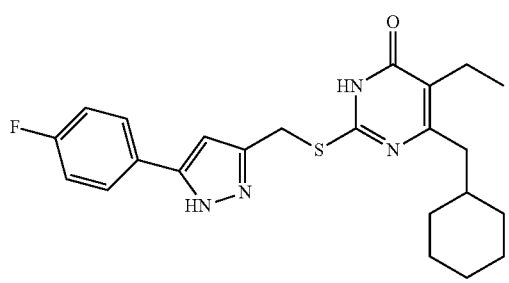

I-8

Compound I-8 was prepared according to method for preparing the target compound I-1 except that 1-(4-fluorophenyl)ethanone was used as the raw material 1 in the step (1) and the step (3) was omitted.

The product was obtained as a white crystal with a yield of 89%. $^1$H NMR (DMSO-$d_6$, 300 MHz) δ 0.90 (m, 2H, Cyclohexyl-H), 0.95-0.99 (t, 3H, J=7.5 Hz, CH$_3$), 1.06-1.09 (m, 3H, Cyclohexyl-H), 1.56-1.60 (m, 5H, Cyclohexyl-H), 1.75 (m, 1H, Cyclohexyl-H), 2.36-2.38 (m, 2H, CH$_2$—Cyclohexyl), 2.36-2.38 (m, 2H, CH$_2$), 4.39 (s, 2H, CH$_2$—S), 6.57 (s, 1H, pyrazole-H), 7.18-7.24 (m, 2H, Ph-H), 7.73-7.77 (m, 2H, Ph-H), 12.78 (br, 1H, NH); $^{13}$C NMR (DMSO-$d_6$, 75 MHz) δ 13.18, 18.02, 25.40, 25.40, 25.72, 25.85 (2C), 32.65, 36.58, 40.71, 101.55, 115.39, 115.68, 121.07, 126.90, 127.00, 127.99, 144.42, 145.63, 156.32, 160.62, 161.56, 163.26.

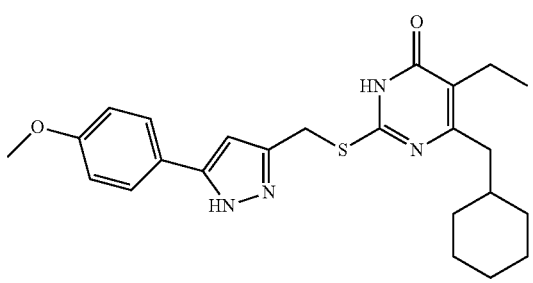

I-10

Compound I-10 was prepared according to method for preparing the target compound I-1 except that 1-(4-methoxyphenyl)ethanone was used as the raw material 1 in the step (1) and the step (3) was omitted.

The product was obtained as a white crystal with a yield of 50%. $^1$H NMR (DMSO-$d_6$, 300 MHz) δ 0.95-1.00 (t, 3H, J=7.2 Hz, CH$_3$), 1.02-1.12 (m, 2H, Cyclohexyl-H), 1.16-1.20 (m, 3H, Cyclohexyl-H), 1.59-1.62 (m, 5H, Cyclohexyl-H), 1.78 (m, 1H, Cyclohexyl-H), 2.36-2.38 (m, 2H, CH$_2$—Cyclohexyl), 2.40 (m, 2H, CH$_2$), 3.76 (s, 3H, OCH$_3$), 4.37 (s, 2H, CH$_2$—S), 6.49 (s, 1H, pyrazole-H), 6.95-6.98 (m, 2H, Ph-H), 7.62-7.65 (m, 2H, Ph-H), 12.07-13.10 (br, 1H, NH); $^{13}$C NMR (DMSO-$d_6$, 75 MHz) δ 13.23, 18.02, 25.74 (2C), 25.88 (3C), 32.66, 36.58, 40.71, 55.06, 100.85, 114.11 (2C), 121.10, 123.45, 126.31 (2C), 142.23, 145.48, 156.39, 158.90, 160.65, 163.03.

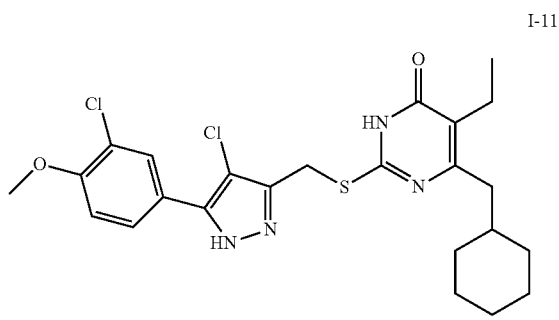 [SMILES: CCc1c(CC2CCCCC2)nc(SCc2n[nH]c(-c3ccc(OC)c(Cl)c3)c2Cl)[nH]c1=O]

I-11

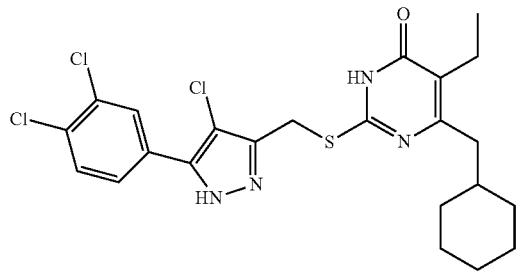

I-13

Compound I-11 was prepared according to method for preparing the target compound I-1 except that 1-(3-chloro-4-methoxyphenyl)ethanone was used as the raw material 1 in the step (1).

The product was obtained as a white crystal with a yield of 53%. $^1$H NMR (DMSO-d$_6$, 300 MHz) δ 0.88 (m, 2H, Cyclohexyl-H), 0.93-0.98 (t, 3H, J=6.9 Hz, CH$_3$), 1.04-1.07 (m, 3H, Cyclohexyl-H), 1.54-1.57 (m, 5H, Cyclohexyl-H), 1.74 (m, 1H, Cyclohexyl-H), 2.34-2.36 (m, 2H, CH$_2$—Cyclohexyl), 2.34-2.36 (m, 2H, CH$_2$), 3.89 (s, 3H, OCH$_3$), 4.42 (s, 2H, CH$_2$—S), 7.24-7.27 (s, 1H, Ph-H), 7.72-7.81 (m, 2H, Ph-H), 12.52-13.21 (br, 2H, 2NH); $^{13}$C NMR (DMSO-d$_6$, 75 MHz) δ 13.18, 17.99, 23.71, 25.72 (2C), 25.86 (2C), 32.61, 36.52, 40.24, 56.15, 104.76, 112.91, 121.29, 123.5, 126.41, 127.59, 127.81, 154.49, 141.36, 142.55, 155.96, 160.95, 162.96.

Compound I-13 was prepared according to method for preparing the target compound I-1 except that 1-(3,4-dichlorophenyl)ethanone was used as the raw material 1 in the step (1).

The product was obtained as a white crystal with a yield of 82%. $^1$H NMR (DMSO-d$_6$, 300 MHz) δ 0.93-0.98 (t, 3H, J=7.2 Hz, CH$_3$), 1.04 (m, 2H, Cyclohexyl-H), 1.04 (m, 3H, Cyclohexyl-H), 1.53-1.55 (m, 5H, Cyclohexyl-H), 1.70 (m, 1H, Cyclohexyl-H), 2.33-2.36 (m, 2H, CH$_2$—Cyclohexyl), 2.33-2.36 (m, 2H, CH$_2$), 4.42 (s, 2H, CH$_2$S), 7.46-7.55 (m, 2H, Ph-H), 7.98-7.99 (m, 1H, Ph-H), 12.72-13.36 (br, 2H, 2NH); $^{13}$CNMR (DMSO-d$_6$, 75 MHz) δ 13.17, 17.99, 23.17, 25.70 (2C), 25.84 (2C), 32.59, 36.52, 40.76, 105.57, 121.09, 124.86, 126.07, 128.73, 130.91, 131.49, 133.42, 140.68, 141.77, 155.74, 161.08, 162.96.

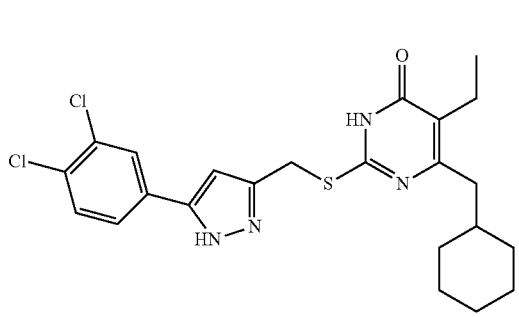

I-12

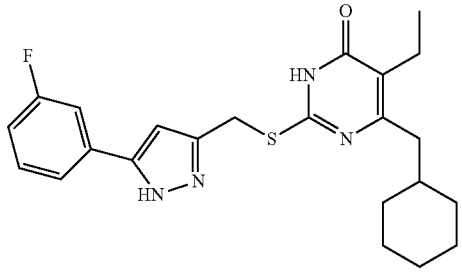

I-14

Compound I-12 was prepared according to method for preparing the target compound I-1 except that 1-(3,4-dichlorophenyl)ethanone was used as the raw material 1 in the step (1) and the step (3) was omitted.

The product was obtained as a white crystal with a yield of 51%. $^1$H NMR (DMSO-d$_6$, 300 MHz) δ 0.94 (m, 2H, Cyclohexyl-H), 0.96-0.99 (t, 3H, J=7.2 Hz, CH$_3$), 1.05-1.08 (m, 3H, Cyclohexyl-H), 1.55-1.58 (m, 5H, Cyclohexyl-H), 1.72 (m, 1H, Cyclohexyl-H), 2.35-2.37 (m, 2H, CH$_2$—Cyclohexyl), 2.35-2.37 (m, 2H, CH$_2$), 4.39 (s, 2H, CH$_2$—S), 6.68 (s, 1H, pyrazole-H), 7.59-7.62 (m, 1H, Ph-H), 7.68-7.72 (m, 1H, Ph-H), 7.94-7.95 (m, 1H, Ph-H), 12.81 (br, 2H, 2NH); $^{13}$C NMR (DMSO-d$_6$, 75 MHz) δ 13.19, 18.02, 24.90, 25.72 (2C), 25.86 (2C), 32.63, 36.58, 40.82, 102.26, 121.06, 124.96, 126.47 (2C), 129.78, 130.82, 131.53, 141.48, 144.69, 156.09, 161.07, 162.99.

Compound I-14 was prepared according to method for preparing the target compound I-1 except that 1-(3-fluorophenyl)ethanone was used as the raw material 1 in the step (1) and the step (3) was omitted.

The product was obtained as a white crystal with a yield of 74%. $^1$H NMR (DMSO-d$_6$, 300 MHz) δ 0.97-1.00 (m, 2H, Cyclohexyl-H), 1.06-1.10 (t, 3H, J=7.2 Hz, CH$_3$), 1.13-1.16 (m, 3H, Cyclohexyl-H), 1.64-1.68 (m, 5H, Cyclohexyl-H), 1.80 (m, 1H, Cyclohexyl-H), 2.45-2.47 (m, 2H, CH$_2$—Cyclohexyl), 2.45-2.47 (m, 2H, CH$_2$), 4.39 (s, 2H, CH$_2$—S), 6.49 (s, 1H, pyrazole-H), 6.96 (m, 1H, Ph-H), 7.28-7.46 (m, 3H, Ph-H), 12.40 (br, 2H, 2NH); $^{13}$C NMR (DMSO-d$_6$, 75 MHz) δ 13.32, 18.72, 26.30 (5C), 33.37, 37.56, 41.90, 102.63, 112.64, 114.98, 121.33, 122.75, 130.36, 133.35, 145.29, 147.05, 156.25, 161.46, 163.32, 164.73.

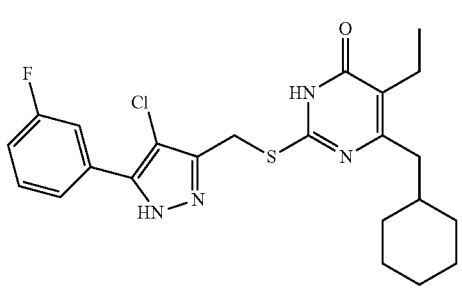

I-15

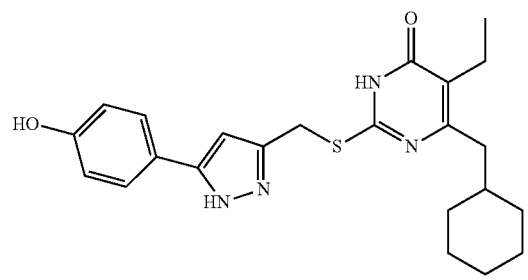

I-17

Compound I-15 was prepared according to method for preparing the target compound I-1 except that 1-(3-fluorophenyl)ethanone was used as the raw material 1 in the step (1).

The product was obtained as a white crystal with a yield of 89%. $^1$H NMR (DMSO-d$_6$, 300 MHz) δ 0.95 (m, 3H, CH$_3$), 1.04 (m, 2H, Cyclohexyl-H), 1.04 (m, 3H, Cyclohexyl-H), 1.53 (m, 5H, Cyclohexyl-H), 1.72 (m, 1H, Cyclohexyl-H), 2.34 (m, 2H, CH$_2$-Cyclohexyl), 2.34 (m, 2H, CH$_2$), 4.43 (s, 2H, CH$_2$—S), 7.22 (m, 1H, Ph-H), 7.55-7.65 (m, 3H, Ph-H), 12.98-13.05 (br, 2H, 2NH); $^{13}$C NMR (DMSO-d$_6$, 75 MHz) δ 13.15, 17.99, 23.55, 25.70 (2C), 25.84 (2C), 32.59, 36.52, 40.76, 105.46, 112.89, 115.10, 121.10, 122.35 (2C), 130.77, 140.68, 141.54, 155.95, 161.11, 162.13, 162.95.

Compound I-17 was prepared according to method for preparing the target compound I-1 except that 1-(3-hydroxyphenyl)ethanone was used as the raw material 1 in the step (1) and the step (3) was omitted.

The product was obtained as a white crystal with a yield of 54%. $^1$H NMR (DMSO-d$_6$, 300 MHz) δ 0.96-1.00 (t, 3H, J=7.2 Hz, CH$_3$), 1.09-1.12 (m, 2H, Cyclohexyl-H), 1.09-1.12 (m, 3H, Cyclohexyl-H), 1.59-1.62 (m, 5H, Cyclohexyl-H), 1.79 (m, 1H, Cyclohexyl-H), 2.36-2.40 (m, 2H, CH$_2$—Cyclohexyl), 2.36-2.40 (m, 2H, CH$_2$), 4.36 (s, 2H, CH$_2$—S), 6.42 (s, 1H, pyrazole-H), 6.78-6.81 (m, 2H, Ph-H), 7.50-7.53 (m, 2H, Ph-H), 9.62 (br, 1H, OH), 12.67 (br, 2H, 2NH); $^{13}$C NMR (DMSO-d$_6$, 75 MHz) δ 13.22, 18.04, 25.75, 25.88 (2C), 26.07 (2C), 32.67, 36.59, 40.76, 100.49, 115.48 (2C), 121.42, 126.40 (2C), 128.38, 145.64, 156.39, 157.25, 157.25, 160.82, 162.98.

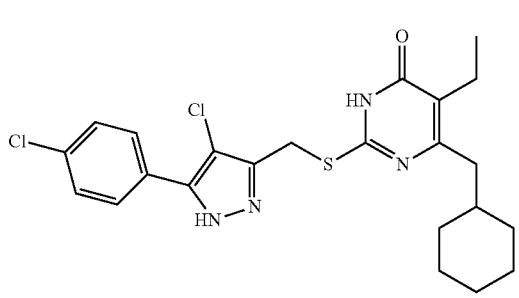

I-16

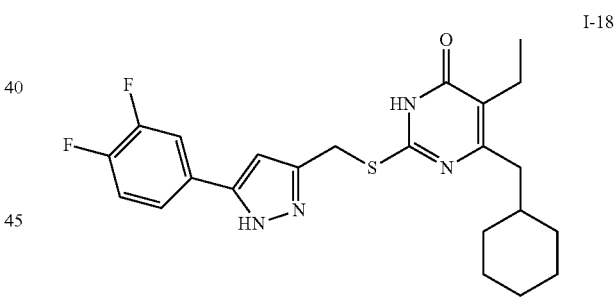

I-18

Compound I-16 was prepared according to method for preparing the target compound I-1 except that 1-(4-chlorophenyl)ethanone was used as the raw material 1 in the step (1).

The product was obtained as a white crystal with a yield of 90%. $^1$H NMR (DMSO-d$_6$, 300 MHz) δ 0.88 (m, 2H, Cyclohexyl-H), 0.93-0.98 (t, 3H, J=7.2 Hz, CH$_3$), 1.03-1.05 (m, 3H, Cyclohexyl-H), 1.53-1.56 (m, 5H, Cyclohexyl-H), 1.74 (m, 1H, Cyclohexyl-H), 2.34-2.36 (m, 2H, CH$_2$-Cyclohexyl), 2.34-2.36 (m, 2H, CH$_2$), 4.43 (s, 2H, CH$_2$—S), 7.52-7.55 (m, 2H, Ph-H), 7.79-7.81 (m, 2H, Ph-H), 13.01 (br, 2H, 2NH); $^{13}$C NMR (DMSO-d$_6$, 75 MHz) δ 13.18, 17.99, 23.53, 25.71 (2C), 25.85 (2C), 32.60, 36.52, 40.75, 105.26, 121.09, 128.03 (3C), 128.76 (2C), 133.06, 140.46, 141.02, 155.78, 161.11, 162.93.

Compound I-18 was prepared according to method for preparing the target compound I-1 except that 1-(3,4-difluorophenyl)ethanone was used as the raw material 1 in the step (1) and the step (3) was omitted.

The product was obtained as a white crystal with a yield of 89%. $^1$H NMR (DMSO-d$_6$, 300 MHz) δ 0.94-0.99 (t, 3H, J=7.2 Hz, CH$_3$), 1.05-1.08 (m, 2H, Cyclohexyl-H), 1.05-1.08 (m, 3H, Cyclohexyl-H), 1.55-1.59 (m, 5H, Cyclohexyl-H), 1.72 (m, 1H, Cyclohexyl-H), 2.32-2.38 (m, 2H, CH$_2$—Cyclohexyl), 2.32-2.38 (m, 2H, CH$_2$), 4.38 (s, 2H, CH$_2$—S), 6.64 (s, 1H, pyrazole-H), 7.38-7.45 (m, 1H, Ph-H), 7.48-7.59 (m, 1H, Ph-H), 7.71-7.78 (m, 1H, Ph-H), 11.81-12.97 (br, 2H, 2NH); $^{13}$C NMR (DMSO-d$_6$, 75 MHz) δ 13.16, 18.01, 24.98, 25.70 (2C), 25.84 (2C), 32.62, 36.59, 40.71, 102.03, 113.8, 117.78, 121.04, 121.63, 129.61, 143.99, 145.48, 149.06, 149.47, 156.27, 160.66, 163.12.

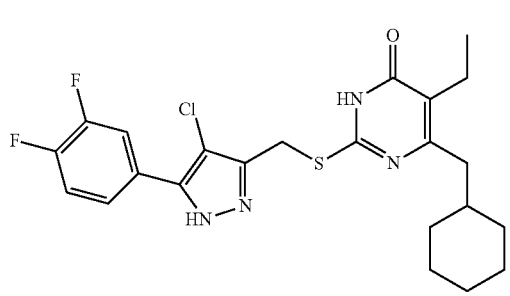

I-19

Compound I-19 was prepared according to method for preparing the target compound I-1 except that 1-(3,4-difluorophenyl)ethanone was used as the raw material 1 in the step (1).

The product was obtained as a white crystal with a yield of 68%. ¹H NMR (DMSO-d$_6$, 300 MHz) δ 0.92-0.97 (t, 3H, J=7.2 Hz, CH$_3$), 1.02-1.04 (m, 2H, Cyclohexyl-H), 1.12-1.16 (m, 3H, Cyclohexyl-H), 1.52-1.55 (m, 5H, Cyclohexyl-H), 1.72 (m, 1H, Cyclohexyl-H), 2.33-2.35 (m, 2H, CH$_2$-Cyclohexyl), 2.33-2.35 (m, 2H, CH$_2$), 4.42 (s, 2H, CH$_2$—S), 7.51-7.57 (m, 1H, Ph-H), 7.64-7.73 (m, 1H, Ph-H), 7.73-7.80 (m, 1H, Ph-H), 13.00 (br, 2H, 2NH); ¹³C NMR (DMSO-d$_6$, 75 MHz) δ 13.12, 17.98, 23.26, 25.70 (2C), 25.83 (2C), 32.59, 36.52, 40.75, 105.29, 115.24, 117.78, 121.10, 123.29 (2C), 140.50, 141.28, 149.31, 149.23, 155.79, 161.07, 162.95.

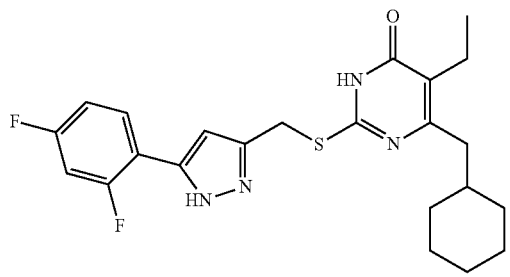

I-20

Compound I-20 was prepared according to method for preparing the target compound I-1 except that 1-(2,4-difluorophenyl)ethanone was used as the raw material 1 in the step (1) and the step (3) was omitted.

The product was obtained as a white crystal with a yield of 75%. ¹H NMR (CDCl$_3$, 300 MHz) δ 1.07-1.10 (m, 2H, Cyclohexyl-H), 1.12-1.17 (t, 3H, J=6.9 Hz, CH$_3$), 1.22-1.26 (m, 3H, Cyclohexyl-H), 1.66-1.70 (m, 5H, Cyclohexyl-H), 1.82 (m, 1H, Cyclohexyl-H), 2.48-2.56 (m, 2H, CH$_2$-Cyclohexyl), 2.48-2.56 (m, 2H, CH$_2$), 4.44 (s, 2H, CH$_2$—S), 6.64 (s, 1H, pyrazole-H), 6.85-6.92 (m, 2H, Ph-H), 7.76-7.7 (m, 1H, Ph-H), 12.09-12.42 (br, 2H, 2NH); ¹³C NMR (CDCl$_3$, 75 MHz) δ 13.33, 18.72, 26.29 (3C), 26.38 (2C), 33.36, 37.54, 41.90, 104.66, 111.90, 115.45, 115.62, 122.75, 129.12, 141.28, 145.26, 159.5, 162.76, 156.33, 163.22, 164.79.

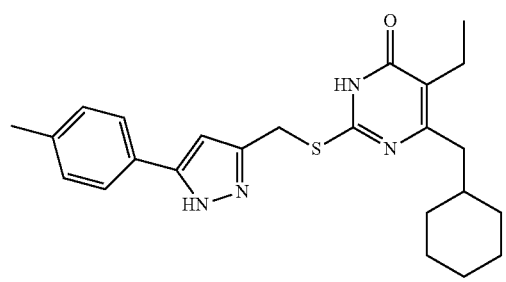

I-21

Compound I-21 was prepared according to method for preparing the target compound I-1 except that 1-(4-methylphenyl)ethanone was used as the raw material 1 in the step (1) and the step (3) was omitted.

The product was obtained as a white crystal with a yield of 80%. ¹H NMR (DMSO-d$_6$, 300 MHz) δ 0.96-1.00 (t, 3H, J=6.9 Hz, CH$_3$), 1.11 (m, 2H, Cyclohexyl-H), 1.11 (m, 3H, Cyclohexyl-H), 1.59 (m, 5H, Cyclohexyl-H), 1.80 (m, 1H, Cyclohexyl-H), 2.28 (s, 3H, CH$_3$-Ph), 2.37 (m, 2H, Cyclohexyl-H), 2.37 (m, 2H, CH$_2$), 4.39 (s, 2H, CH$_2$—S), 6.53 (s, 1H, pyrazole-H), 7.17-7.19 (m, 2H, Ph-H), 7.58-7.61 (m, 2H, Ph-H), 12.77 (br, 2H, 2NH); ¹³C NMR (DMSO-d$_6$, 75 MHz) δ 13.21, 18.05, 20.70, 25.77 (3C), 25.88 (2C), 32.70, 36.59, 40.89, 101.20, 121.16, 124.86 (2C), 128.09, 129.23 (2C), 137.01, 142.32, 145.67, 156.31, 160.94, 162.89.

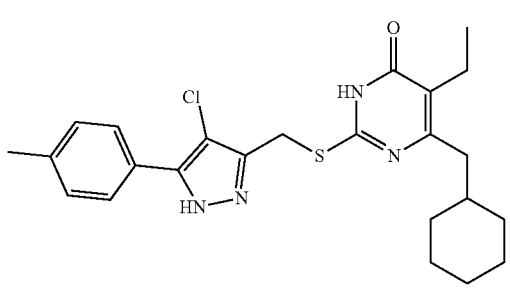

I-22

Compound I-22 was prepared according to method for preparing the target compound I-1 except that 1-(4-methylphenyl)ethanone was used as the raw material 1 in the step (1).

The product was obtained as a white crystal with a yield of 63%. ¹H NMR (DMSO-d$_6$, 300 MHz) δ 0.97-0.99 (m, 2H, Cyclohexyl-H), 1.06-1.12 (t, 3H, J=7.8 Hz, CH$_3$), 1.17 (m, 3H, Cyclohexyl-H), 1.52-1.59 (m, 5H, Cyclohexyl-H), 1.79 (m, 1H, Cyclohexyl-H), 2.31 (s, 3H, CH$_3$-Ph), 2.35-2.37 (m, 2H, CH$_2$-Cyclohexyl), 2.35-2.37 (m, 2H, CH$_2$), 4.44 (s, 2H, CH$_2$—S), 7.25-7.28 (m, 2H, Ph-H), 7.65-7.6 (m, 2H, Ph-H), 12.94 (br, 2H, 2NH); ¹³C NMR (DMSO-d$_6$, 75 MHz) δ 13.17, 18.00, 20.76, 24.04, 25.76 (2C), 25.89 (2C), 32.66, 36.51, 40.76, 104.82, 121.10, 126.68 (3C), 129.22 (2C), 137.95, 140.17, 141.01, 156.00, 161.02, 162.93.

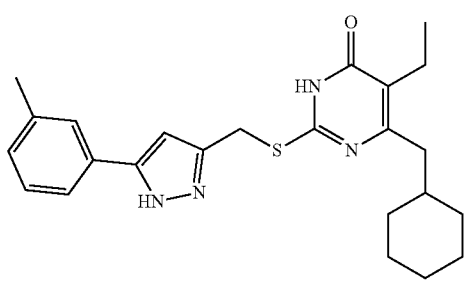

I-23

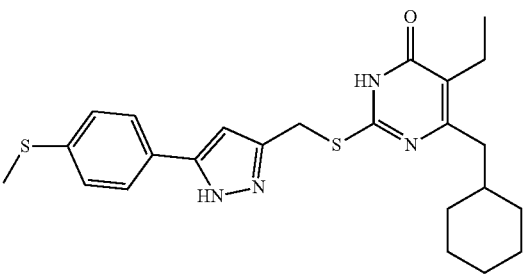

I-25

Compound I-23 was prepared according to method for preparing the target compound I-1 except that 1-(3-methylphenyl)ethanone was used as the raw material 1 in the step (1) and the step (3) was omitted.

The product was obtained as a white crystal with a yield of 74%. $^1$H NMR (DMSO-d$_6$, 300 MHz) δ 0.92 (m, 2H, Cyclohexyl-H), 0.96-1.01 (t, 3H, J=6.9 Hz, CH$_3$), 1.08-1.14 (m, 3H, Cyclohexyl-H), 1.53-1.60 (m, 5H, Cyclohexyl-H), 1.80 (m, 1H, Cyclohexyl-H), 2.30 (s, 3H, CH$_3$-Ph), 2.37-2.39 (m, 2H, CH$_2$-Cyclohexyl), 2.37-2.39 (m, 2H, CH$_2$), 4.41 (s, 2H, CH$_2$—S), 6.55 (s, 1H, pyrazole-H), 7.06-7.09 (m, 1H, Ph-H), 7.23-7.28 (m, 1H, Ph-H), 7.50-7.54 (m, 2H, Ph-H), 12.79 (br, 2H, 2NH); $^{13}$CNMR (DMSO-d$_6$, 75 MHz) δ 13.18, 18.07, 20.92, 25.78 (3C), 25.89 (2C), 32.70, 36.62, 40.91, 101.48, 121.17, 122.11, 125.55, 128.31, 128.53, 130.87, 137.77, 145.19, 145.93, 156.32, 160.94, 162.91.

Compound I-25 was prepared according to method for preparing the target compound I-1 except that 1-(4-methylthiophenyl)ethanone was used as the raw material 1 in the step (1) and the step (3) was omitted.

The product was obtained as a white crystal with a yield of 53%. $^1$H NMR (DMSO-d$_6$, 300 MHz) δ 0.96-1.00 (t, 3H, J=7.2 Hz, CH$_3$), 1.08-1.10 (m, 2H, Cyclohexyl-H), 1.15 (m, 3H, Cyclohexyl-H), 1.58 (m, 5H, Cyclohexyl-H), 1.78 (m, 1H, Cyclohexyl-H), 2.37 (s, 3H, CH$_3$S), 2.46-2.50 (m, 2H, CH$_2$—Cyclohexyl), 2.46-2.50 (m, 2H, CH$_2$), 4.40 (s, 2H, CH$_2$—S), 6.55 (CH, pyrazole), 7.25-7.28 (m, 2H, Ph-H), 7.64-7.67 (m, 2H, Ph-H), 12.78 (br, 2H, 2NH); $^{13}$C NMR (DMSO-d$_6$, 75 MHz) δ 13.22, 14.52, 18.05, 25.77 (3C), 25.89 (2C), 32.69, 36.58, 40.88, 101.32, 121.15, 125.41 (2C), 125.99 (2C), 127.65, 137.69, 145.61, 156.25, 160.98, 162.90.

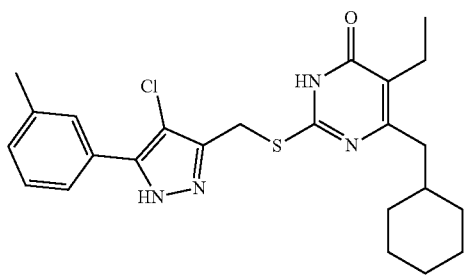

I-24

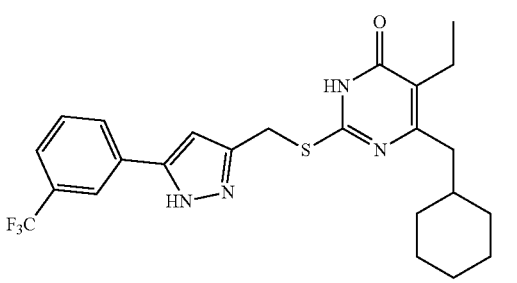

I-26

Compound I-24 was prepared according to method for preparing the target compound I-1 except that 1-(3-methylphenyl)ethanone was used as the raw material 1 in the step (1).

The product was obtained as a white crystal with a yield of 66%. $^1$H NMR (DMSO-d$_6$, 300 MHz) δ 0.89 (m, 2H, Cyclohexyl-H), 0.95-0.99 (t, 3H, J=7.2 Hz, CH$_3$), 1.08 (m, 3H, Cyclohexyl-H), 1.56-1.59 (m, 5H, Cyclohexyl-H), 1.79 (m, 1H, Cyclohexyl-H), 2.30 (s, 3H, CH$_3$-Ph), 2.33-2.37 (m, 2H, CH$_2$—Cyclohexyl), 2.33-2.37 (m, 2H, CH$_2$), 4.45 (s, 2H, CH$_2$—S), 7.17-7.19 (m, 1H, Ph-H), 7.31-7.36 (m, 1H, Ph-H), 7.57-7.59 (m, 2H, Ph-H), 12.95 (br, 2H, 2NH); $^{13}$C NMR (DMSO-d$_6$, 75 MHz) δ 13.16, 18.02, 20.97, 23.97, 25.76 (2C), 25.90 (2C), 32.67, 36.52, 40.79, 105.08, 121.10, 123.60, 126.98 (2C), 128.52, 129.03, 137.81, 141.98, 142.53, 156.03, 161.03, 162.94.

Compound I-26 was prepared according to method for preparing the target compound I-1 except that 1-(3-trifluoromethylphenyl)ethanone was used as the raw material 1 in the step (1) and the step (3) was omitted.

The product was obtained as a white crystal with a yield of 68%. $^1$H NMR (DMSO-d$_6$, 300 MHz) δ 0.75 (m, 2H, Cyclohexyl-H), 0.96-0.98 (t, 3H, J=6.6 Hz, CH$_3$), 1.06 (m, 3H, Cyclohexyl-H), 1.54 (m, 5H, Cyclohexyl-H), 1.72 (m, 1H, Cyclohexyl-H), 2.34-2.36 (m, 2H, Cyclohexyl-H), 2.34-2.36 (m, 2H, CH$_2$), 4.42 (s, 2H, CH$_2$—S), 6.72 (CH, pyrazole-H), 7.59-7.60 (m, 2H, Ph-H), 8.01-8.0 (m, 2H, Ph-H), 12.58 (br, 2H, 2NH); $^{13}$C NMR (DMSO-d$_6$, 75 MHz) δ 13.12, 18.00, 24.94, 25.68 (2C), 25.79 (2C), 32.61, 36.56, 40.70, 102.09, 121.10, 122.28, 123.83, 125.88, 128.74, 129.56, 130.24, 132.89, 144.05, 146.06, 156.22, 160.68, 163.11

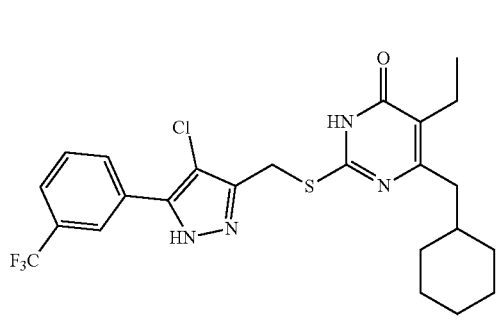

I-27

Compound I-27 was prepared according to method for preparing the target compound I-1 except that 1-(3-trifluoromethylphenyl)ethanone was used as the raw material 1 in the step (1).

The product was obtained as a white crystal with a yield of 63%. $^1$H NMR (DMSO-d$_6$, 300 MHz) δ 1.68-1.81 (m, 2H, Cyclohexyl-H), 1.85-1.90 (t, 3H, J=6.9 Hz, CH$_3$), 1.93 (m, 3H, Cyclohexyl-H), 2.06-2.45 (m, 5H, Cyclohexyl-H), 2.62 (m, 1H, Cyclohexyl-H), 3.25-3.27 (m, 2H, Cyclohexyl-H), 3.25-3.27 (m, 2H, CH$_2$CH$_3$), 5.37 (s, 2H, CH$_2$—S), 8.52-8.64 (m, 2H, Ph-H), 8.93-9.04 (m, 2H, Ph-H), 13.94 (br, 2H, 2NH); $^{13}$C NMR (DMSO-d$_6$, 75 MHz) δ 13.10, 17.98, 23.36, 25.66 (2C), 25.79 (2C), 32.58, 36.51, 40.76, 105.54, 121.09 (2C), 122.58, 123.95, 124.66, 128.96, 129.33, 129.92, 140.58, 141.26, 155.81, 161.05, 162.56.

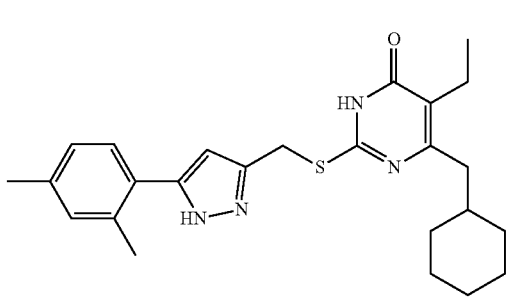

I-29

Compound I-29 was prepared according to method for preparing the target compound I-1 except that 1-(2,4-dimethylphenyl)ethanone was used as the raw material 1 in the step (1) and the step (3) was omitted.

The product was obtained as a white crystal with a yield of 65%. $^1$H NMR (DMSO-d$_6$, 300 MHz) δ 0.96-1.00 (m, 2H, Cyclohexyl-H), 1.04-1.09 (t, 3H, J=7.2 Hz, CH$_3$), 1.17-1.25 (m, 3H, Cyclohexyl-H), 1.65 (m, 5H, Cyclohexyl-H), 1.84 (m, 1H, Cyclohexyl-H), 2.31 (s, 3H, CH$_3$-Ph), 2.35 (s, 3H, CH$_3$-Ph), 2.44-2.50 (m, 2H, CH$_2$-Cyclohexyl), 2.44-2.50 (m, 2H, CH$_2$), 4.46 (s, 2H, CH$_2$—S), 6.35 (CH, pyrazole-H), 6.97-7.03 (m, 2H, Ph-H), 7.30-7.32 (m, 2H, Ph-H), 12.54 (br, 2H, NH); $^{13}$C NMR (DMSO-d$_6$, 75 MHz) δ 13.40, 18.77, 20.86, 21.23, 26.37, 26.50 (2C), 27.51 (2C), 33.43, 37.43, 41.86, 105.16, 122.78, 126.82, 127.29, 129.03, 131.70, 135.80, 138.29, 145.35, 146.58, 156.26, 163.03, 164.67.

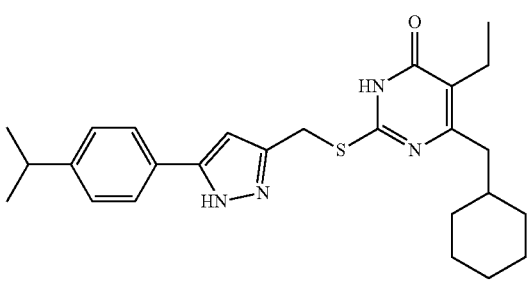

I-28

Compound I-28 was prepared according to method for preparing the target compound I-1 except that 1-(4-isopropylphenyl)ethanone was used as the raw material 1 in the step (1) and the step (3) was omitted.

The product was obtained as a white crystal with a yield of 71%. $^1$H NMR (DMSO-d$_6$, 300 MHz) δ 0.92 (m, 2H, Cyclohexyl-H), 0.96-1.01 (t, 3H, J=7.5 Hz, CH$_3$), 1.08-1.10 (d, 6H, J=7.5 Hz, 2CH$_3$), 1.15-1.17 (m, 3H, Cyclohexyl-H), 1.59 (m, 5H, Cyclohexyl-H), 1.80 (m, 1H, Cyclohexyl-H), 2.37-2.39 (m, 2H, CH$_2$-Cyclohexyl), 2.37-2.39 (m, 2H, CH$_2$), 2.81-2.85 (m, 1H, CHMe$_2$), 4.41 (s, 2H, CH$_2$—S), 6.53 (CH, pyrazole-H), 7.21-7.24 (m, 2H, Ph-H), 7.60-7.63 (m, 2H, Ph-H), 12.78 (br, 1H, NH); $^{13}$C NMR (DMSO-d$_6$, 75 MHz) δ 13.19, 18.06, 23.62 (2), 25.77 (3), 25.89, 25.89, 32.71, 33.16, 36.59, 40.92, 101.29, 121.15, 125.00 (2C), 126.53 (2C), 126.53, 128.49, 145.66, 147.92, 156.35, 160.92, 162.90.

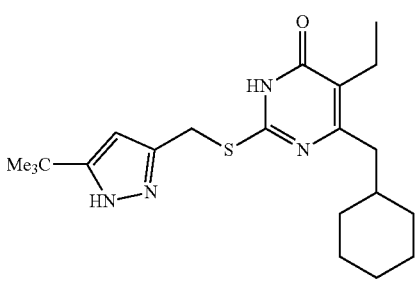

I-30

Compound I-30 was prepared according to method for preparing the target compound I-1 except that 3,3-dimethylbutan-2-one was used as the raw material 1 in the step (1) and the step (3) was omitted.

The product was obtained as a white crystal with a yield of 45%. $^1$H NMR (CDCl$_3$, 300 MHz) δ 0.85 (m, 2H, Cyclohexyl-H), 1.02 (s, 9H, 3×CH$_3$), 1.07-1.12 (t, 3H, J=7.5 Hz, CH$_3$), 1.34 (m, 1H, Cyclohexyl-H), 1.67-1.71 (m, 7H, Cyclohexyl-H), 1.84 (m, 1H, Cyclohexyl-H), 2.44-2.47 (d, 2H, J=6.9 Hz, CH$_2$-Cyclohexyl), 2.51-2.56 (m, 2H, CH$_2$), 4.38 (s, 2H, CH$_2$—S), 6.05 (CH, pyrazole-H); $^{13}$C NMR (CDCl$_3$, 75 MHz) δ 13.32, 18.70, 26.34 (2C), 26.44, 28.01 (2C), 30.26 (3C), 31.23, 33.35, 37.35, 41.76, 100.91, 122.76, 142.18, 146.33, 155.36, 156.21, 162.80, 164.32.

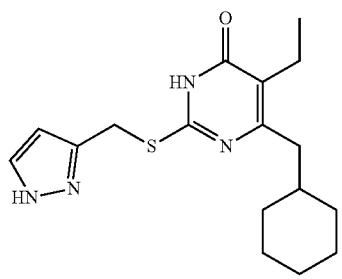

I-31

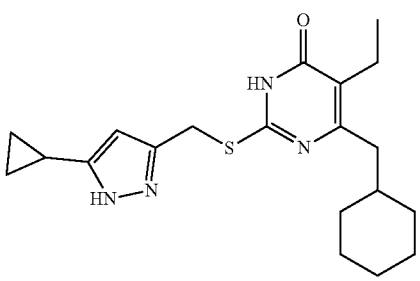

I-33

Compound I-31 was prepared according to method for preparing the target compound I-1 except that acetaldehyde was used as the raw material 1 in the step (1) and the step (3) was omitted.

The product was obtained as a white crystal with a yield of 51%. $^1$H NMR (CDCl$_3$, 300 MHz) δ 1.05 (m, 2H, Cyclohexyl-H), 1.07-1.12 (t, 3H, J=7.5 Hz, CH$_3$), 1.17-1.26 (m, 3H, Cyclohexyl), 1.66-1.70 (m, 5H, Cyclohexyl-H), 1.80-1.85 (m, 1H, Cyclohexyl-H), 2.45-2.47 (d, 2H, J=7.2 Hz, CH$_2$-Cyclohexyl), 2.51-2.53 (m, 2H, CH$_2$), 4.44 (s, 2H, CH$_2$—S), 6.27-6.28 (d, 1H, J=7.5 Hz, pyrazole-H), 7.52-7.53 (d, J=7.5 Hz, 1H, pyrazole-H); $^{13}$C NMR (CDCl$_3$, 75 MHz) δ 13.28, 18.71, 26.31 (2C), 26.41, 27.19 (2C), 33.34, 37.36, 41.74, 104.76, 122.66, 131.71, 140.92, 145.81, 156.11, 163.09, 164.65.

Compound I-33 was prepared according to method for preparing the target compound I-1 except that 1-cyclopropylethanone was used as the raw material 1 in the step (1) and the step (3) was omitted.

The product was obtained as a white crystal with a yield of 38%. 1H NMR (CDCl$_3$, 300 MHz) δ 1.04 (m, 2H, Cyclohexyl-H), 1.07-1.12 (t, 3H, J=7.5 Hz, CH$_3$), 1.17-1.20 (m, 4H, 2×CH$_2$), 1.23-1.26 (m, 3H, Cyclohexyl), 1.66-1.69 (m, 5H, Cyclohexyl-H), 1.82 (m, 1H, Cyclohexyl-H), 1.87-1.94 (m, 1H, cyclopropyl-H), 2.43-2.50 (d, 2H, J=7.5 Hz, CH$_2$-Cyclohexyl), 2.53-2.55 (m, 2H, CH$_2$CH$_3$), 4.36 (s, 2H, CH$_2$—S), 5.88 (CH, pyrazole), 11.72 (br, 2H, NH); $^{13}$C NMR (CDCl$_3$, 75 MHz) δ 7.37, 7.87 (2C), 13.31, 18.69, 26.32 (2C), 26.43, 27.26 (2C), 33.34, 37.36, 41.75, 100.94, 122.59, 146.25, 149.44, 156.37, 163.01, 164.63.

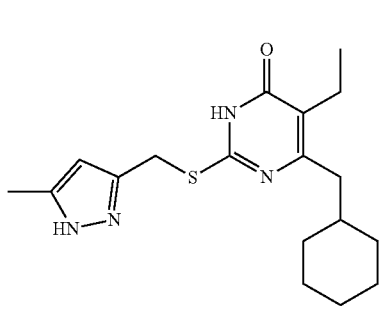

I-32

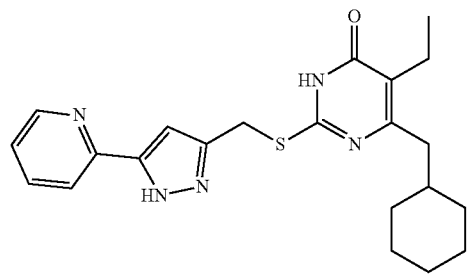

I-34

Compound I-32 was prepared according to method for preparing the target compound I-1 except that acetone was used as the raw material 1 in the step (1) and the step (3) was omitted.

The product was obtained as a white crystal with a yield of 49%. $^1$H NMR (CDCl$_3$, 300 MHz) δ 1.04 (m, 2H, Cyclohexyl-H), 1.07-1.12 (t, 3H, J=7.5 Hz, CH$_3$), 1.16-1.23 (m, 3H, Cyclohexyl-H), 1.66-1.69 (m, 5H, Cyclohexyl-H), 1.80-1.85 (m, 1H, Cyclohexyl-H), 2.30 (s, 3H, CH$_3$-pyrazole), 2.44-2.46 (d, 2H, J=7.2 Hz, CH$_2$-Cyclohexyl), 2.50-2.53 (m, 2H, CH$_2$CH$_3$), 4.37 (s, 2H, CH$_2$—S), 6.02 (CH, pyrazole-H), 11.01-11.45 (br, 2H, NH); $^{13}$C NMR (CDCl$_3$, 75 MHz) δ 11.48, 13.30, 18.68, 26.31, 26.31 (2C), 27.33 (2C), 33.33, 37.33, 41.72, 104.13, 122.59, 141.94, 146.81, 156.33, 163.02, 164.63.

Compound I-34 was prepared according to method for preparing the target compound I-1 except that 2-acetylpyridine was used as the raw material 1 in the step (1) and the step (3) was omitted.

The product was obtained as a white crystal with a yield of 30%. $^1$H NMR (CDCl$_3$, 300 MHz) δ 1.00-1.04 (m, 2H, Cyclohexyl-H), 1.07-1.12 (t, 3H, J=7.5 Hz, CH$_3$), 1.16-1.26 (m, 3H, Cyclohexyl-H), 1.63-1.69 (m, 5H, Cyclohexyl-H), 1.80-1.83 (m, 1H, Cyclohexyl-H), 2.45-2.47 (d, 2H, J=6.9 Hz, CH$_2$-Cyclohexyl), 2.51-2.54 (m, 2H, CH$_2$CH$_3$), 4.49 (s, 2H, CH$_2$—S), 6.75 (s, 1H, pyrazole-H), 7.20-7.21 (m, 1H, pyridine-H), 7.69 (m, 2H, pyridine-H), 8.63-8.64 (m, 1H, pyridine-H), 10.27-10.67 (br, 2H, 2NH); $^{13}$C NMR (CDCl$_3$, 75 MHz) δ 13.32, 18.67, 26.28 (2C), 26.39, 27.08, 27.08, 33.35, 37.38, 41.76, 101.19, 120.31, 122.69, 122.92, 137.01, 145.22, 147.74, 148.91, 149.41, 156.10, 161.87, 164.82.

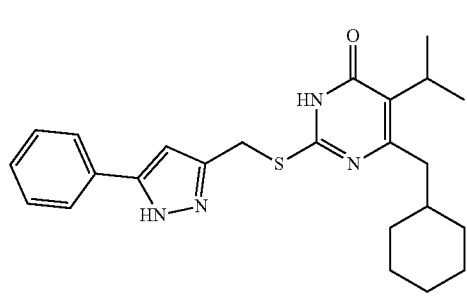

I-35

Compound I-35 was prepared according to method for preparing the target compound I-1 except that the step (3) was omitted and 6-cyclohexylmethyl-5-isopropyl-thiopyrimidone was used as the reactant A in the S-alkylation reaction of the step (6).

The product was obtained as a white crystal with a yield of 78%. $^1$H NMR (CDCl$_3$, 300 MHz) δ 0.76-0.78 (m, 2H, Cyclohexyl-H), 0.97-1.00 (m, 2H, Cyclohexyl-H), 1.07-1.12 (m, 3H, Cyclohexyl-H), 1.26-1.29 (d, 6H, 2CH$_3$) 1.65-1.69 (m, 3H, Cyclohexyl-H), 1.83 (m, 1H, Cyclohexyl-H), 2.41-2.43 (d, 2H, J=7.0 Hz, CH$_2$—Cyclohexyl), 2.86-3.23 (m, 1H, CHMe$_2$), 4.43 (s, 2H, CH$_2$—S), 6.51 (s, 1H, pyrazole-H), 7.32-7.34 (m, 3H, Ph-H), 7.66-7.71 (m, 2H, Ph-H), 10.36 (br, 1H, NH), 13.19 (br, 1H, NH).

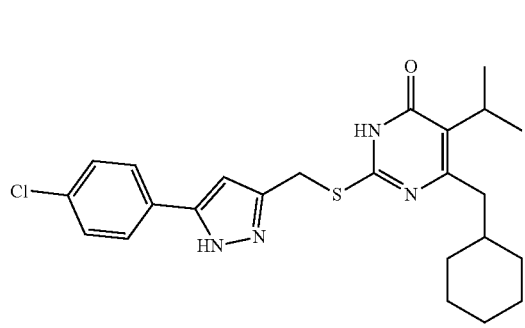

I-36

Compound I-36 was prepared according to method for preparing the target compound I-1 except that 1-(4-chlorophenyl)-acetophenone was used as the raw material 1 in the step (1), the step (3) was omitted and 6-cyclohexylmethyl-5-isopropyl-thiouracil A was used in the S-alkylation reaction of the step (6).

The product was obtained as a white crystal with a yield of 80%. $^1$H NMR (DMSO-d$_6$, 300 MHz) δ 1.01-1.08 (m, 2H, Cyclohexyl-H), 1.18 (m, 3H, Cyclohexyl-H), 1.53 (m, 5H, Cyclohexyl-H), 1.76 (m, 1H, Cyclohexyl-H), 2.35-2.39 (m, 2H, CH$_2$-Cyclohexyl), 2.86-3.19 (m, 1H, CHMe$_2$), 4.35 (s, 2H, CH$_2$—S), 6.57-6.60 (s, 1H, pyrazole-H), 7.26-7.43 (m, 2H, Ph-H), 7.67-7.73 (m, 2H, Ph-H), 12.77 (br, 1H, 2NH).

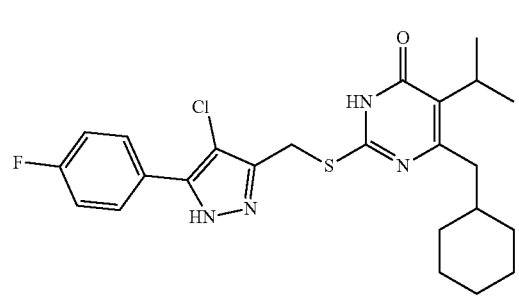

I-37

Compound I-37 was prepared according to method for preparing the target compound I-1 except that 1-(4-fluorophenyl)ethanone was used as the raw material 1 in the step (1) and 6-cyclohexylmethyl-5-isopropyl-thiouracil A was used in the S-alkylation reaction of the step (6).

The product was obtained as a white crystal with a yield of 82%. $^1$H NMR (DMSO-d$_6$, 300 MHz) δ 0.98-1.01 (m, 2H, Cyclohexyl-H), 1.15-1.17 (m, 3H, Cyclohexyl-H), 1.26-1.29 (d, 6H, 2CH$_3$), 1.51-1.57 (m, 5H, Cyclohexyl-H), 1.76 (m, 1H, Cyclohexyl-H), 2.33-2.36 (m, 2H, CH$_2$—Cyclohexyl), 2.86-3.24 (m, 1H, CHMe$_2$), 4.41 (s, 2H, CH$_2$—S), 7.29-7.34 (m, 2H, Ph-H), 7.79-7.82 (m, 2H, Ph-H), 12.96 (br, 2H, 2NH).

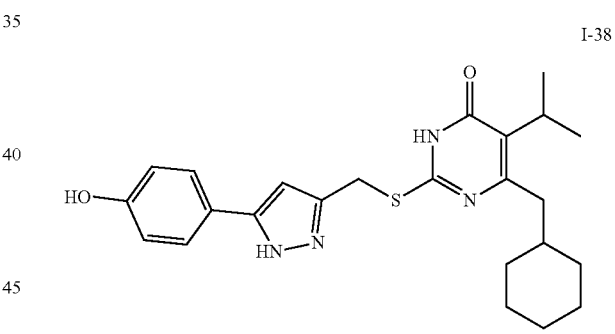

I-38

Compound I-38 was prepared according to method for preparing the target compound I-1 except that 1-(4-hydroxyphenyl)ethanone was used as the raw material 1 in the step (1), the step (3) was omitted and 6-cyclohexylmethyl-5-isopropyl-thiouracil A was used in the S-alkylation reaction of step (6).

The product was obtained as a white crystal with a yield of 64%. $^1$H NMR (DMSO-d$_6$, 300 MHz) δ 0.96-1.10 (m, 5H, Cyclohexyl-H), 1.58-1.60 (m, 5H, Cyclohexyl-H), 1.79 (m, 1H, Cyclohexyl-H), 2.36-2.40 (m, 2H, CH$_2$—Cyclohexyl) 2.86-3.28 (m, 1H, CHMe$_2$), 4.42 (s, 2H, CH$_2$—S), 6.41 (s, 1H, pyrazole-H), 6.77-6.80 (m, 2H, Ph-H), 7.51-7.54 (m, 2H, Ph-H), 9.22 (br, 1H, OH), 12.13 (br, 2H, 2NH).

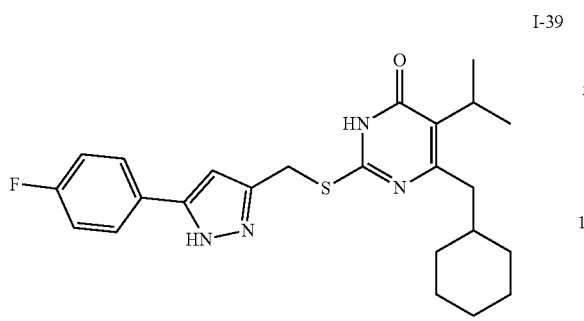

I-39

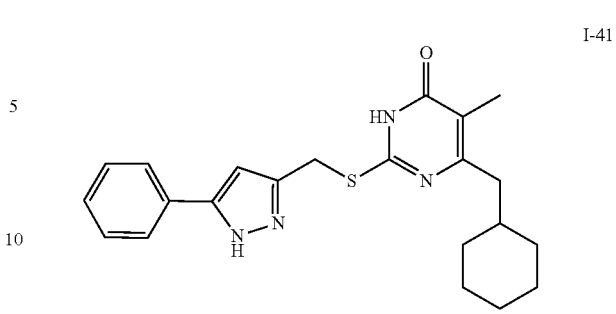

I-41

Compound I-39 was prepared according to method for preparing the target compound I-1 except that 1-(4-fluorophenyl)ethanone was used as the raw material 1 in the step (1), the step (3) was omitted and 6-cyclohexylmethyl-5-isopropyl-thiouracil A was used in the S-alkylation reaction of the step (6).

The product was obtained as a white crystal with a yield of 87%. $^1$H NMR (DMSO-d$_6$, 300 MHz) δ 0.88-0.92 (m, 2H, Cyclohexyl-H), 1.04-1.06 (m, 3H, Cyclohexyl-H), 1.26-1.29 (d, 6H, 2CH$_3$), 1.53-1.58 (m, 5H, Cyclohexyl-H), 1.75 (m, 1H, Cyclohexyl-H), 2.26-2.28 (m, 2H, CH$_2$—Cyclohexyl), 2.86-3.26 (m, 1H, CHMe$_2$), 4.41 (s, 2H, CH$_2$—S), 6.56 (s, 1H, pyrazole-H), 7.17-7.22 (m, 2H, Ph-H), 7.68-7.72 (m, 2H, Ph-H), 12.68 (br, 1H, 2NH).

Compound I-41 was prepared according to method for preparing the target compound I-1 except that the step (3) was omitted and 6-cyclohexylmethyl-5-methyl-thiouracil was used as the reactant A in the S-alkylation reaction of the step (6).

The product was obtained as a white crystal with a yield of 85%. $^1$H NMR (DMSO-d$_6$, 300 MHz) δ 0.94-1.00 (m, 2H, cyclohexyl-H), 1.08-1.11 (m, 3H, Cyclohexyl-H), 1.58-1.73 (m, 6H, Cyclohexyl-H), 1.87 (s, 3H, CH$_3$), 2.39-2.41 (d, 2H, CH$_2$—Cyclohexyl), 4.38 (s, 2H, CH$_2$—S), 6.59 (s, 1H, pyrazole-H), 7.28-7.30 (m, 1H, Ph-H), 7.36-7.41 (t, 2H, J=7.23 Hz, Ph-H), 7.70-7.72 (d, 2H, Ph-H), 12.84 (br, 2H, 2NH).

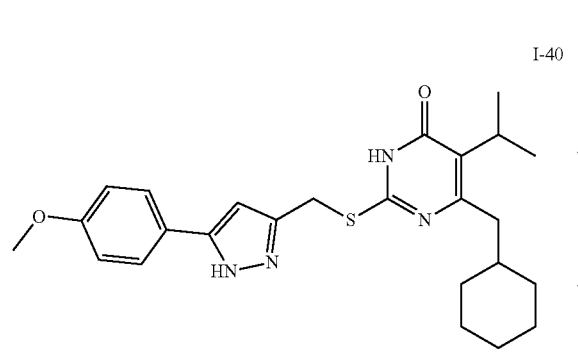

I-40

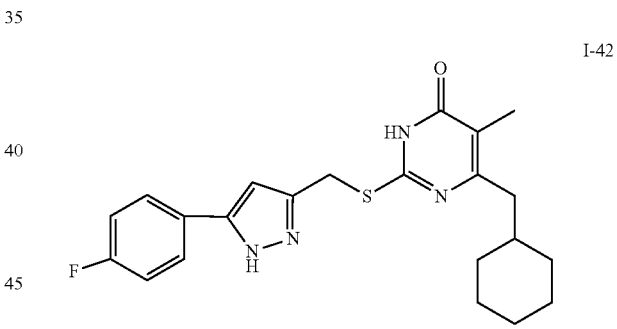

I-42

Compound I-40 was prepared according to method for preparing the target compound I-1 except that 1-(4-methoxyphenyl)ethanone was used as the raw material 1 in the step (1), the step (3) was omitted and 6-cyclohexylmethyl-5-isopropyl-thiouracil A was used in the S-alkylation reaction of the step (6).

The product was obtained as a white crystal with a yield of 50%. $^1$H NMR (DMSO-d$_6$, 300 MHz) δ 0.96-0.98 (m, 2H, Cyclohexyl-H), 1.16-1.21 (m, 3H, Cyclohexyl-H), 1.58-1.62 (m, 5H, Cyclohexyl-H), 1.81 (m, 1H, Cyclohexyl-H), 2.34-2.36 (m, 2H, CH$_2$-Cyclohexyl), 2.84-3.26 (m, 1H, CHMe$_2$), 3.86 (s, 3H, OCH$_3$), 4.39 (s, 2H, CH$_2$—S), 6.47 (s, 1H, pyrazole-H), 6.94-6.97 (m, 2H, Ph-H), 7.61-7.64 (m, 2H, Ph-H), 12.10 (br, 1H, NH).

Compound I-42 was prepared according to method for preparing the target compound I-1 except that 1-(4-fluorophenyl)ethanone was used as the raw material 1 in the step (1), the step (3) was omitted and 6-cyclohexylmethyl-5-methyl-thiouracil A was used in the S-alkylation reaction of the step (6).

The product was obtained as a white crystal with a yield of 87%. $^1$H NMR (DMSO-d$_6$, 300 MHz) δ 0.93-0.97 (m, 2H, Cyclohexyl-H), 1.07-1.10 (m, 3H, Cyclohexyl-H), 1.57-1.60 (m, 6H, Cyclohexyl-H), 1.88 (s, 3H, CH$_3$), 2.38-2.41 (d, 2H, CH$_2$-Cyclohexyl), 4.38 (s, 2H, CH$_2$—S), 6.58 (s, 1H, pyrazole-H), 7.20-7.26 (m, 2H, J=8.8 Hz, Ph-H), 7.73-7.77 (m, 2H, Ph-H), 12.77 (br, 1H, NH).

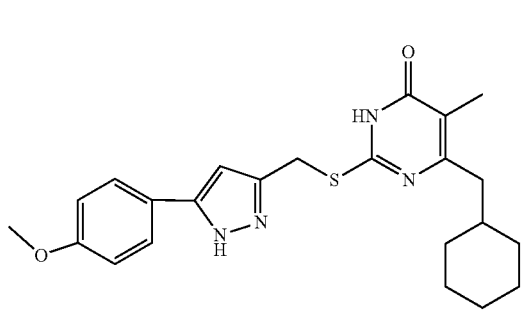

I-43

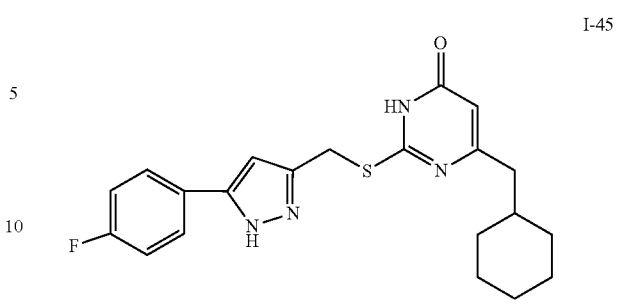

I-45

Compound I-43 was prepared according to method for preparing the target compound I-1 except that 1-(4-methoxyphenyl)ethanone was used as the raw material 1 in the step (1), the step (3) was omitted and 6-cyclohexylmethyl-5-methyl-thiouracil A was used in the S-alkylation reaction of the step (6).

The product was obtained as a white crystal with a yield of 62%. $^1$H NMR (DMSO-d$_6$, 300 MHz) δ 0.95-0.99 (m, 2H, Cyclohexyl-H), 1.11-1.13 (m, 3H, Cyclohexyl-H), 1.59-1.63 (m, 6H, Cyclohexyl-H), 1.88 (s, 3H, CH$_3$), 2.39-2.42 (m, 2H, CH$_2$-Cyclohexyl), 3.77 (s, 3H, OCH$_3$), 4.36 (s, 2H, CH$_2$—S), 6.49 (s, 1H, pyrazole-H), 6.95-6.98 (m, 2H, Ph-H), 7.62-7.65 (m, 2H, Ph-H), 12.70 (br, 2H, 2NH).

Compound I-45 was prepared according to method for preparing the target compound I-1 except that 1-(4-fluorophenyl)ethanone was used as the raw material 1 in the step (1), the step (3) was omitted and 6-cyclohexylmethylthiouracil A was used in the S-alkylation reaction of the step (6).

The product was obtained as a white crystal with a yield of 89%. $^1$H NMR (DMSO-d$_6$, 300 MHz) δ 0.88-0.92 (m, 2H, Cyclohexyl-H), 1.08-1.11 (m, 3H, Cyclohexyl-H), 1.57-1.61 (m, 6H, Cyclohexyl-H), 2.32-2.34 (d, 2H, CH$_2$-Cyclohexyl), 4.40 (s, 2H, CH$_2$—S), 5.96 (s, 1H, Pyrimidone-H), 6.59 (s, 1H, pyrazole-H), 7.20-7.26 (m, 2H, Ph-H), 7.73-7.78 (m, 2H, Ph-H), 12.79 (br, 1H, NH).

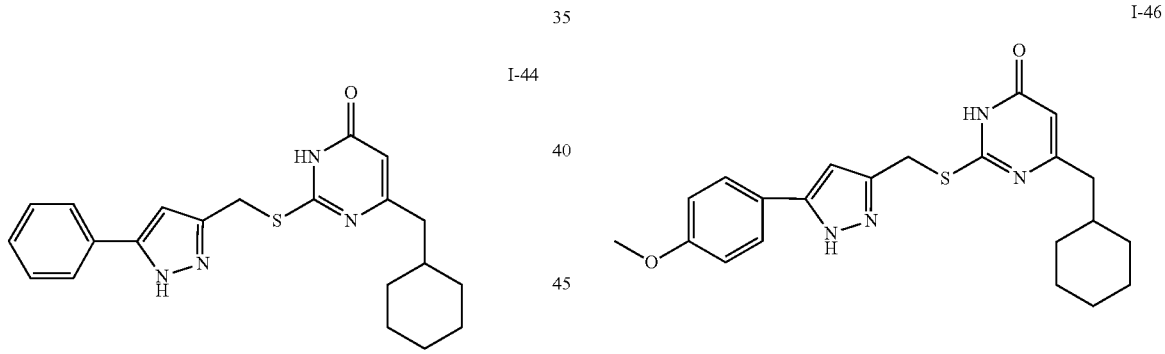

I-44

I-46

Compound I-44 was prepared according to method for preparing the target compound I-1 except that the step (3) was omitted and 6-cyclohexylmethylthiouracil A was used in the S-alkylation reaction of the step (6).

The product was obtained as a white crystal with a yield of 83%. $^1$H NMR (DMSO-d$_6$, 300 MHz) δ 0.89-0.97 (m, 2H, Cyclohexyl-H), 1.09-1.17 (m, 3H, Cyclohexyl-H), 1.58-1.62 (m, 6H, Cyclohexyl-H), 2.32-2.34 (d, 2H, CH$_2$-Cyclohexyl), 4.40 (s, 2H, CH$_2$—S), 5.96 (s, 1H, Pyrimidone-H), 6.61 (s, 1H, pyrazole-H), 7.27-7.32 (t, 1H, J=7.30 Hz, Ph-H), 7.37-7.42 (t, 2H, J=7.47 Hz, Ph-H), 7.70-7.72 (d, 2H, Ph-H), 12.80 (br, 2H, 2NH).

Compound I-46 was prepared according to method for preparing the target compound I-1 except that 1-(4-methoxyphenyl)ethanone was used as the raw material 1 in the step (1), the step (3) was omitted and 6-cyclohexylmethylthiouracil A was used in the S-alkylation reaction of the step (6).

The product was obtained as a white crystal with a yield of 47%. $^1$H NMR (DMSO-d$_6$, 300 MHz) δ 0.90-0.97 (m, 2H, Cyclohexyl-H), 1.10-1.17 (m, 3H, Cyclohexyl), 1.59-1.72 (m, 6H, Cyclohexyl), 2.32-2.3 4 (d, 2H, CH$_2$-Cyclohexyl), 3.77 (s, 3H, OCH3), 4.38 (s, 2H, CH2-S), 5.96 (s, 1H, Pyrimidone-H), 6.50 (s, 1H, pyrazole-H), 6.95-6.98 (d, 2H, Ph-H), 7.62-7.65 (m, 2H, Ph-H), 12.72 (br, 2H, NH).

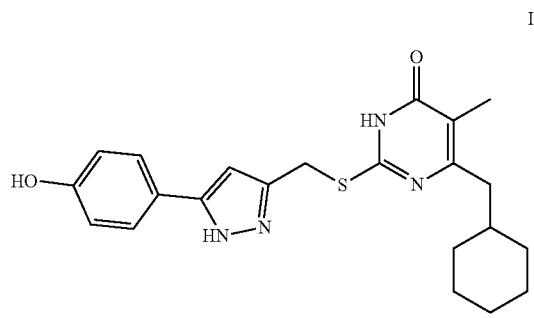

I-47

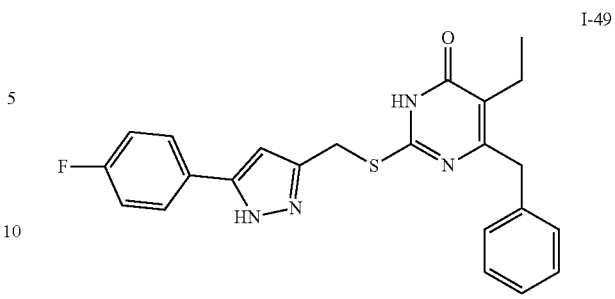

I-49

Compound I-47 was prepared according to method for preparing the target compound I-1 except that 4'-hydroxyacetophenone was used as the raw material 1 in the step (1), the step (3) was omitted and 6-cyclohexylmethyl-5-methyl-thiouracil A was used in the S-alkylation reaction of the step (6).

The product was obtained as a white crystal with a yield of 65%. $^1$H NMR (DMSO-d$_6$, 400 MHz) δ 0.94-1.02 (m, 2H, Cyclohexyl-H), 1.08-1.22 (m, 4H, Cyclohexyl-H), 1.56-1.63 (m, 5H, Cyclohexyl-H), 1.89 (s, 3H, CH$_3$), 2.40-2.42 (d, 2H, J=6.88 Hz, CH$_2$—Cyclohexyl), 4.35 (s, 2H, CH$_2$—S), 6.43 (s, 1H, pyrazole-H), 6.78-6.80 (d, 2H, J=8.52 Hz, Ph-H), 7.50-7.52 (d, 2H, J=8.52 Hz, Ph-H), 9.61 (s, 1H, OH), 12.67 (br, 2H, NH); $^{13}$C NMR (DMSO-d$_6$, 100 MHz) δ 10.99, 26.19 (3C), 26.38 (2C), 33.11, 37.18, 42.02, 101.03, 115.97 (2C), 122.27, 126.90 (2C), 131.69, 137.35, 145.92, 156.77, 157.72, 162.04, 163.75.

Compound I-49 was prepared according to method for preparing the target compound I-1 except that 4'-fluoroacetophenone was used as the raw material 1 in the step (1), the step (3) was omitted and 6-benzyl-5-ethyl-thiouracil A was used in the S-alkylation reaction of the step (6).

The product was obtained as a white crystal with a yield of 83%. $^1$H NMR (DMSO-d$_6$, 400 MHz) δ 0.93-0.96 (t, 3H, J=7.3 Hz, CH$_2$—CH$_3$), 2.44-2.47 (m, 2H, CH$_2$—CH$_3$), 3.92 (s, 2H, CH$_2$-Ph), 4.36 (s, 2H, CH$_2$—S), 6.41 (s, 1H, pyrazole-H), 7.17-7.30 (m, 7H, Ph-H), 7.69-7.73 (m, 2H, Ph-H), 12.80 (br, 2H, NH); $^{13}$C NMR (DMSO-d$_6$, 100 MHz) δ 13.57, 18.71, 25.70, 40.15, 102.15, 116.09 (2C), 121.68, 126.70, 127.50 (2C), 128.80 (2C), 129.33 (2C), 133.41, 138.99, 141.63, 145.36, 148.50, 157.30, 160.94, 163.37.

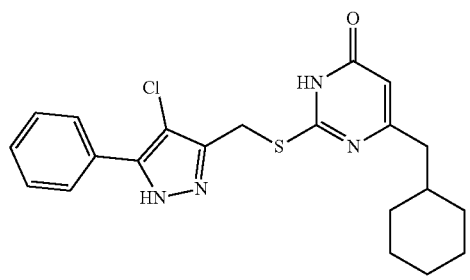

I-48

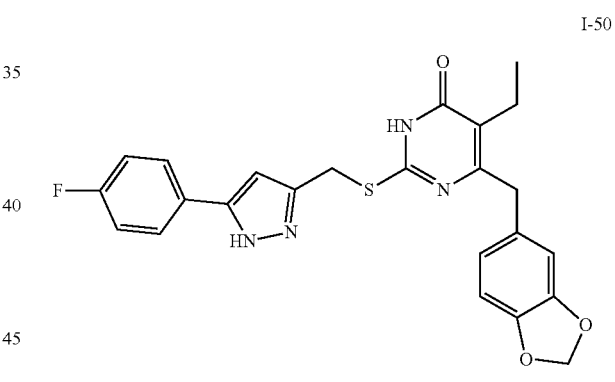

I-50

Compound I-48 was prepared according to method for preparing the target compound I-1 except that 6-cyclohexylmethyl-thiouracil A was used in the S-alkylation reaction of the step (6).

The product was obtained as a white crystal with a yield of 44%. $^1$H NMR (DMSO-d$_6$, 400 MHz) δ 0.85-0.93 (m, 2H, Cyclohexyl-H), 1.01-1.18 (m, 3H, Cyclohexyl-H), 1.53-1.58 (m, 5H, Cyclohexyl-H), 1.67-1.71 (m, 1H, Cyclohexyl-H), 2.30-2.32 (d, 2H, J=7.00 Hz, CH$_2$—Cyclohexyl), 4.46 (s, 2H, CH$_2$—S), 5.96 (s, 1H, Pyrimidone-H), 7.39-7.43 (t, 1H, J=7.32 Hz, Ph-H), 7.47-7.51 (t, 2H, J=7.44 Hz, Ph-H), 7.78-7.80 (d, 2H, J=7.56 Hz, Ph-H), 13.19 (br, 2H, NH); $^{13}$C NMR (DMSO-d$_6$, 100 MHz) δ 26.03 (3C), 26.37 (2C), 32.89, 36.60, 44.70, 105.66, 107.62, 126.96 (2C), 128.96, 129.22, 132.95, 138.53, 141.39, 152.49, 157.05, 162.06, 164.69.

Compound I-50 was prepared according to method for preparing the target compound I-1 except that 4'-fluoroacetophenone was used as the raw material 1 in the step (1), the step (3) was omitted and 6-(benzo[d][1,3]dioxol-5-ylmethyl)-5-ethyl-thiouracil A was used in the S-alkylation reaction of the step (6).

The product was obtained as a white crystal with a yield of 76%. $^1$H NMR (DMSO-d$_6$, 400 MHz) δ 0.93-0.97 (t, 3H, J=7.3 Hz, CH$_2$—CH$_3$), 2.43-2.48 (m, 2H, CH$_2$—CH$_3$), 3.83 (s, 2H, CH$_2$-Ph), 4.38 (s, 2H, CH$_2$—S), 5.90 (s, 2H, O—CH$_2$—O), 6.45 (s, 1H, pyrazole-H), 6.74-6.80 (m, 2H, Ph-H), 6.87 (s, 1H, Ph-H), 7.22-7.26 (t, 2H, J=8.8 Hz, Ph-H), 7.70-7.73 (m, 2H, Ph-H), 12.77 (br, 2H, NH); $^{13}$C NMR (DMSO-d$_6$, 100 MHz) δ 13.62, 18.63, 25.43, 39.67, 101.16, 102.11, 108.57, 109.77, 116.07 (2C), 121.52, 122.23, 127.47, 129.38, 132.63, 135.07, 140.08, 143.08, 146.07, 147.61, 154.08, 157.17, 160.93, 163.36.

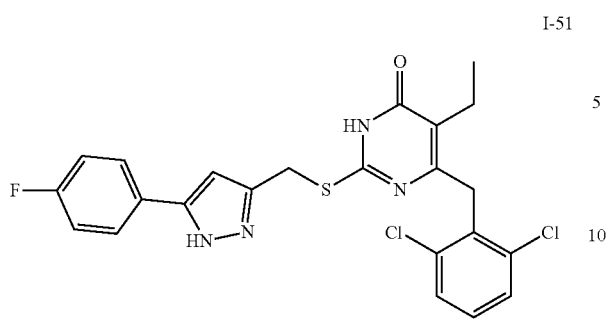

I-51

Compound I-51 was prepared according to method for preparing the target compound I-1 except that 4'-fluoroacetophenone was used as the raw material 1 in the step (1), the step (3) was omitted and 6-(2',6'-dichlorobenzyl)-5-ethyl-thiouracil A was used in the S-alkylation reaction of the step (6).

The product was obtained as a white crystal with a yield of 62%. $^1$H NMR (DMSO-d$_6$, 400 MHz) δ 1.09-1.13 (t, 3H, J=7.0 Hz, CH$_2$—CH$_3$), 2.56-2.58 (m, 2H, CH$_2$—CH$_3$), 3.98 (s, 2H, CH$_2$-Ph), 4.26 (s, 2H, CH$_2$—S), 6.00 (s, 1H, pyrazole-H), 7.18-7.29 (m, 3H, Ph-H), 7.42-7.44 (d, 2H, J=7.96 Hz, Ph-H), 7.67-7.71 (m, 2H, Ph-H), 12.80 (br, 2H, NH); $^{13}$C NMR (DMSO-d$_6$, 100 MHz) δ 13.06, 18.39, 35.24, 43.13, 101.62, 116.14 (2C), 127.48 (2C), 128.48 (2C), 129.52, 135.05, 136.12 (2C), 139.48, 140.40, 142.88, 149.36, 151.11, 157.83, 160.93, 163.36.

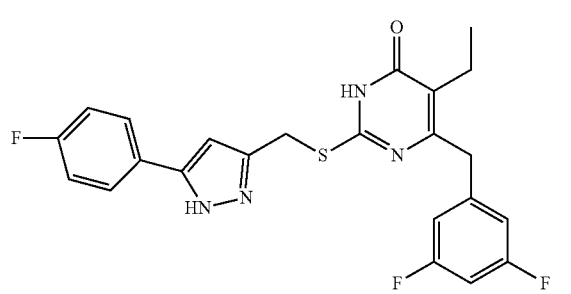

I-52

Compound I-52 was prepared according to method for preparing the target compound I-1 except that 4'-fluoroacetophenone was used as the raw material 1 in the step (1), the step (3) was omitted and 6-(3',5'-difluorobenzyl)-5-ethyl-thiouracil A was used in the S-alkylation reaction of the step (6).

The product was obtained as a white crystal with a yield of 78%. $^1$H NMR (DMSO-d$_6$, 400 MHz) δ 0.93-0.97 (t, 3H, J=7.3 Hz, CH$_2$—CH$_3$), 2.45-2.49 (m, 2H, CH$_2$—CH$_3$), 3.96 (s, 2H, CH$_2$-Ph), 4.34 (s, 2H, CH$_2$—S), 6.41 (s, 1H, pyrazole-H), 7.01-7.06 (m, 3H, Ph-H), 7.21-7.26 (t, 2H, J=8.8 Hz, Ph-H), 7.67-7.71 (m, 2H, Ph-H), 12.80 (br, 2H, NH); $^{13}$C NMR (DMSO-d$_6$, 100 MHz) δ 13.55, 18.60, 25.76, 39.42, 102.01, 102.39, 112.56 (2C), 115.98 (2C), 121.97, 127.45 (2C), 139.46, 143.50, 149.37, 154.05, 157.54, 159.39, 160.93, 161.46, 163.36, 163.90.

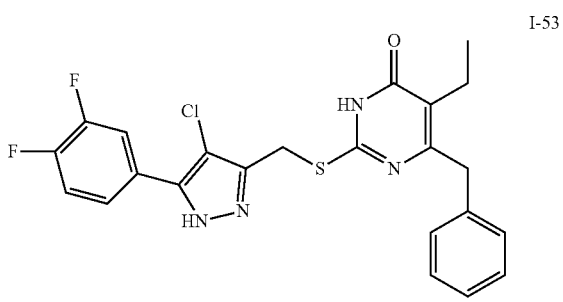 [SMILES: CCc1c(Cc2ccccc2)nc(SCc2n[nH]c(-c3ccc(F)c(F)c3)c2Cl)[nH]c1=O]

I-53

Compound I-53 was prepared according to method for preparing the target compound I-1 except that 3',4'-difluoroacetophenone was used as the raw material 1 in the step (1) and 6-benzyl-5-ethyl-thiouracil A was used in the S-alkylation reaction of the step (6).

The product was obtained as a white crystal with a yield of 72%. $^1$H NMR (DMSO-d$_6$, 400 MHz) δ 0.89-0.92 (t, 3H, J=7.3 Hz, CH$_2$—CH$_3$), 2.41-2.47 (m, 2H, CH$_2$—CH$_3$), 3.90 (s, 2H, CH$_2$-Ph), 4.43 (s, 2H, CH$_2$—S), 7.14-7.17 (m, 1H, Ph-H), 7.21-7.27 (m, 4H, Ph-H), 7.54-7.65 (m, 2H, Ph-H), 7.75-7.80 (m, 1H, Ph-H), 13.06 (br, 2H, NH); $^{13}$C NMR (DMSO-d$_6$, 100 MHz), δ 13.46, 18.67, 24.01, 40.12, 105.95, 116.04, 118.56, 121.68, 124.01, 126.64, 128.73 (2C), 129.20 (2C), 136.42, 138.98, 143.77, 146.08, 148.68, 151.12, 156.83, 160.89, 163.76.

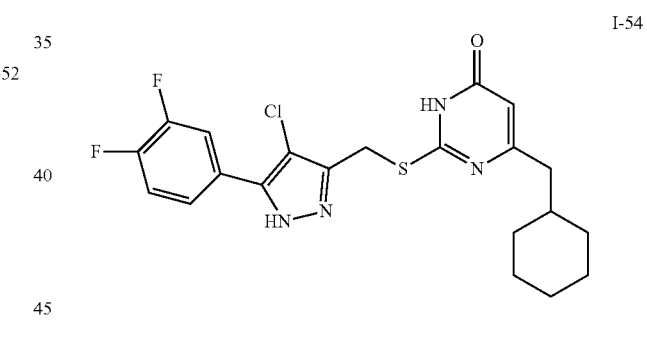

I-54

Compound I-54 was prepared according to method for preparing the target compound I-1 except that 3',4'-difluoroacetophenone was used as the raw material 1 in the step (1) and 6-cyclohexylmethyl-thiouracil A was used in the S-alkylation reaction of the step (6).

The product was obtained as a white crystal with a yield of 67%. $^1$H NMR (DMSO-d$_6$, 400 MHz) δ 0.84-0.92 (m, 2H, Cyclohexyl-H), 1.06-1.19 (m, 3H, Cyclohexyl-H), 1.54-1.66 (m, 6H, Cyclohexyl-H), 2.30-2.32 (d, 2H, J=6.9 Hz, CH$_2$-Cyclohexyl), 4.45 (s, 2H, CH$_2$—S), 5.97 (s, 1H, Pyrimidone-H), 7.55-7.61 (m, 1H, Ph-H), 7.66-7.68 (m, 1H, Ph-H), 7.76-7.82 (m, 1H, Ph-H), 13.48 (br, 2H, NH); $^{13}$C NMR (DMSO-d$_6$, 100 MHz) δ 26.00 (3C), 26.35 (2C), 32.86, 36.61, 44.73, 105.89, 107.67, 115.87, 118.55, 123.96, 131.36, 136.14, 140.00, 148.68, 151.12, 155.79, 161.40, 164.00.

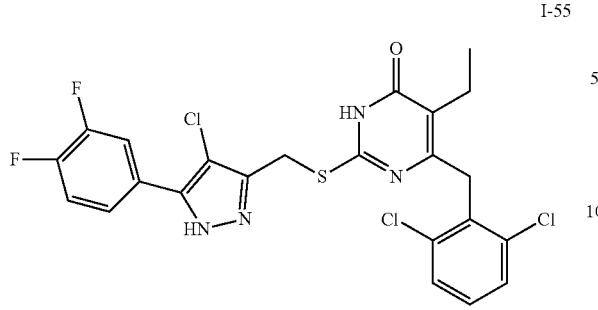

I-55

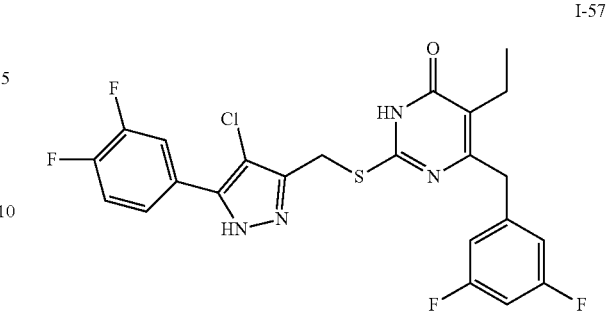

I-57

Compound I-55 was prepared according to method for preparing the target compound I-1 except that 3',4'-difluoroacetophenone was used as the raw material 1 in the step (1) and 6-(2',6'-dichlorobenzyl)-5-ethyl-thiouracil A was used in the S-alkylation reaction of the step (6).

The product was obtained as a white crystal with a yield of 79%. $^1$H NMR (DMSO-$d_6$, 400 MHz) δ 1.09-1.13 (m, 3H, CH$_2$—CH$_3$), 2.56-2.57 (m, 2H, CH$_2$—CH$_3$), 3.96 (s, 2H, CH$_2$-Ph), 4.23 (s, 2H, CH$_2$—S), 7.22-7.26 (m, 1H, Ph-H), 7.39-7.42 (m, 2H, Ph-H), 7.58-7.62 (m, 2H, Ph-H), 7.74-7.79 (m, 1H, Ph-H), 13.12 (br, 2H, NH); $^{13}$C NMR (DMSO-$d_6$, 100 MHz) δ 13.06, 18.36, 24.59, 35.16, 105.76, 115.97, 118.70, 124.04, 128.37 (2C), 129.39, 131.39, 134.95, 136.04 (2C), 138.15, 144.28, 148.76, 149.88, 151.08, 155.79, 159.86, 163.23.

Compound I-57 was prepared according to method for preparing the target compound I-1 except that 3',4'-difluoroacetophenone was used as the raw material 1 in the step (1) and 6-(3',5'-difluorobenzyl)-5-ethyl-thiouracil A was used in the S-alkylation reaction of the step (6).

The product was obtained as a white crystal with a yield of 62%. $^1$H NMR (DMSO-$d_6$, 400 MHz) δ 0.89-0.93 (t, 3H, J=7.4 Hz, CH$_2$—CH$_3$), 2.40-2.46 (m, 2H, CH$_2$—CH$_3$), 3.95 (s, 2H, CH$_2$-Ph), 4.39 (s, 2H, CH$_2$—S), 6.95-7.03 (m, 3H, Ph-H), 7.53-7.65 (t, 2H, Ph-H), 7.74-7.78 (m, 1H, Ph-H), 13.31 (br, 2H, NH); $^{13}$C NMR (DMSO-$d_6$, 100 MHz), δ 13.49, 18.58, 23.69, 39.98, 102.18, 105.82, 112.37 (2C), 115.88, 118.51, 123.93, 128.26, 132.09, 135.06, 137.44, 143.50 (2C), 146.51, 148.59, 151.04, 157.69, 161.41, 163.86.

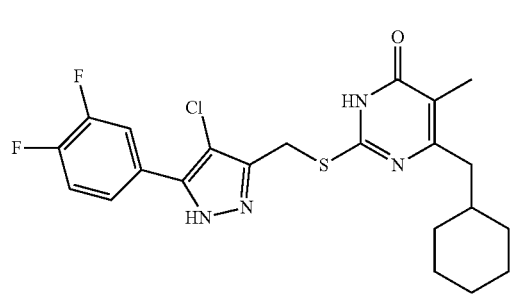

I-56

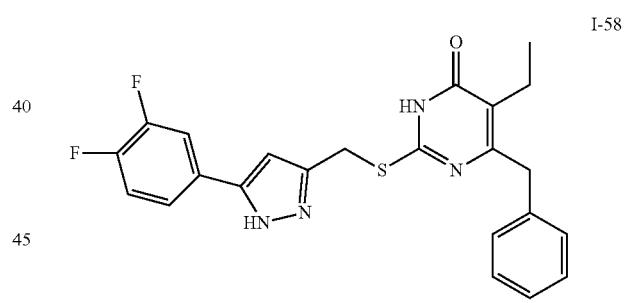

I-58

Compound I-56 was prepared according to method for preparing the target compound I-1 except that 3',4'-difluoroacetophenone was used as the raw material 1 in the step (1) and 6-cyclohexylmethyl-5-methyl-thiouracil A was used in the S-alkylation reaction of the step (6).

The product was obtained as a white crystal with a yield of 54%. $^1$H NMR (DMSO-$d_6$, 400 MHz) δ 0.92-0.94 (m, 2H, Cyclohexyl-H), 1.05-1.07 (m, 3H, Cyclohexyl-H), 1.54-1.67 (m, 6H, Cyclohexyl-H), 1.87 (s, 3H, CH$_3$), 2.37-2.39 (d, 2H, J=6.9 Hz, CH$_2$—Cyclohexyl), 4.43 (s, 2H, CH$_2$—S), 7.56-7.61 (m, 1H, Ph-H), 7.67-7.69 (m, 1H, Ph-H), 7.78-7.83 (m, 1H, Ph-H), 13.28 (br, 2H, NH); $^{13}$C NMR (DMSO-$d_6$, 100 MHz), δ 10.94, 26.14 (3C), 26.35 (2C), 33.01, 37.16, 41.87, 105.78, 115.86, 118.53, 123.93, 130.67, 137.17, 141.50, 145.16, 148.66, 151.04, 155.40, 161.08, 163.99.

Compound I-58 was prepared according to method for preparing the target compound I-1 except that 3',4'-difluoroacetophenone was used as the raw material 1 in the step (1), the step (3) was omitted and 6-benzyl-5-ethyl-thiouracil A was used in the S-alkylation reaction of the step (6).

The product was obtained as a white crystal with a yield of 76%. $^1$H NMR (DMSO-$d_6$, 400 MHz) δ 0.92-0.96 (t, 3H, J=7.3 Hz, CH$_2$—CH$_3$), 2.43-2.47 (m, 2H, CH$_2$—CH$_3$), 3.92 (s, 2H, CH$_2$-Ph), 4.37 (s, 2H, CH$_2$—S), 6.49 (s, 1H, pyrazole-H), 7.16-7.19 (m, 1H, Ph-H), 7.23-7.29 (m, 4H, Ph-H), 7.44-7.54 (m, 2H, Ph-H), 7.70-7.75 (m, 1H, Ph-H), 12.83 (br, 2H, NH); $^{13}$C NMR (DMSO-$d_6$, 100 MHz) δ 13.55, 18.70, 24.32, 40.14, 102.62, 114.35, 118.36, 122.23, 126.69, 128.78 (2C), 129.33 (2C), 131.66, 139.01, 142.37, 148.10, 148.91, 150.48, 151.34, 156.80, 160.86, 163.55.

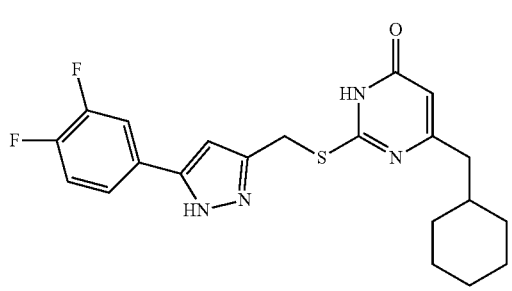

I-59

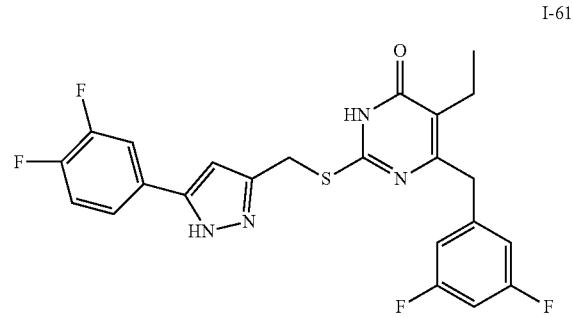 [SMILES: CCc1c(Cc2cc(F)cc(F)c2)nc(SCc2n[nH]c(-c3ccc(F)c(F)c3)c2Cl)[nH]c1=O]

I-61

Compound I-59 was prepared according to method for preparing the target compound I-1 except that 3',4'-difluoroacetophenone was used as the raw material 1 in the step (1), the step (3) was omitted and 6-cyclohexylmethyl-thiouracil A was used in the S-alkylation reaction of the step (6).

The product was obtained as a white crystal with a yield of 82%. $^1$H NMR (DMSO-d$_6$, 400 MHz) δ 0.83-0.94 (m, 2H, Cyclohexyl-H), 1.05-1.18 (m, 3H, Cyclohexyl-H), 1.54-1.67 (m, 6H, Cyclohexyl-H), 2.31-2.33 (d, 2H, J=6.9 Hz, CH$_2$-Cyclohexyl), 4.40 (s, 2H, CH$_2$—S), 5.96 (s, 1H, Pyrimidone-H), 6.67 (s, 1H, pyrazole-H), 7.42-7.49 (m, 1H, Ph-H), 7.57-7.60 (m, 1H, Ph-H), 7.74-7.79 (m, 1H, Ph-H), 12.80 (br, 2H, NH); $^{13}$C NMR (DMSO-d$_6$, 100 MHz), δ 26.02 (3C), 26.35 (2C), 32.90, 36.65, 44.87, 102.69, 107.73, 114.35, 118.34, 112.17, 130.37, 136.04, 139.42, 148.51, 150.95, 155.06, 164.34, 167.35.

Compound I-61 was prepared according to method for preparing the target compound I-1 except that 3',4'-difluoroacetophenone was used as the raw material 1 in the step (1), the step (3) was omitted and 6-(3',5'-difluorobenzyl)-5-ethyl-thiouracil A was used in the S-alkylation reaction of the step (6).

The product was obtained as a white crystal with a yield of 82%. $^1$H NMR (DMSO-d$_6$, 400 MHz) δ 0.92-0.96 (t, 3H, J=7.3 Hz, CH$_2$—CH$_3$), 2.42-2.48 (m, 2H, CH$_2$—CH$_3$), 3.96 (s, 2H, CH$_2$-Ph), 4.35 (s, 2H, CH$_2$—S), 6.49 (s, 1H, pyrazole-H), 6.99-7.03 (m, 3H, Ph-H), 7.42-7.49 (m, 1H, Ph-H), 7.52-7.55 (m, 1H, Ph-H), 7.69-7.74 (m, 1H, Ph-H), 12.86 (br, 2H, NH); $^{13}$C NMR (DMSO-d$_6$, 100 MHz) δ 13.51, 18.59, 25.23, 39.44, 102.24, 102.51, 112.53 (2C), 114.33, 118.29, 122.15, 130.72, 134.39, 137.46, 140.05, 143.51, 145.42, 148.49, 150.93, 159.52, 161.44, 163.88 (2C).

I-60

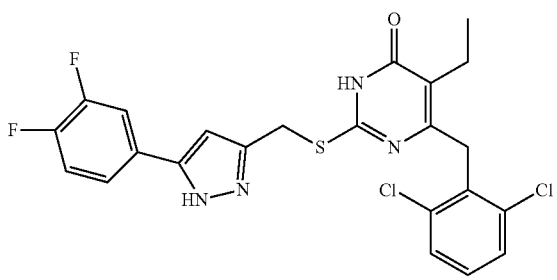

I-62

Compound I-60 was prepared according to method for preparing the target compound I-1 except that 3',4'-difluoroacetophenone was used as the raw material 1 in the step (1), the step (3) was omitted and 6-(2',6'-dichlorobenzyl)-5-ethyl-thiouracil A was used in the S-alkylation reaction of the step (6).

The product was obtained as a white crystal with a yield of 73%. $^1$H NMR (DMSO-d$_6$, 400 MHz) δ 1.09-1.13 (t, 3H, J=7.1 Hz, CH$_2$—CH$_3$), 2.54-2.59 (m, 2H, CH$_2$—CH$_3$), 3.99 (s, 2H, CH$_2$-Ph), 4.24-4.26 (m, 2H, CH$_2$—S), 6.08 (s, 1H, pyrazole-H), 7.20-7.24 (m, 1H, Ph-H), 7.40-7.43 (m, 2H, Ph-H), 7.49-7.50 (m, 2H, Ph-H), 7.66-7.71 (m, 1H, Ph-H), 12.81 (br, 2H, NH); $^{13}$C NMR (DMSO-d$_6$, 100 MHz) δ 13.04, 18.38, 24.43, 35.22, 102.11, 114.28, 118.41, 122.25, 128.46 (2C), 129.52, 135.03, 136.10 (2C), 141.49, 144.77, 148.11, 148.91, 150.58, 151.34, 157.94, 160.84, 163.30.

Compound I-62 was prepared according to method for preparing the target compound I-1 except that 3',4'-difluoroacetophenone was used as the raw material 1 in the step (1), the step (3) was omitted and 6-(1',3'-benzodioxy)-5-ethyl-thiouracil A was used in the S-alkylation reaction of the step (6).

The product was obtained as a white crystal with a yield of 85%. $^1$H NMR (DMSO-d$_6$, 400 MHz) δ 0.92-0.96 (t, 3H, J=7.3 Hz, CH$_2$—CH$_3$), 2.42-2.47 (m, 2H, CH$_2$—CH$_3$), 3.83 (s, 2H, CH$_2$-Ph), 4.38 (s, 2H, CH$_2$—S), 5.89 (s, 2H, O—CH$_2$—O), 6.53 (s, 1H, pyrazole-H), 6.73-6.79 (m, 2H, Ph-H), 6.85 (s, 1H, Ph-H), 7.43-7.53 (m, 2H, Ph-H), 7.71-7.76 (m, 1H, Ph-H), 12.81 (br, 2H, NH); $^{13}$C NMR (DMSO-d$_6$, 100 MHz) δ 13.59, 18.62, 25.54, 39.66, 101.15, 102.60, 108.54, 109.75, 114.36, 118.32, 122.22 (2C), 132.63, 136.00, 138.70, 142.21, 146.05, 147.60, 148.13, 148.91, 150.47, 151.34, 161.01, 163.70.

I-63

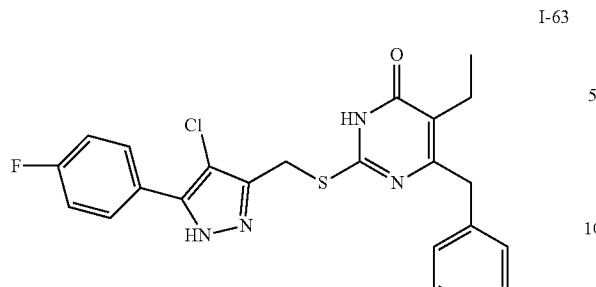

Compound I-63 was prepared according to method for preparing the target compound I-1 except that 4'-fluoroacetophenone was used as the raw material 1 in the step (1) and 6-(3',5'-difluorobenzyl)-5-ethyl-thiouracil A was used in the S-alkylation reaction of the step (6).

The product was obtained as a white crystal with a yield of 77%. $^1$H NMR (DMSO-d$_6$, 400 MHz) δ 0.91-0.94 (t, 3H, J=7.3 Hz, CH$_2$—CH$_3$), 2.42-2.47 (m, 2H, CH$_2$—CH$_3$), 3.95 (s, 2H, CH$_2$-Ph), 4.39 (s, 2H, CH$_2$—S), 6.97-7.04 (m, 3H, Ph-H), 7.31-7.36 (t, 2H, J=8.6 Hz, Ph-H), 7.78-7.82 (m, 2H, Ph-H), 12.98 (br, 2H, NH); $^{13}$C NMR (DMSO-d$_6$, 100 MHz) δ 13.50, 18.58, 24.50, 39.40, 102.20, 105.50, 112.44 (2C), 116.21 (2C), 122.14, 129.17 (2C), 138.96, 143.46, 149.22, 152.52, 156.05, 159.35, 161.26, 161.43, 163.71, 163.87.

I-64

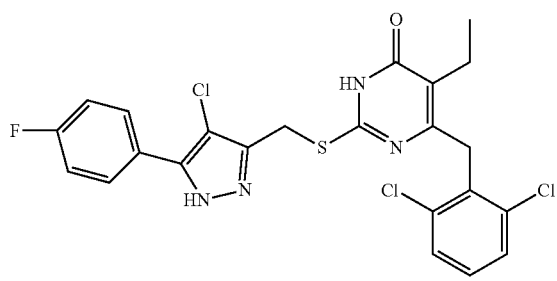

Compound I-64 was prepared according to method for preparing the target compound I-1 except that 4'-fluoroacetophenone was used as the raw material 1 in the step (1) and 6-(2',6'-difluorobenzyl)-5-ethyl-thiouracil A was used in the S-alkylation reaction of the step (6).

The product was obtained as a white crystal with a yield of 72%. $^1$H NMR (DMSO-d$_6$, 400 MHz) δ 1.08-1.12 (t, 3H, J=7.3 Hz, CH$_2$—CH$_3$), 2.54-2.59 (m, 2H, CH$_2$—CH$_3$), 3.95 (s, 2H, CH$_2$-Ph), 4.22 (s, 2H, CH$_2$—S), 7.22-7.26 (t, 1H, J=8.2 Hz, Ph-H), 7.33-7.45 (m, 4H, Ph-H), 7.77-7.81 (m, 2H, Ph-H), 12.91 (br, 2H, NH); $^{13}$C NMR (DMSO-d$_6$, 100 MHz) δ 13.06, 18.37, 24.31, 35.56, 105.40, 116.31 (2C), 128.37 (2C), 129.23 (2C), 129.38, 134.98, 136.06 (2C), 138.83, 139.55, 142.29, 148.66, 151.76, 158.26, 161.31, 163.75.

I-65

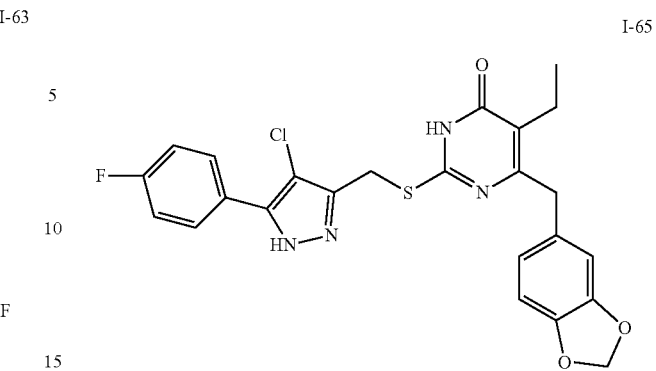

Compound I-65 was prepared according to method for preparing the target compound I-1 except that 4'-fluoroacetophenone was used as the raw material 1 in the step (1) and 6-(1',3'-benzodioxy)-5-ethyl-thiouracil A was used in the S-alkylation reaction of the step (6).

The product was obtained as a white crystal with a yield of 83%. $^1$H NMR (DMSO-d$_6$, 400 MHz) δ 0.90-0.94 (t, 3H, J=7.3 Hz, CH$_2$—CH$_3$), 2.41-2.46 (m, 2H, CH$_2$—CH$_3$), 3.81 (s, 2H, CH$_2$-Ph), 4.44 (s, 2H, CH$_2$—S), 5.92 (s, 2H, O—CH$_2$—O), 6.73-6.80 (m, 2H, Ph-H), 6.83 (s, 1H, Ph-H), 7.32-7.36 (m, 2H, Ph-H), 7.80-7.84 (m, 2H, Ph-H), 13.06 (br, 2H, NH); $^{13}$C NMR (DMSO-d$_6$, 100 MHz) δ 13.53, 18.62, 24.09, 39.66, 101.16, 105.59, 108.48, 109.61, 116.22 (2C), 121.38, 122.15, 126.59, 129.21 (2C), 132.60, 139.72, 142.56, 146.06, 147.59, 153.95, 157.36, 161.27, 163.71.

I-66

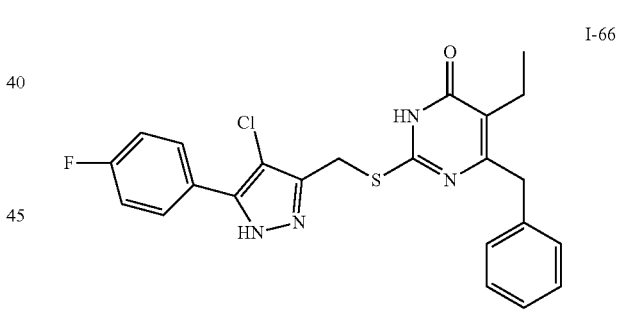

Compound I-66 was prepared according to method for preparing the target compound I-1 except that 4'-fluoroacetophenone was used as the raw material 1 in the step (1) and 6-benzyl-5-ethyl-thiouracil A was used in the S-alkylation reaction of the step (6).

The product was obtained as a white crystal with a yield of 79%. $^1$H NMR (DMSO-d$_6$, 400 MHz) δ 0.90-0.93 (t, 3H, J=7.3 Hz, CH$_2$—CH$_3$), 2.42-2.48 (m, 2H, CH$_2$—CH$_3$), 3.90 (s, 2H, CH$_2$-Ph), 4.43 (s, 2H, CH$_2$—S), 7.14-7.17 (t, 1H, J=7.0 Hz, Ph-H), 7.22-7.25 (t, 2H, J=7.6 Hz, Ph-H), 7.27-7.29 (d, 2H, J=7.2 Hz, Ph-H), 7.32-7.36 (t, 2H, J=8.7 Hz, Ph-H), 7.81-7.84 (m, 2H, Ph-H), 12.97 (br, 2H, NH); $^{13}$C NMR (DMSO-d$_6$, 100 MHz) δ 13.48, 18.69, 24.30, 40.17, 105.60, 116.25 (2C), 121.49, 126.64, 128.73 (2C), 129.25 (4C), 133.92, 138.97, 140.12, 144.11, 148.84, 156.97, 161.28, 163.72.

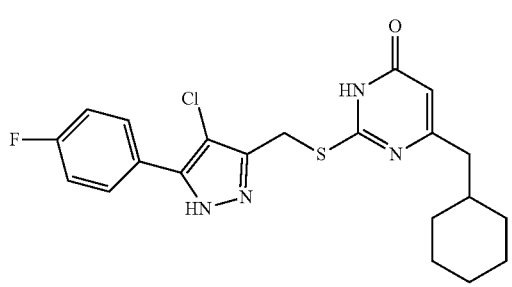

I-67

Compound I-67 was prepared according to method for preparing the target compound I-1 except that 4'-fluoroacetophenone was used as the raw material 1 in the step (1) and 6-cyclohexylmethyl-thiouracil A was used in the S-alkylation reaction of the step (6).

The product was obtained as a white crystal with a yield of 68%. $^1$H NMR (DMSO-d$_6$, 400 MHz) δ 0.84-0.92 (m, 2H, Cyclohexyl-H), 1.03-1.11 (m, 3H, Cyclohexyl-H), 1.55-1.69 (m, 6H, Cyclohexyl-H), 2.30-2.32 (d, 2H, J=7.0 Hz, CH$_2$-Cyclohexyl), 4.45 (s, 2H, CH$_2$—S), 5.96 (s, 1H, Pyrimidone-H), 7.32-7.36 (t, 2H, J=8.8 Hz, Ph-H), 7.81-7.84 (m, 2H, Ph-H), 13.09 (br, 2H, NH); $^{13}$C NMR (DMSO-d$_6$, 100 MHz) δ 26.02 (3C), 26.35, 32.87, 36.59, 44.71, 105.56, 107.69, 116.21 (2C), 126.33, 129.15 (2C), 138.01, 142.77, 148.11, 158.68, 161.25, 163.70, 167.53.

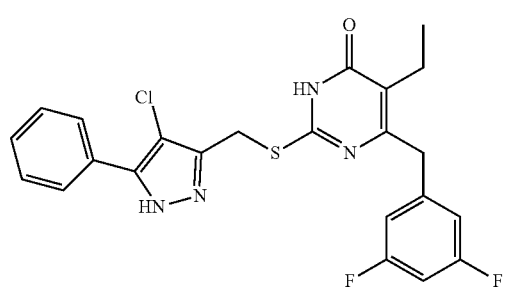

I-69

Compound I-69 was prepared according to method for preparing the target compound I-1 except that 6-(3',5'-difluorobenzyl)-5-ethyl-thiouracil A was used in the S-alkylation reaction of the step (6).

The product was obtained as a white crystal with a yield of 82%. $^1$H NMR (DMSO-d$_6$, 400 MHz) δ 0.92-0.95 (t, 3H, J=7.3 Hz, CH$_2$—CH$_3$), 2.42-2.48 (m, 2H, CH$_2$—CH$_3$), 3.95 (s, 2H, CH$_2$-Ph), 4.40 (s, 2H, CH$_2$—S), 6.99-7.04 (m, 3H, Ph-H), 7.39-7.43 (t, 1H, J=7.2 Hz, Ph-H), 7.47-7.51 (t, 2H, J=7.4 Hz, Ph-H), 7.75-7.77 (d, 2H, J=7.5 Hz, Ph-H), 12.94 (br, 2H, NH); $^{13}$C NMR (DMSO-d$_6$, 100 MHz) δ 13.53, 18.58, 24.45, 39.41, 102.21, 105.61, 112.48 (2C), 122.13, 126.90 (2C), 129.02, 129.23 (2C), 133.45, 138.70, 143.46, 149.82, 154.63, 156.71, 159.40, 161.44, 163.68.

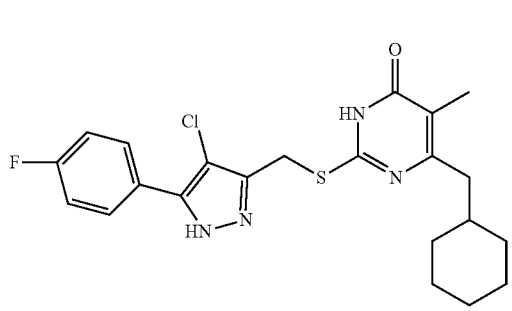

I-68

Compound I-68 was prepared according to method for preparing the target compound I-1 except that 4'-fluoroacetophenone was used as the raw material 1 in the step (1) and 6-cyclohexylmethyl-5-methyl-thiouracil A was used in the S-alkylation reaction of the step (6).

The product was obtained as a white crystal with a yield of 86%. $^1$H NMR (DMSO-d$_6$, 400 MHz) δ 0.92-0.97 (m, 2H, Cyclohexyl-H), 1.06-1.07 (m, 3H, Cyclohexyl-H), 1.51-1.58 (m, 5H, Cyclohexyl-H), 1.70 (s, 1H, Cyclohexyl-H), 1.87 (s, 3H, CH$_3$), 2.37-2.39 (d, 2H, J=6.9 Hz, CH$_2$—Cyclohexyl), 4.43 (s, 2H, CH$_2$—S), 7.32-7.36 (t, 2H, J=8.7 Hz, Ph-H), 7.80-7.84 (m, 2H, Ph-H), 12.87 (br, 2H, NH); $^{13}$C NMR (DMSO-d$_6$, 100 MHz) δ 24.13, 26.16 (3C), 26.36 (2C), 33.04, 37.12, 41.87, 105.50, 116.20 (2C), 129.13 (2C), 139.22, 146.53, 152.02, 156.28, 159.55, 161.24, 162.22, 163.69.

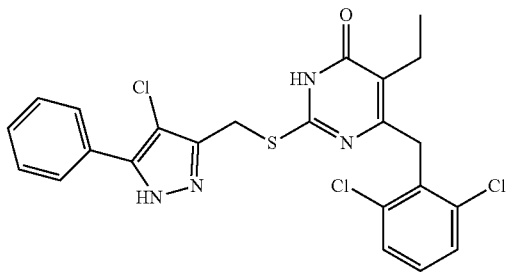

I-70

Compound I-70 was prepared according to method for preparing the target compound I-1 except that 6-(2',6'-dichlorobenzyl)-5-ethyl-thiouracil A was used in the S-alkylation reaction of the step (6).

The product was obtained as a white crystal with a yield of 75%. $^1$H NMR (DMSO-d$_6$, 400 MHz) δ 1.09-1.12 (t, 3H, J=7.3 Hz, CH$_2$—CH$_3$), 2.54-2.59 (m, 2H, CH$_2$—CH$_3$), 3.96 (s, 2H, CH$_2$-Ph), 4.22 (s, 2H, CH$_2$—S), 7.22-7.26 (t, 1H, J=8.0 Hz, Ph-H), 7.40-7.43 (m, 3H, Ph-H), 7.48-7.52 (t, 2H, J=7.5 Hz, Ph-H), 7.74-7.76 (d, 2H, J=7.6 Hz, Ph-H), 12.99 (br, 2H, NH); $^{13}$C NMR (DMSO-d$_6$, 100 MHz) δ 13.06, 18.38, 24.49, 35.17, 105.52, 121.20, 126.98 (2C), 128.37 (2C), 129.09, 129.29 (2C), 129.37, 135.00, 136.08, 139.24, 143.40, 147.65, 153.06, 157.87, 160.77, 163.28.

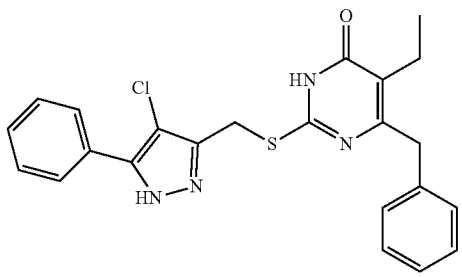

Compound I-71 was prepared according to method for preparing the target compound I-1 except that 6-benzyl-5-ethyl-thiouracil A was used in the S-alkylation reaction of the step (6).

The product was obtained as a white crystal with a yield of 86%. $^1$H NMR (DMSO-$d_6$, 400 MHz) δ 0.90-0.93 (t, 3H, J=7.3 Hz, CH$_2$—C$\underline{H}_3$), 2.42-2.48 (m, 2H, C$\underline{H}_2$—CH$_3$), 3.90 (s, 2H, C$\underline{H}_2$-Ph), 4.43 (s, 2H, C$\underline{H}_2$—S), 7.14-7.18 (t, 1H, J=7.0 Hz, Ph-H), 7.23-7.26 (t, 2H, J=7.3 Hz, Ph-H), 7.28-7.30 (d, 2H, J=7.2 Hz, Ph-H), 7.40-7.44 (t, 1H, J=7.2 Hz, Ph-H), 7.48-7.52 (t, 2H, J=7.4 Hz, Ph-H), 7.77-7.79 (d, 2H, J=7.6 Hz, Ph-H), 12.86-13.43 (br, 2H, NH); $^{13}$C NMR (DMSO-$d_6$, 100 MHz) δ 13.50, 18.68, 24.48, 40.13, 105.67, 121.54, 126.65, 127.01 (2C), 128.74 (2C), 129.03, 129.27 (4C), 138.96, 143.47, 146.32, 152.34, 156.96, 160.95, 163.79.

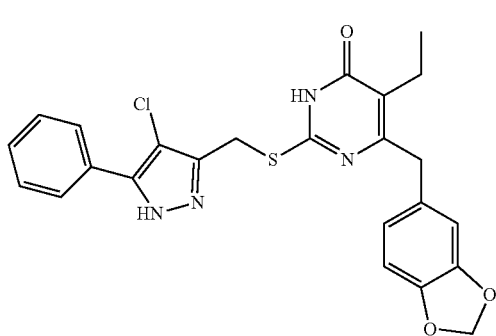

Compound I-72 was prepared according to method for preparing the target compound I-1 except that 6-(1',3'-benzodioxy)-5-ethyl-thiouracil A was used in the S-alkylation reaction of the step (6).

The product was obtained as a white crystal with a yield of 85%. $^1$H NMR (DMSO-$d_6$, 400 MHz) δ 0.91-0.94 (t, 3H, J=7.2 Hz, CH$_2$—C$\underline{H}_3$), 2.41-2.47 (m, 2H, C$\underline{H}_2$—CH$_3$), 3.81 (s, 2H, C$\underline{H}_2$-Ph), 4.44 (s, 2H, C$\underline{H}_2$—S), 5.92 (s, 2H, O—C$\underline{H}_2$—O), 6.74-6.79 (m, 2H, Ph-H), 6.85 (s, 1H, Ph-H), 7.40-7.44 (t, 1H, J=7.2 Hz, Ph-H), 7.48-7.52 (t, 2H, J=7.4 Hz, Ph-H), 7.77-7.79 (d, 2H, J=7.5 Hz, Ph-H), 12.83-13.43 (br, 2H, NH); $^{13}$C NMR (DMSO-$d_6$, 100 MHz) δ 13.55, 18.61, 24.49, 39.69, 101.16, 105.18, 108.50, 109.65, 122.18, 127.02 (2C), 129.02, 129.24 (2C), 131.14, 132.62, 144.38, 146.07, 147.60, 151.33, 157.02, 160.58, 161.19, 163.59.

Effect Example 1: Anti-HIV-1 Activity Test

C8166 cells infected with HIV-1 were used for determining the anti-HIV biological activity at the cellular level. The specific method was described below.

Cytotoxicity experiment: The toxicity of the compounds on C8166 cells was determined by MTT method. In 96-well cell culture plates, the compounds were subjected to 5-fold serial dilution and 100 μL of C8166 cell suspension ($4\times10^5$/mL) was added into each well. Triplicate wells were set for each concentration. At the same time, a cell control group without drugs and drug control groups with Zidovudine (AZT) or Nevirapine (NVP) were set. The cells were incubated at 37° C. in a 5% $CO_2$ incubator for three days, followed by the addition of MTT solution into each well, and then the cells were incubated at 37° C. for 4 hours. 10% SDS-50% DMF was added into each well and the cells were incubated at 37° C. in a 5% $CO_2$ incubator overnight. After mixing evenly, the OD values were measured by BIO-TEK ELx800 ELISA instrument (determination wavelength: 570 nm; reference wavelength: 630 nm). The dose-response curve was graphed according to the experimental results, and the $CC_{50}$ was calculated (the concentrations of the compounds required to produce toxicity on 50% cells).

Syncytium inhibition experiment: 100 μL of C8166 cell suspension ($4\times10^5$/mL) was seeded into each well of 96-well cell culture plates containing 5-fold serial dilutions of the compounds, followed by addition of HIV-$1_{IIIB}$ diluted supernatant (MOI=0.04). Triplicate wells were set for each serial concentration. At the same time, negative control wells of HIV-$1_{IIIB}$ infection without compounds and positive control wells with Zidovudine (AZT) or Nevirapine (NVP) were set. The cells were cultured at 37° C. in a 5% $CO_2$ incubator for three days. The number of the syncytia was counted in five non-overlapping fields of view by using an inverted microscope (100×). The dose-response curves were graphed according to the experimental results, and the 50% effective concentrations of the compounds for inhibiting the virus (EC50, 50% effective concentration) were calculated according to Reed & Muench method. Calculation formula: cytopathic inhibition rate (%)=(1−number of syncytia in experimental wells/number of syncytia in control well)×100%.

In the present disclosure, AZT and NVP were used as control, and the inhibitory activity data of some target compounds on HIV-$1_{IIIB}$ is shown in Table 1:

TABLE 1

Inhibitory activity data of target compounds on HIV-$1_{IIIB}$

| No. | $CC_{50}$ (μM) | $EC_{50}$ (μM) | SI |
|---|---|---|---|
| I-01 | >200 | 0.099 | >2020.2 |
| I-02 | 84.48 | 0.007 | 12069 |
| I-03 | 76.26 | 0.051 | 1495.3 |
| I-04 | 58.06 | 0.101 | 574.85 |
| I-05 | 80.99 | 0.066 | 1227.1 |
| I-06 | 66.08 | 0.057 | 1159.3 |
| I-07 | 83.86 | 0.018 | 4658.9 |
| I-08 | 74.93 | 0.020 | 3746.5 |
| I-09 | 64.92 | 0.018 | 3606.7 |
| I-10 | >200 | 0.023 | >8695.7 |
| I-11 | 49.84 | 0.130 | 383.38 |
| I-12 | 75.35 | 0.310 | 243.06 |
| I-13 | >200 | 0.349 | >573.07 |
| I-14 | 71.99 | 0.035 | 2056.9 |
| I-15 | >200 | 0.071 | >2816.9 |
| I-16 | >200 | 0.089 | >2247.2 |
| I-17 | 96.78 | 0.004 | 24195.0 |
| I-18 | 86.43 | 0.162 | 533.52 |
| I-19 | 115.43 | 0.151 | 764.44 |
| I-20 | 59.71 | 0.042 | 1421.7 |
| I-21 | 82.76 | 0.074 | 1118.4 |
| I-22 | >200 | 0.138 | >1449.3 |
| I-23 | 91.42 | 0.052 | 1758.1 |

TABLE 1-continued

Inhibitory activity data of target compounds on HIV-1$_{IIIB}$

| No. | CC$_{50}$ (μM) | EC$_{50}$ (μM) | SI |
|---|---|---|---|
| I-24 | 77.10 | 0.086 | 896.51 |
| I-25 | >200 | 0.012 | >16666 |
| I-26 | 34.42 | 0.302 | 113.97 |
| I-27 | 55.05 | 0.182 | 302.47 |
| I-28 | 31.12 | 0.147 | 211.70 |
| I-29 | 87.39 | 0.476 | 183.59 |
| I-30 | 67.93 | 0.296 | 229.49 |
| I-31 | 75.01 | 0.033 | 2273.0 |
| I-32 | 45.16 | 0.028 | 1612.9 |
| I-33 | 47.19 | 0.025 | 1887.6 |
| I-34 | 79.44 | 0.023 | 3453.9 |
| I-35 | 103.51 | 0.002 | 51755 |
| I-36 | 91.25 | 0.009 | 10139 |
| I-37 | 72.96 | 0.006 | 12160 |
| I-38 | 156.36 | 0.003 | 52120 |
| I-39 | 98.98 | 0.016 | 6186.3 |
| I-40 | >200 | 0.012 | >16666 |
| I-41 | 54.615 | 0.1864 | 339.5 |
| I-42 | 42.23 | 0.3551 | 134.7 |
| I-43 | 66.88 | 0.1941 | 345.3 |
| I-44 | 79.55 | 5.342 | 18.52 |
| I-45 | 61.62 | 10.07 | 6.75 |
| I-46 | 56.05 | 3.956 | 14.16 |
| I-47 | 61.77 | 0.142 | 436.23 |
| I-48 | 98.88 | 0.927 | 106.68 |
| I-49 | >200 | 0.837 | >238.81 |
| I-50 | 78.05 | 2.967 | 26.306 |
| I-51 | 45.54 | 0.602 | 75.660 |
| I-52 | >200 | 0.097 | >2070.4 |
| I-53 | >200 | 0.141 | >1415.4 |
| I-54 | 88.96 | 3.882 | 22.915 |
| I-55 | >200 | 0.700 | >285.67 |
| I-56 | 40.29 | 0.587 | 68.617 |
| I-57 | 81.09 | 0.080 | 1008.5 |
| I-58 | 80.95 | 0.400 | 202.16 |
| I-59 | 89.10 | 23.91 | 3.7259 |
| I-60 | 64.88 | 0.733 | 88.567 |
| I-61 | 46.35 | 0.124 | 373.79 |
| I-62 | >200 | 4.980 | >40.163 |
| I-63 | >200 | 0.063 | >3169.6 |
| I-64 | >200 | 0.643 | >310.87 |
| I-65 | >200 | 0.370 | >540.98 |
| I-66 | >200 | 0.071 | >2809.0 |
| I-67 | >200 | 0.847 | >236.04 |
| I-68 | >200 | 0.111 | >1802.6 |
| I-69 | >200 | 0.055 | >3656.3 |
| I-70 | >200 | 0.092 | >2173.9 |
| I-71 | >200 | 0.051 | >3940.9 |
| I-72 | >200 | 0.081 | >2470.7 |
| AZT | >749 | 0.049 | >15286 |
| NVP | >200 | 0.0584 | >3424 |

The compounds of the present disclosure are a novel structural type of pyrimidinone-containing compounds. It can be seen from Table 1 that the compounds have significant anti-HIV activities, the EC$_{50}$ values of some of the preferred compounds reach nanomolar levels, and the CC$_{50}$ values of compounds I-01, 10, 13, 15, 16, 22, 25, 40, 49, 52, 53, 55, 62-72 on C8166 cells are greater than 200 μM in vitro. Therefore, the compounds of the present disclosure are novel HIV-RT inhibitors with novel structures and have characteristics of high efficacy and low toxicity.

Although the specific embodiments of the present disclosure have been described above, those skilled in the art should understand that these embodiments are only intended for illustration, and various changes or variations can be made to these embodiments without departing from the spirit and essence of the present disclosure. Therefore, the scope of protection of the present disclosure is defined by the appended claims.

What is claimed is:

1. A compound selected from the group consisting of a compound represented by formula I, or a N-oxide, tautomer, optical isomer, hydrate, solvate, or pharmaceutically acceptable salt thereof:

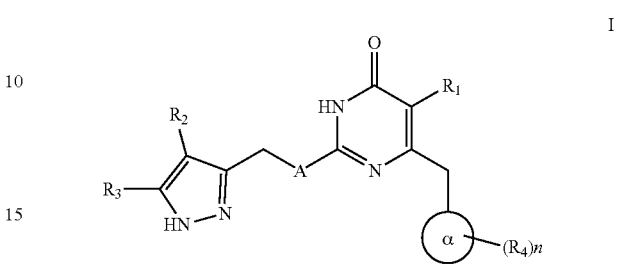

wherein:
A is S, O, NH or NCH$_3$;
R$_1$ is H, C$_1$-C$_6$ branched or straight chain alkyl, or C$_3$-C$_6$ cycloalkyl;
R$_2$ is H or halogen;
R$_3$ is H, C$_1$-C$_{12}$ branched or straight chain alkyl, C$_3$-C$_6$ cycloalkyl, C$_6$-C$_{20}$ aryl, C$_2$-C$_{10}$ heteroaryl, C$_6$-C$_{20}$ aryl substituted by one or more R$_{3a}$, or C$_2$-C$_{10}$ heteroaryl substituted by one or more R$_{3b}$; wherein each of R$_{3a}$ and R$_{3b}$ is independently selected from hydroxyl, nitro, halogen, amino, cyano, HOS(=O)$_2$—, CH$_3$S(=O)$_2$—, C$_1$-C$_6$ branched or straight chain alkyl-S(=O)$_2$NH—, C$_1$-C$_6$ branched or straight chain alkyl, C$_1$-C$_6$ branched or straight chain alkoxy, C$_1$-C$_6$ branched or straight chain alkylthio, C$_1$-C$_6$ branched or straight chain haloalkyl, when R$_{3a}$ or R$_{3b}$ is present more than once, then each R$_{3a}$ or each R$_{3b}$ is the same or different;
α ring is cyclohexyl or phenyl, wherein the phenyl is substituted by n R$_4$ where each R$_4$ is the same or different, n is 0, 1, 2, 3 or 4; R$_4$ is halogen, hydroxyl, cyano, nitro, amino, C$_1$-C$_6$ branched or straight chain alkyl, or C$_1$-C$_6$ branched or straight chain alkoxy.

2. The compound as defined in claim 1, wherein,
R$_1$ is C$_1$-C$_3$ branched or straight chain alkyl, cyclopropyl, cyclobutyl, cyclopentyl or cyclohexyl;
or R$_2$ is fluorine, chlorine, bromine or iodine;
or R$_3$ is C$_1$-C$_6$ branched or straight chain alkyl, cyclopropyl, cyclobutyl, cyclopentyl, cyclohexyl, C$_6$-C$_{10}$ aryl, C$_2$-C$_6$ heteroaryl, or phenyl substituted by one or more R$_{3a}$, then the substituted is mono-substituted or di-substituted;
or R$_{3a}$ or R$_{3b}$ is fluorine, chlorine, bromine, iodine, C$_1$-C$_3$ branched or straight chain alkyl-S(=O)$_2$NH—, C$_1$-C$_3$ branched or straight chain alkyl, C$_1$-C$_3$ branched or straight chain alkoxy, C$_1$-C$_3$ branched or straight chain alkylthio, or C$_1$-C$_3$ straight or branched chain haloalkyl;
or R$_4$ is fluorine, chlorine, bromine, iodine, C$_1$-C$_3$ branched or straight chain alkyl, or C$_1$-C$_3$ branched or straight chain alkoxy;
or n is 2, all R$_4$ are halogen or all R$_4$ are C$_1$-C$_6$ branched or straight chain alkyl;
or, the two R$_4$ are independently C$_1$-C$_6$ branched or straight chain alkoxy.

3. The compound as defined in claim 1, wherein,
R$_1$ is isopropyl, n-propyl, ethyl or methyl;
or R$_2$ is chlorine;
or R$_3$ is C$_1$-C$_4$ branched or straight chain alkyl or phenyl substituted by one or more R$_{3a}$ or C$_2$-C$_{10}$ heteroaryl substituted by one or more R$_{3b}$, then the C$_2$-C$_{10}$ heteroaryl is pyridyl, pyridazinyl, pyrimidinyl, pyrazinyl, furanyl, thienyl, pyrrolyl, pyrazolyl, imidazolyl, oxazolyl, isoxazolyl, thiazolyl, pyrimidinonyl, oxadiazolyl, pyridonyl or triazolyl;

or R$_{3a}$ or R$_{3b}$ is methyl-S(=O)$_2$NH—, ethyl-S(=O)$_2$NH—, n-propyl-S(=O)$_2$NH—, isopropyl-S(=O)$_2$NH—, methyl, ethyl, n-propyl, isopropyl, methoxy, ethoxy, propoxy, isopropoxy, methylthio, ethylthio, propylthio, isopropylthio, trifluoromethyl, difluoromethyl or 1,2-difluoroethyl;

or R$_4$ is methyl, ethyl, n-propyl, isopropyl, methoxy, ethoxy, propoxy or isopropoxy, or n is 2, all R$_4$ are fluorine, or all R$_4$ are chlorine, or all R$_4$ are methyl; or, the two R$_4$ are linked together to form a ring, where the ring is an oxygen-containing heterocycle fused to the phenyl.

4. The compound as defined in claim 1, wherein,

R$_3$ is methyl, ethyl, propyl, isopropyl, n-butyl, isobutyl, sec-butyl, tert-butyl,

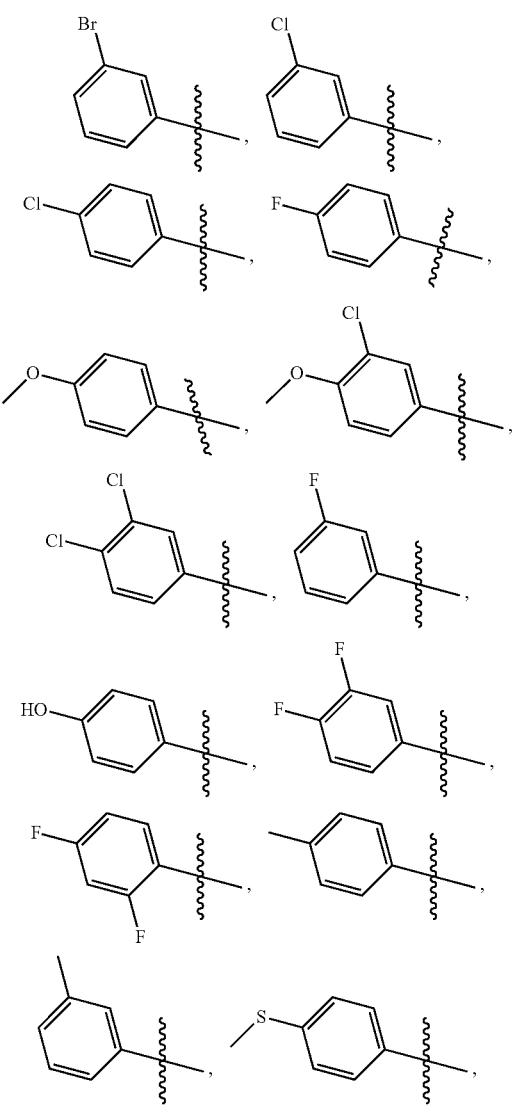

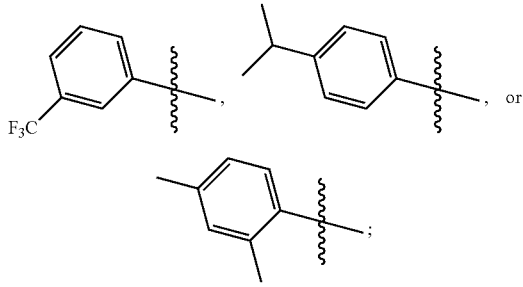

or n is 2, then R$_4$ is located in the 2-position and 6-position of the phenyl, or 3-position and 5-position of the phenyl;

or, n is 2, the two R$_4$ form an oxygen-containing 5-7 membered heterocycle fused to the phenyl.

5. The compound as defined in claim 1, wherein,

A is S;

or, α ring is

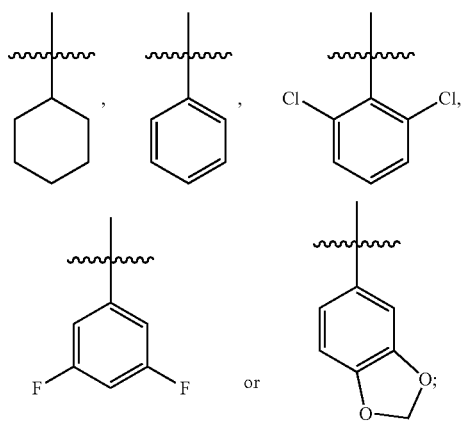

or, R$_1$ is H, methyl, ethyl or isopropyl;

or, R$_2$ is H or Cl;

or, R$_3$ is C$_6$-C$_{20}$ aryl, C$_2$-C$_{10}$ heteroaryl, C$_6$-C$_{20}$ aryl substituted by one or more R$_{3a}$, or C$_2$-C$_{10}$ heteroaryl substituted by one or more R$_{3b}$.

6. The compound as defined in claim 1, wherein, when R$_3$ is C$_6$-C$_{20}$ aryl substituted by one or more R$_{3a}$, or C$_2$-C$_{10}$ heteroaryl substituted by one or more R$_{3b}$, then the one or more is 1-6.

7. The compound as defined in claim 1, wherein,

A is S, α ring is

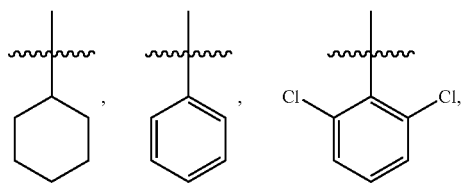

-continued

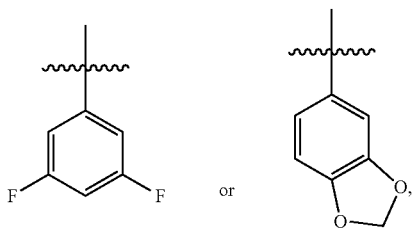

$R_1$ is ethyl or isopropyl; $R_2$ is H or Cl; $R_3$ is $C_6$-$C_{20}$ aryl, $C_2$-$C_{10}$ heteroaryl, $C_6$-$C_{20}$ aryl substituted by one or more $R_{3a}$, or $C_2$-$C_{10}$ heteroaryl substituted by one or more $R_{3b}$.

8. The compound as defined in claim 1, wherein, the moiety

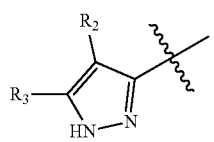

contained in the compound represented by formula I is

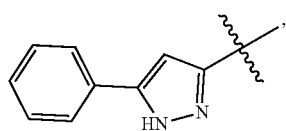

-continued

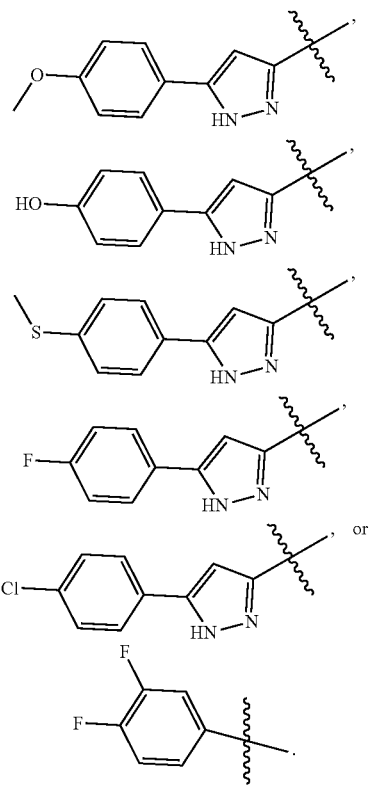

9. The compound represented by formula I as defined in claim 1, wherein, the compound is elected from the group consisting of:

| Compound | Structure |
|---|---|
| I-1 | 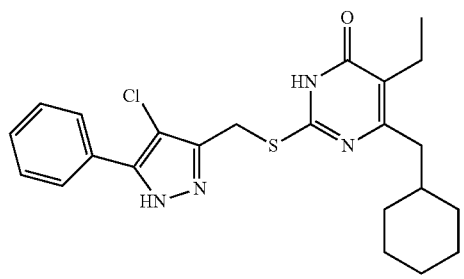 [SMILES: CCc1c(CC2CCCCC2)nc(SCc2n[nH]c(-c3ccccc3)c2Cl)[nH]c1=O] |
| I-2 | 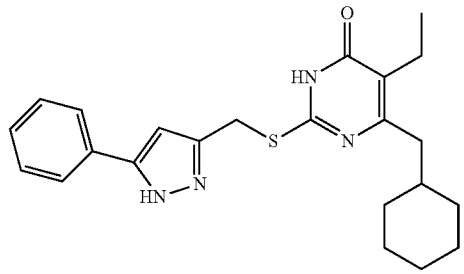 [SMILES: CCc1c(CC2CCCCC2)nc(SCc2cc(-c3ccccc3)[nH]n2)[nH]c1=O] |

| Compound | Structure |
|---|---|
| I-3 | 3-bromophenyl-pyrazole-CH2-S-[5-ethyl-6-(cyclohexylmethyl)pyrimidin-4(3H)-one] |
| I-4 | 3-bromophenyl-(4-chloro)pyrazole-CH2-S-[5-ethyl-6-(cyclohexylmethyl)pyrimidin-4(3H)-one] |
| I-5 | 3-chlorophenyl-pyrazole-CH2-S-[5-ethyl-6-(cyclohexylmethyl)pyrimidin-4(3H)-one] |
| I-6 | 3-chlorophenyl-(4-chloro)pyrazole-CH2-S-[5-ethyl-6-(cyclohexylmethyl)pyrimidin-4(3H)-one] |
| I-7 | 4-chlorophenyl-pyrazole-CH2-S-[5-ethyl-6-(cyclohexylmethyl)pyrimidin-4(3H)-one] |

-continued
| Compound | Structure |
|---|---|
| I-8 | 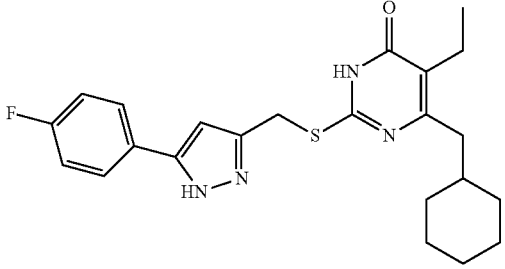 [SMILES: CCc1c(CC2CCCCC2)nc(SCc2cc(-c3ccc(F)cc3)[nH]n2)[nH]c1=O] |
| I-9 | 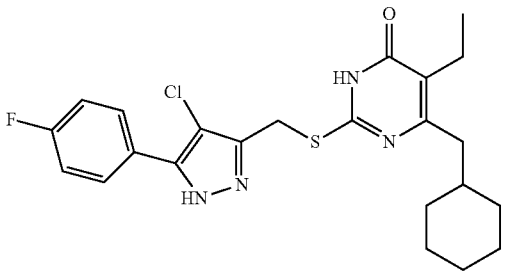 [SMILES: CCc1c(CC2CCCCC2)nc(SCc2n[nH]c(-c3ccc(F)cc3)c2Cl)[nH]c1=O] |
| I-10 | 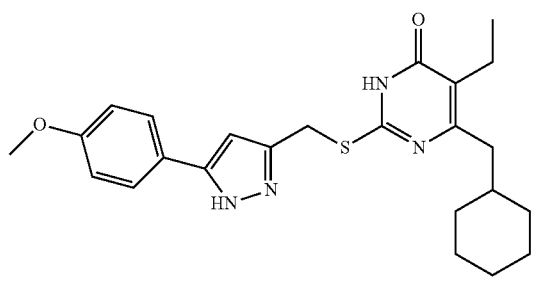 |
| I-11 | 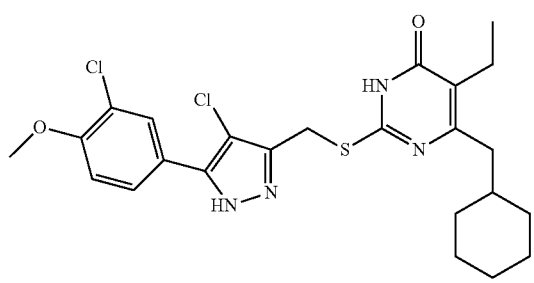 [SMILES: CCc1c(CC2CCCCC2)nc(SCc2n[nH]c(-c3ccc(OC)c(Cl)c3)c2Cl)[nH]c1=O] |
| I-12 | 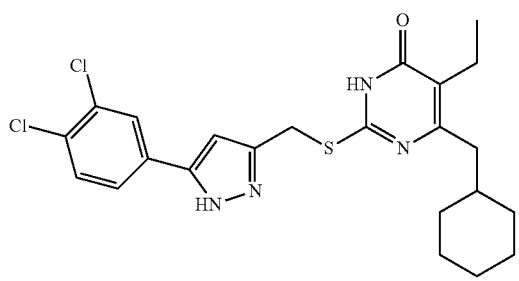 [SMILES: CCc1c(CC2CCCCC2)nc(SCc2cc(-c3ccc(Cl)c(Cl)c3)[nH]n2)[nH]c1=O] |

-continued

| Compound | Structure |
|---|---|
| I-13 | 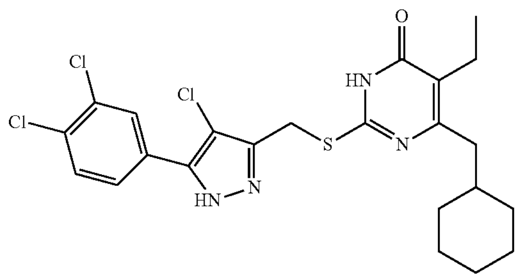 [SMILES: CCc1c(CC2CCCCC2)nc(SCc2n[nH]c(-c3ccc(Cl)c(Cl)c3)c2Cl)[nH]c1=O] |
| I-14 | 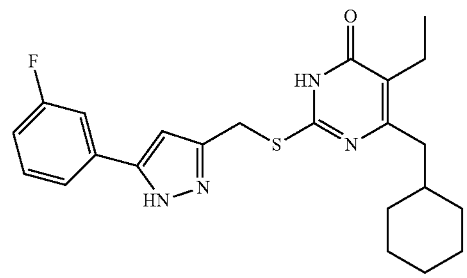 |
| I-15 | 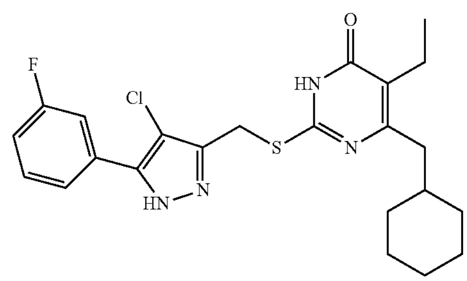 [SMILES: CCc1c(CC2CCCCC2)nc(SCc2n[nH]c(-c3cccc(F)c3)c2Cl)[nH]c1=O] |
| I-16 | 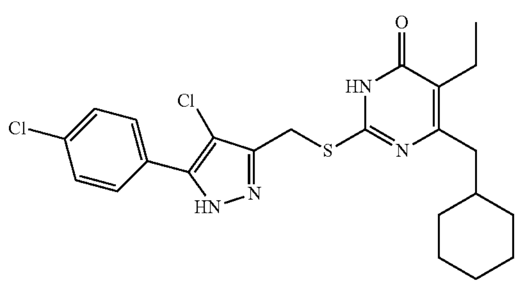 [SMILES: CCc1c(CC2CCCCC2)nc(SCc2n[nH]c(-c3ccc(Cl)cc3)c2Cl)[nH]c1=O] |
| I-17 | 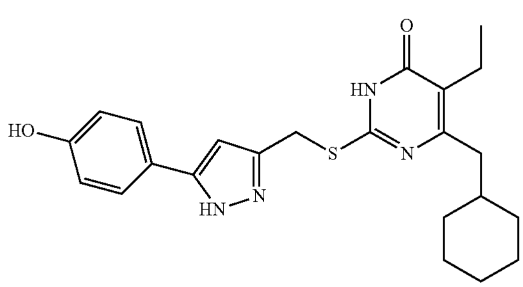 [SMILES: CCc1c(CC2CCCCC2)nc(SCc2cc(-c3ccc(O)cc3)[nH]n2)[nH]c1=O] |

| Compound | Structure |
|---|---|
| I-18 | 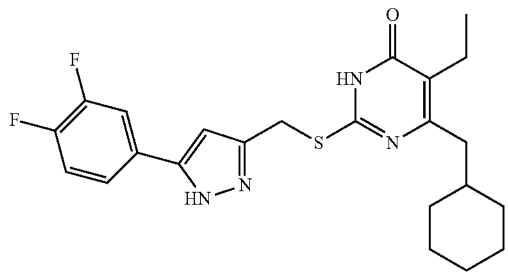 [SMILES: CCc1c(CC2CCCCC2)nc(SCc2cc(-c3ccc(F)c(F)c3)[nH]n2)[nH]c1=O] |
| I-19 | 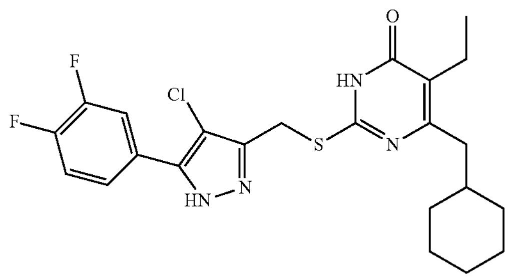 [SMILES: CCc1c(CC2CCCCC2)nc(SCc2n[nH]c(-c3ccc(F)c(F)c3)c2Cl)[nH]c1=O] |
| I-20 | 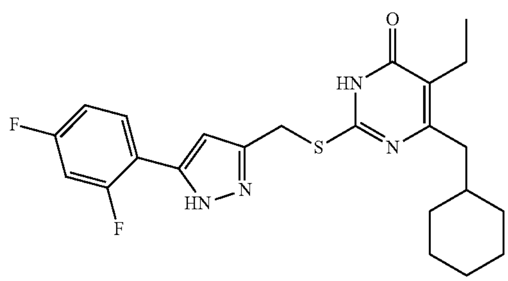 [SMILES: CCc1c(CC2CCCCC2)nc(SCc2cc(-c3ccc(F)cc3F)[nH]n2)[nH]c1=O] |
| I-21 | 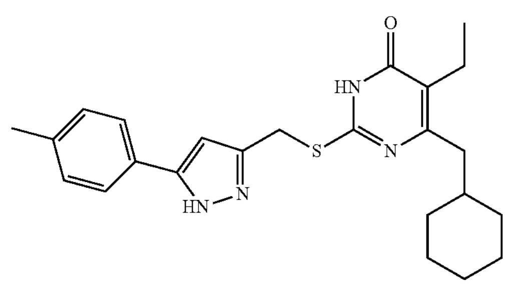 [SMILES: CCc1c(CC2CCCCC2)nc(SCc2cc(-c3ccc(C)cc3)[nH]n2)[nH]c1=O] |
| I-22 | 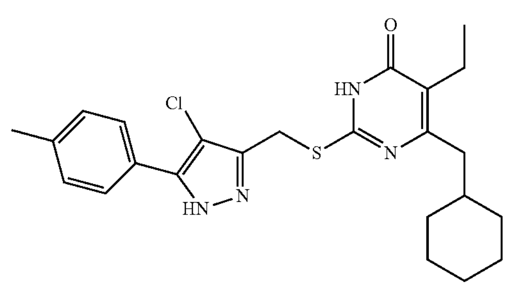 [SMILES: CCc1c(CC2CCCCC2)nc(SCc2n[nH]c(-c3ccc(C)cc3)c2Cl)[nH]c1=O] |

-continued

| Compound | Structure |
|---|---|
| I-23 | 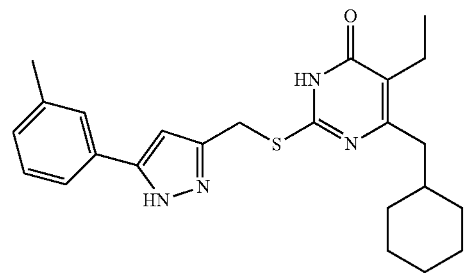 [SMILES: CCc1c(CC2CCCCC2)nc(SCc2cc(-c3cccc(C)c3)[nH]n2)[nH]c1=O] |
| I-24 | 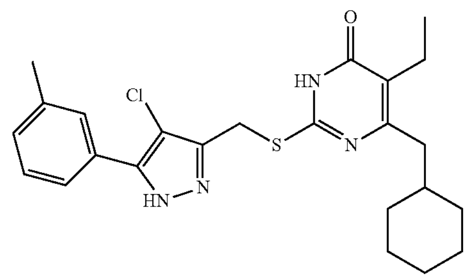 |
| I-25 | 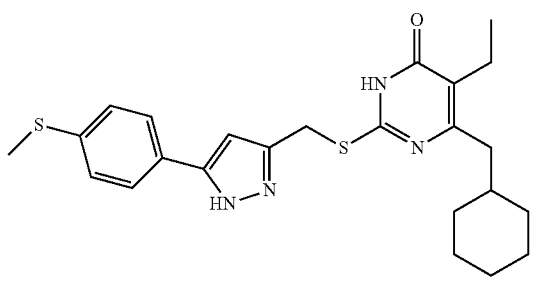 |
| I-26 | 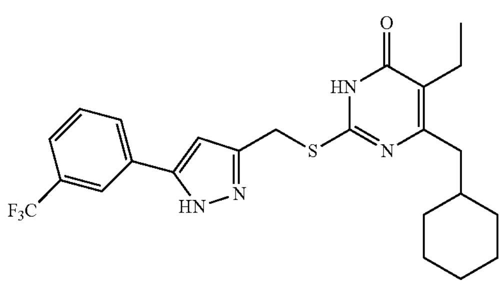 [SMILES: CCc1c(CC2CCCCC2)nc(SCc2cc(-c3cccc(C(F)(F)F)c3)[nH]n2)[nH]c1=O] |
| I-27 | 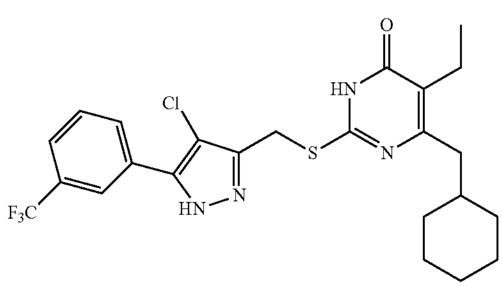 [SMILES: CCc1c(CC2CCCCC2)nc(SCc2n[nH]c(-c3cccc(C(F)(F)F)c3)c2Cl)[nH]c1=O] |

-continued

| Compound | Structure |
|---|---|
| I-28 | 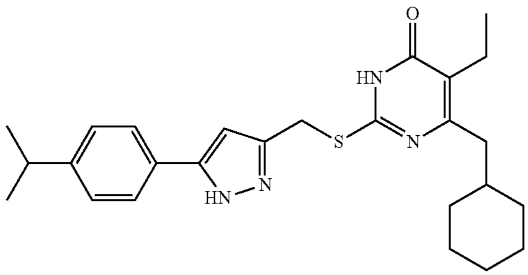 [SMILES: CCc1c(CC2CCCCC2)nc(SCc2cc(-c3ccc(C(C)C)cc3)[nH]n2)[nH]c1=O] |
| I-29 | 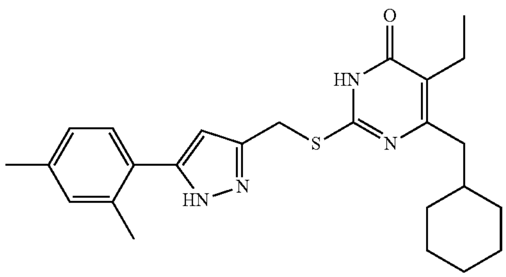 [SMILES: CCc1c(CC2CCCCC2)nc(SCc2cc(-c3ccc(C)cc3C)[nH]n2)[nH]c1=O] |
| I-30 | 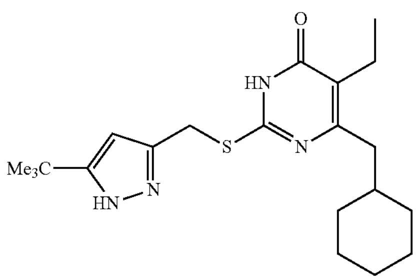 |
| I-31 | 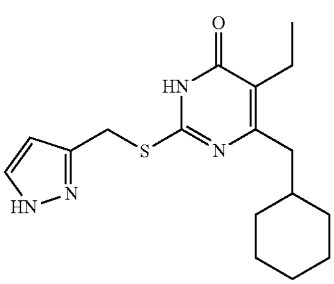 [SMILES: CCc1c(CC2CCCCC2)nc(SCc2cc[nH]n2)[nH]c1=O] |
| I-32 | 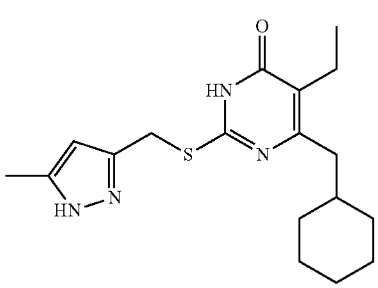 [SMILES: CCc1c(CC2CCCCC2)nc(SCc2cc(C)[nH]n2)[nH]c1=O] |

-continued

| Compound | Structure |
|---|---|
| I-33 | 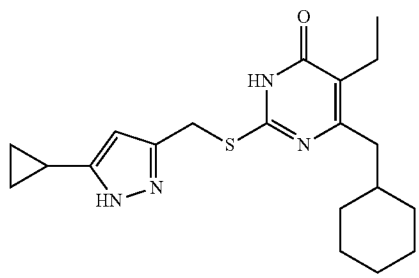 [SMILES: CCc1c(CC2CCCCC2)nc(SCc2cc(C3CC3)[nH]n2)[nH]c1=O] |
| I-34 | 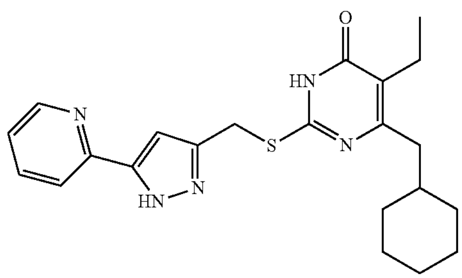 [SMILES: CCc1c(CC2CCCCC2)nc(SCc2cc(-c3ccccn3)[nH]n2)[nH]c1=O] |
| I-35 | 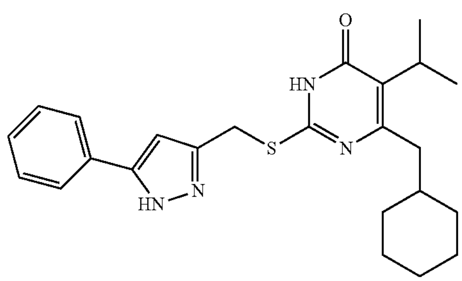 [SMILES: CC(C)c1c(CC2CCCCC2)nc(SCc2cc(-c3ccccc3)[nH]n2)[nH]c1=O] |
| I-36 | 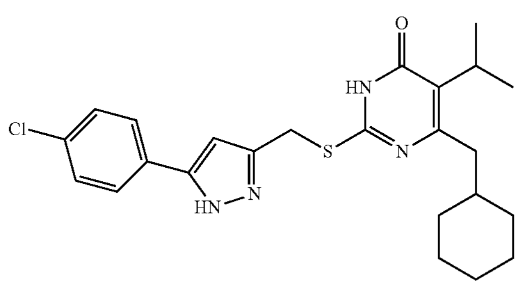 [SMILES: CC(C)c1c(CC2CCCCC2)nc(SCc2cc(-c3ccc(Cl)cc3)[nH]n2)[nH]c1=O] |
| I-37 | 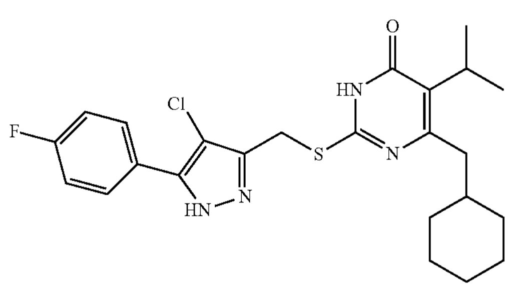 [SMILES: CC(C)c1c(CC2CCCCC2)nc(SCc2n[nH]c(-c3ccc(F)cc3)c2Cl)[nH]c1=O] |

-continued

| Compound | Structure |
|---|---|
| I-38 | 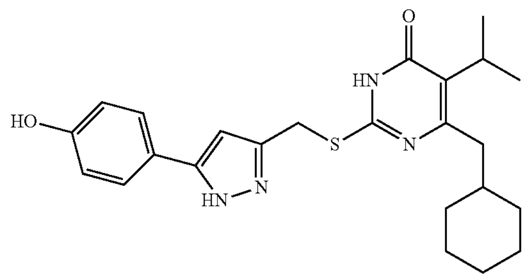 [SMILES: CC(C)c1c(CC2CCCCC2)nc(SCc2cc(-c3ccc(O)cc3)[nH]n2)[nH]c1=O] |
| I-39 | 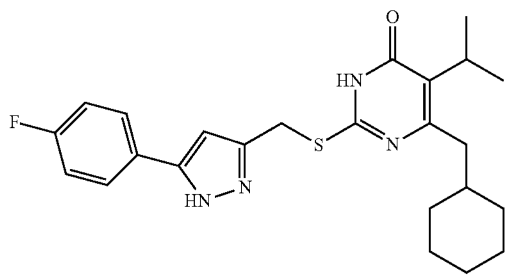 [SMILES: CC(C)c1c(CC2CCCCC2)nc(SCc2cc(-c3ccc(F)cc3)[nH]n2)[nH]c1=O] |
| I-40 | 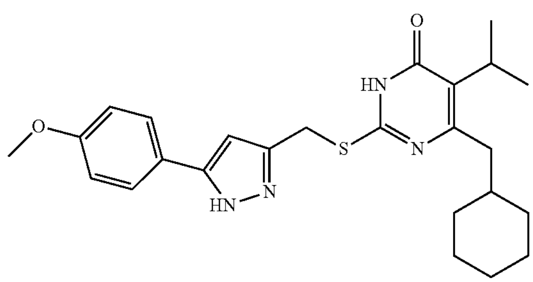 [SMILES: COc1ccc(-c2cc(CSc3nc(CC4CCCCC4)c(C(C)C)c(=O)[nH]3)n[nH]2)cc1] |
| I-41 | 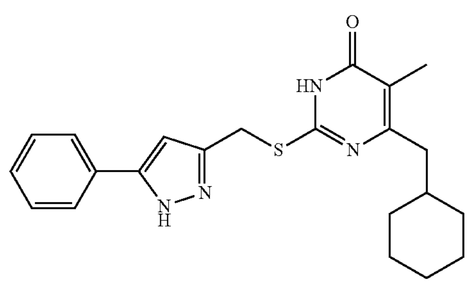 [SMILES: Cc1c(CC2CCCCC2)nc(SCc2cc(-c3ccccc3)[nH]n2)[nH]c1=O] |
| I-42 | 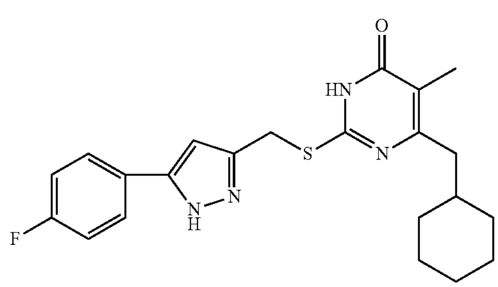 [SMILES: Cc1c(CC2CCCCC2)nc(SCc2cc(-c3ccc(F)cc3)[nH]n2)[nH]c1=O] |

-continued

| Compound | Structure |
|---|---|
| I-43 | 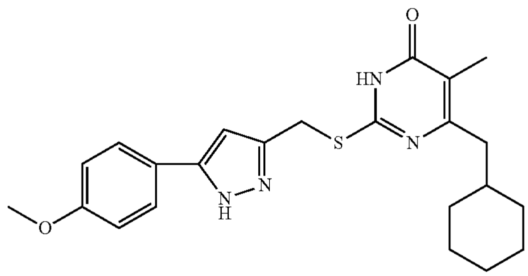 [SMILES: COc1ccc(-c2cc(CSc3nc(CC4CCCCC4)c(C)c(=O)[nH]3)n[nH]2)cc1] |
| I-44 | 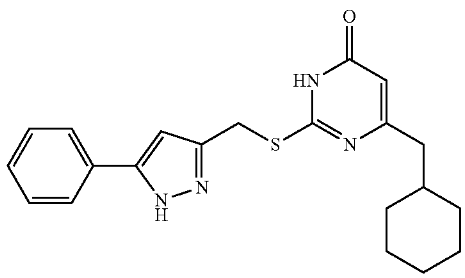 [SMILES: O=c1cc(CC2CCCCC2)nc(SCc2cc(-c3ccccc3)[nH]n2)[nH]1] |
| I-45 | 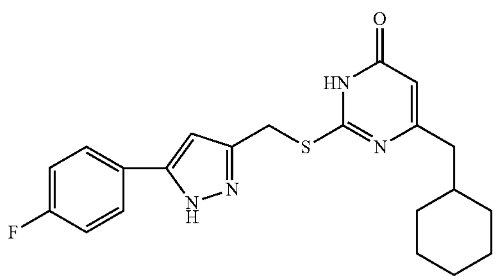 [SMILES: O=c1cc(CC2CCCCC2)nc(SCc2cc(-c3ccc(F)cc3)[nH]n2)[nH]1] |
| I-46 | 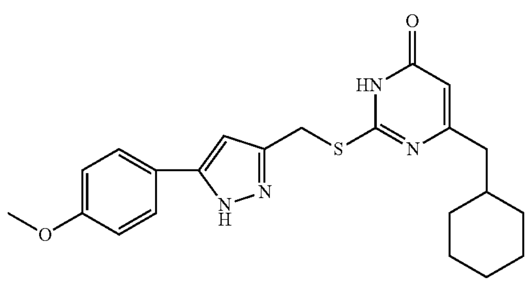 [SMILES: COc1ccc(-c2cc(CSc3nc(CC4CCCCC4)cc(=O)[nH]3)n[nH]2)cc1] |
| I-47 | 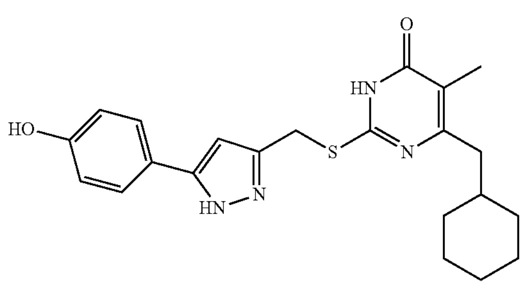 [SMILES: Cc1c(CC2CCCCC2)nc(SCc2cc(-c3ccc(O)cc3)[nH]n2)[nH]c1=O] |

-continued

| Compound | Structure |
|---|---|
| I-48 | 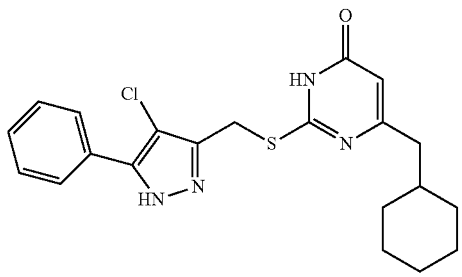 [SMILES: O=c1cc(CC2CCCCC2)nc(SCc2n[nH]c(-c3ccccc3)c2Cl)[nH]1] |
| I-49 | 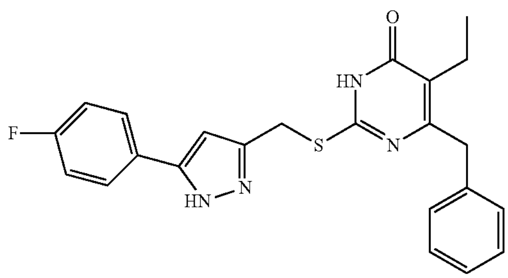 [SMILES: CCc1c(Cc2ccccc2)nc(SCc2cc(-c3ccc(F)cc3)[nH]n2)[nH]c1=O] |
| I-50 | 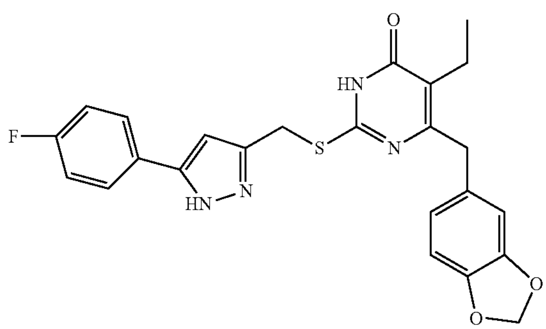 [SMILES: CCc1c(Cc2ccc3c(c2)OCO3)nc(SCc2cc(-c3ccc(F)cc3)[nH]n2)[nH]c1=O] |
| I-51 | 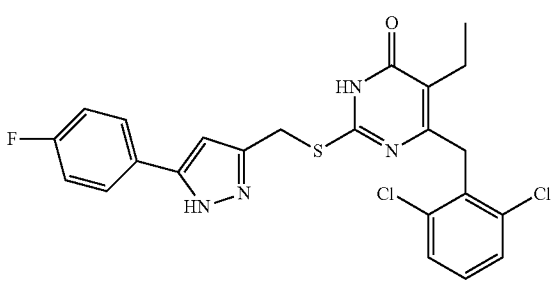 [SMILES: CCc1c(Cc2c(Cl)cccc2Cl)nc(SCc2cc(-c3ccc(F)cc3)[nH]n2)[nH]c1=O] |
| I-52 | 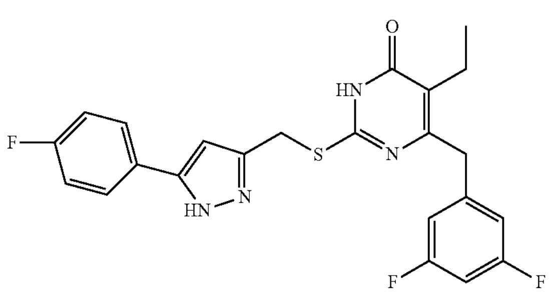 [SMILES: CCc1c(Cc2cc(F)cc(F)c2)nc(SCc2cc(-c3ccc(F)cc3)[nH]n2)[nH]c1=O] |

-continued
| Compound | Structure |
|---|---|
| I-53 | 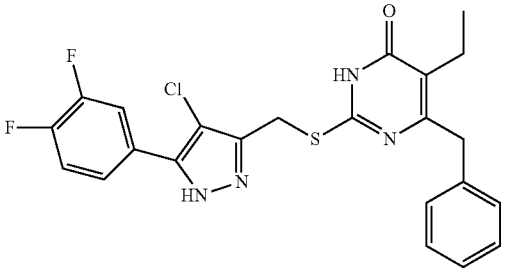 [SMILES: CCc1c(Cc2ccccc2)nc(SCc2n[nH]c(-c3ccc(F)c(F)c3)c2Cl)[nH]c1=O] |
| I-54 | 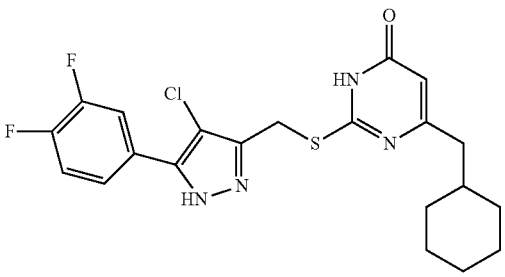 |
| I-55 | 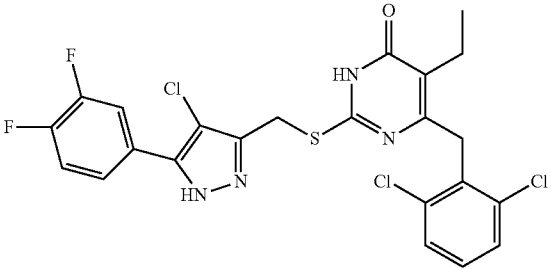 [SMILES: CCc1c(Cc2c(Cl)cccc2Cl)nc(SCc2n[nH]c(-c3ccc(F)c(F)c3)c2Cl)[nH]c1=O] |
| I-56 | 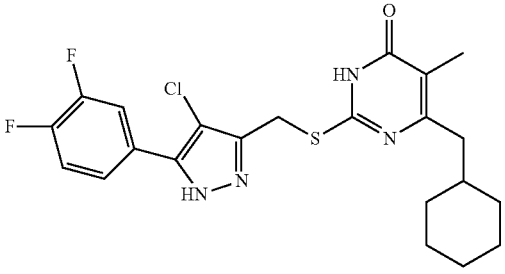 [SMILES: Cc1c(CC2CCCCC2)nc(SCc2n[nH]c(-c3ccc(F)c(F)c3)c2Cl)[nH]c1=O] |
| I-57 | 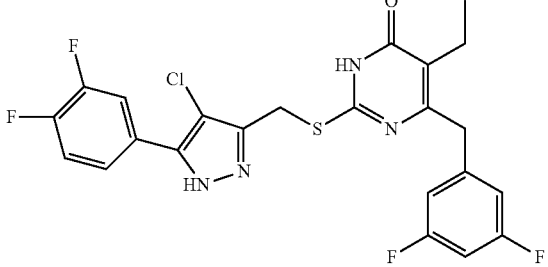 |

| Compound | Structure |
|---|---|
| I-58 | 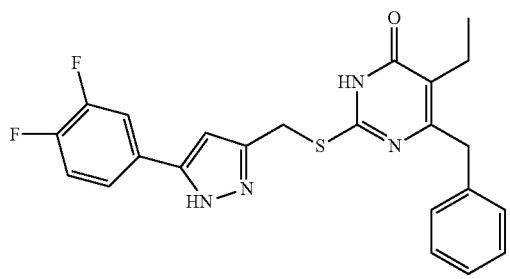 [SMILES: CCc1c(Cc2ccccc2)nc(SCc2cc(-c3ccc(F)c(F)c3)[nH]n2)[nH]c1=O] |
| I-59 | 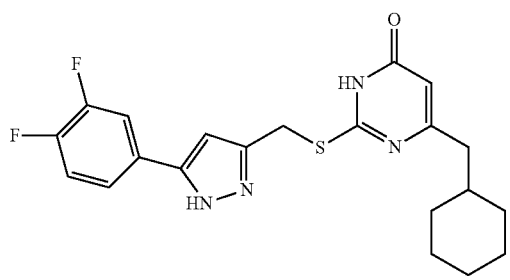 [SMILES: O=c1cc(CC2CCCCC2)nc(SCc2cc(-c3ccc(F)c(F)c3)[nH]n2)[nH]1] |
| I-60 | 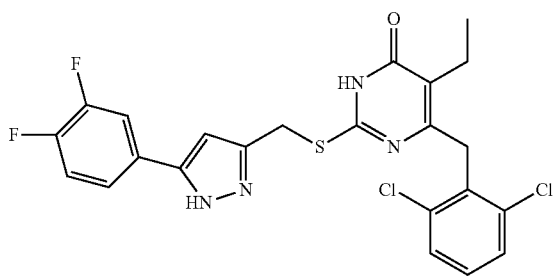 [SMILES: CCc1c(Cc2c(Cl)cccc2Cl)nc(SCc2cc(-c3ccc(F)c(F)c3)[nH]n2)[nH]c1=O] |
| I-61 | 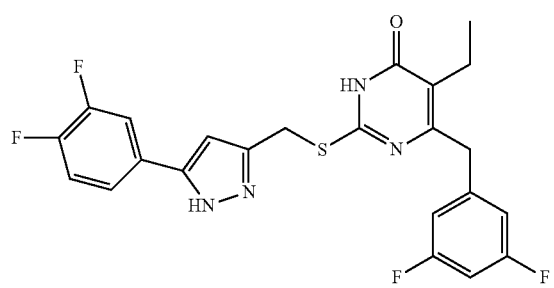 |
| I-62 | 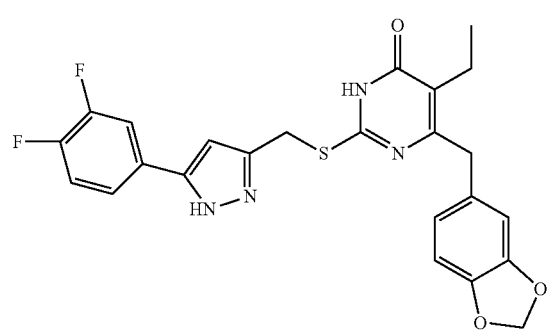 [SMILES: CCc1c(Cc2ccc3c(c2)OCO3)nc(SCc2cc(-c3ccc(F)c(F)c3)[nH]n2)[nH]c1=O] |

-continued
| Compound | Structure |
|---|---|
| I-63 | 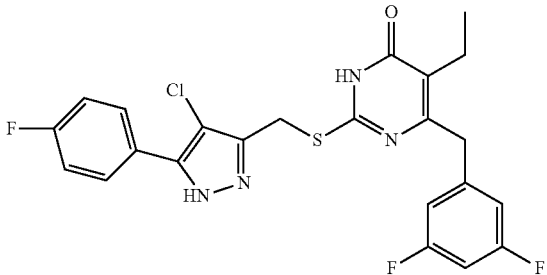 [SMILES: CCc1c(Cc2cc(F)cc(F)c2)nc(SCc2n[nH]c(-c3ccc(F)cc3)c2Cl)[nH]c1=O] |
| I-64 | 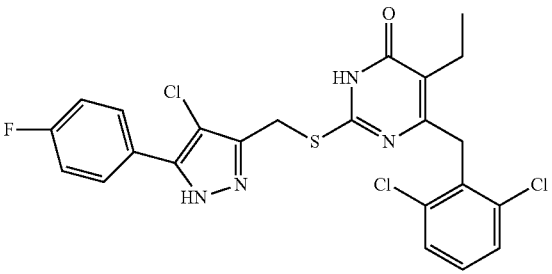 [SMILES: CCc1c(Cc2c(Cl)cccc2Cl)nc(SCc2n[nH]c(-c3ccc(F)cc3)c2Cl)[nH]c1=O] |
| I-65 | 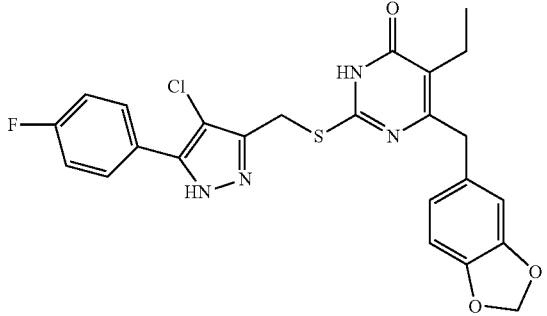 [SMILES: CCc1c(Cc2ccc3c(c2)OCO3)nc(SCc2n[nH]c(-c3ccc(F)cc3)c2Cl)[nH]c1=O] |
| I-66 | 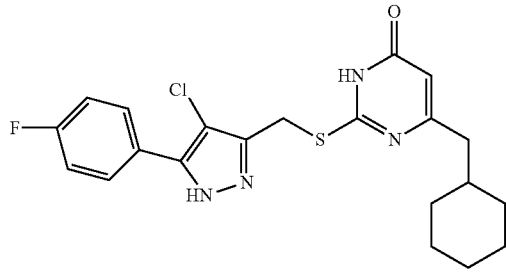 [SMILES: O=c1cc(CC2CCCCC2)nc(SCc2n[nH]c(-c3ccc(F)cc3)c2Cl)[nH]1] |
| I-67 | 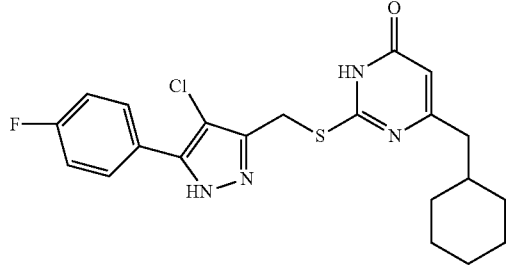 [SMILES: O=c1cc(CC2CCCCC2)nc(SCc2n[nH]c(-c3ccc(F)cc3)c2Cl)[nH]1] |

-continued

| Compound | Structure |
|---|---|
| I-68 | 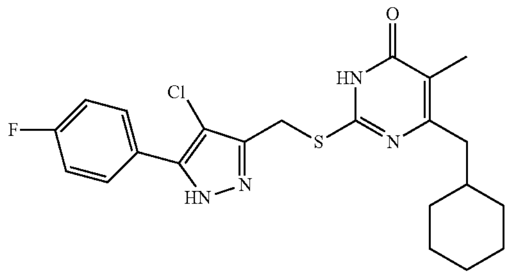 [SMILES: Cc1c(CC2CCCCC2)nc(SCc2n[nH]c(-c3ccc(F)cc3)c2Cl)[nH]c1=O] |
| I-69 | 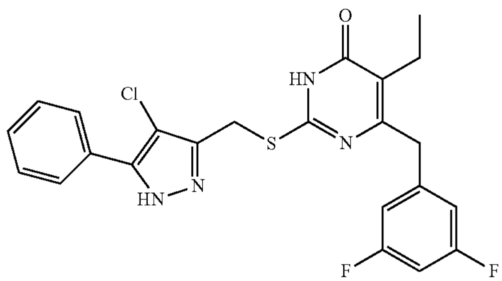 [SMILES: CCc1c(Cc2cc(F)cc(F)c2)nc(SCc2n[nH]c(-c3ccccc3)c2Cl)[nH]c1=O] |
| I-70 | 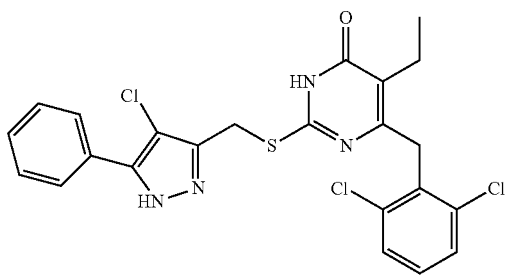 [SMILES: CCc1c(Cc2c(Cl)cccc2Cl)nc(SCc2n[nH]c(-c3ccccc3)c2Cl)[nH]c1=O] |
| I-71 | 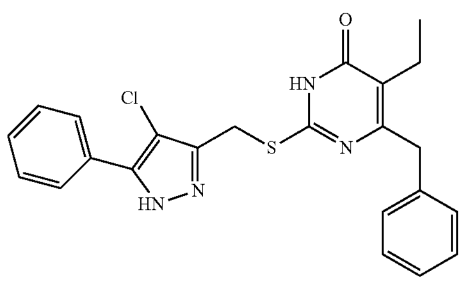 [SMILES: CCc1c(Cc2ccccc2)nc(SCc2n[nH]c(-c3ccccc3)c2Cl)[nH]c1=O] |
| I-72 | | or a N-oxide, tautomer, optical isomer, hydrate, solvate, or pharmaceutically acceptable salt thereof.

10. A method for preparing a compound as defined in claim 1, comprising carrying out an alkylation reaction of intermediate 6 and intermediate 7 in the presence of a base in a solvent;

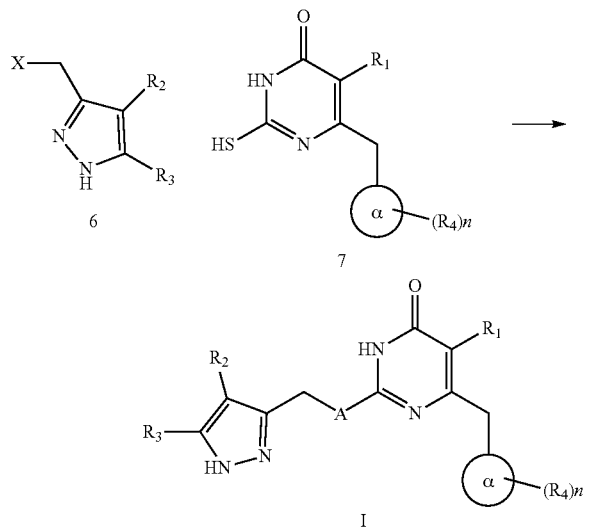

wherein the definitions of A, n, $R_1$, $R_2$, $R_3$, $R_4$ and α ring are as previously defined, X is halogen.

11. The method of claim 10, wherein the method further comprises carrying out a halogenation reaction of intermediate 5 with a halogenating agent in a solvent to obtain the intermediate 6; the halogenating agent is one or more selected from $Br_2$, $PBr_3$, $CBr_4$, NBS, NCS, $POCl_3$ and $I_2$;

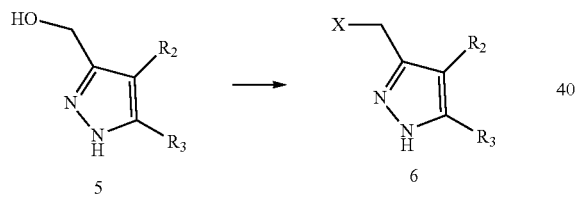

wherein the definitions of $R_2$ and $R_3$ are as previously defined, X is halogen.

12. The method of claim 11, wherein the method further comprises carrying out a reduction reaction of intermediate 4 in the presence of a reducing agent in a solvent to obtain the intermediate 5;

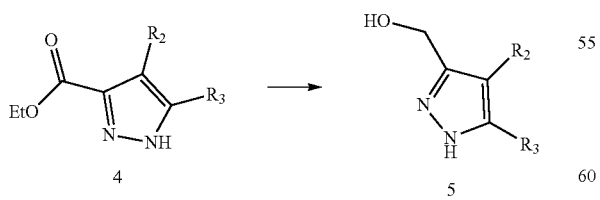

wherein the definitions of $R_2$ and $R_3$ are previously as defined.

13. The method of claim 12, wherein the method further comprises carrying out a halogenation reaction of intermediate 3 with a halogenating agent in a solvent to obtain the intermediate 4; the halogenating agent is one or more selected from NBS, NCS and NIS;

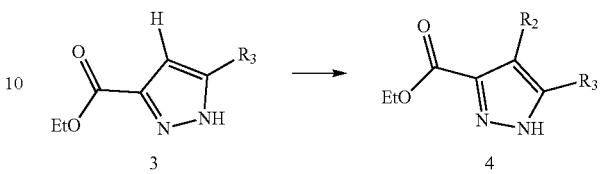

wherein the definitions of $R_2$ and $R_3$ are as previously defined.

14. A method for inhibiting non-nucleoside HIV-1 in a subject in need thereof, comprising administering a therapeutically effective amount of the compound as defined in claim 1 to the subject.

15. The method as defined in claim 14, wherein the non-nucleoside HIV-1 is non-nucleoside HIV-$1_{IIIB}$.

16. A pharmaceutical composition, comprising a therapeutically effective amount of the compound as defined in claim 1, and at least one pharmaceutical excipient.

17. A method for treating human immunodeficiency virus infection disease, comprising administering a therapeutically effective amount of the compound as defined in claim 1 to a subject in need thereof.

18. The compound as defined in claim 1, wherein,
when $R_3$ is $C_6$-$C_{20}$ aryl substituted by one or more $R_{3a}$, or $C_2$-$C_{10}$ heteroaryl substituted by one or more $R_{3b}$, then the one or more is 1-2.

19. The compound as defined in claim 1, wherein,
A is S, α ring is

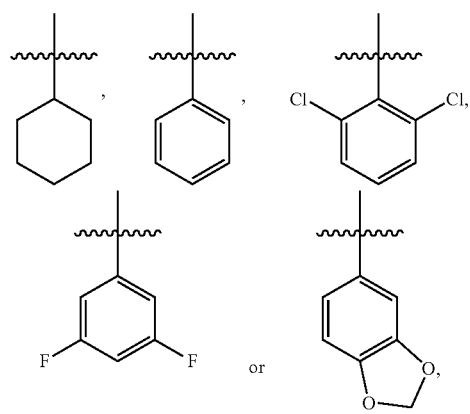

$R_1$ is ethyl or isopropyl; $R_2$ is H or Cl; $R_3$ is phenyl or phenyl substituted by one $R_{3a}$, wherein $R_{3a}$ is hydroxyl, halogen, $C_1$-$C_6$ branched or straight chain alkoxy or $C_1$-$C_6$ branched or straight chain alkylthio; the substituted is 4-substituted.

20. The compound as defined in claim 1, wherein,
A is S, α ring is cyclohexyl, $R_1$ is ethyl or isopropyl; $R_2$ is H or Cl; $R_3$ is phenyl or phenyl substituted by one $R_{3a}$, wherein $R_{3a}$ is hydroxyl, F, Cl, methoxy or methylthio; the substituted is 4-substituted.

* * * * *